US007030295B2

(12) United States Patent
Chen et al.

(10) Patent No.: US 7,030,295 B2
(45) Date of Patent: Apr. 18, 2006

(54) MODIFIED CRY3A TOXINS AND NUCLEIC ACID SEQUENCES CODING THEREFOR

(75) Inventors: Eric Chen, Chapel Hill, NC (US); Cheryl Stacy, Raleigh, NC (US)

(73) Assignee: Syngenta Participations AG, Basel (CH)

( * ) Notice: Subject to any disclaimer, the term of this patent is extended or adjusted under 35 U.S.C. 154(b) by 2 days.

(21) Appl. No.: 10/229,346

(22) Filed: Aug. 27, 2002

(65) Prior Publication Data

US 2003/0120054 A1 Jun. 26, 2003

Related U.S. Application Data

(60) Provisional application No. 60/316,421, filed on Aug. 31, 2001.

(51) Int. Cl.
*A01H 5/00* (2006.01)
*A01H 5/10* (2006.01)
*C12N 15/82* (2006.01)
*C12N 15/32* (2006.01)
*C12N 5/10* (2006.01)

(52) U.S. Cl. .................. 800/302; 536/23.71; 800/279; 800/320.3; 424/93.2; 435/320.1; 435/418; 435/252.3; 435/70.1

(58) Field of Classification Search ................ 800/302, 800/320.1; 536/23.71; 424/93.2; 435/320.1, 435/418

See application file for complete search history.

(56) References Cited

U.S. PATENT DOCUMENTS

| 5,659,123 A | 8/1997 | Van Rie et al. ............. 800/205 |
| 5,763,241 A | 6/1998 | Fischhoff et al. ......... 435/172.3 |
| 6,013,523 A * | 1/2000 | Adang et al. ............... 435/419 |
| 6,063,597 A | 5/2000 | Walters et al. |

FOREIGN PATENT DOCUMENTS

| WO | WO99/00407 | 1/1999 |
| WO | WO 99/31248 | 6/1999 |

OTHER PUBLICATIONS

Haider et al, *Specificity of Bacillus Thuringiensis Var. Colmeri Insecticidal Delta-Endotoxin in Determined by Differential Proteolytic Processing of the Protoxin by Larval Gut Proteases* European Journal of Biochemistry, vol. 156, No. 3 (May 1, 1986), pp. 531-540.

Smedley et al, *Mutagenesis of three surface-exposed loops of a Bacillus thuringiensis insecticidal toxin reveals residues important for toxicity, receptor recognition and possibly membrane insertion* Society for General Microbiology, vol. 142, No. Part 7 (July 1996), vol. 1617-1624.

Adang et al, *The reconstruction and expression of a Bacillus thuringiensis cryIIIA gene in protoplasts and potato plants* Plant Molecular Biology, vol. 21 (1993), pp. 1131-1145.

Carroll et al, *Proteolytic processing of a coleopteran-specific δ-endotoxin produced by Bacillus thuringiensis var. tenebrionis* Biochemical Journal, vol. 26 (1989), pp. 99-105.

Carroll et al, *Intramolecular Proteolytic Cleavage of Bacillus thuringiensis Cry3A δ-Endotoxin May Facilitate Its Coleopteran Toxicity* Journal of Invertebrate Pathology, vol. 70 (1997) pp. 41-49.

Gazit et al, *The structure and organization within the membrane of the helices composing the pore-forming domain of Bacillus thuringiensis δ-endotoxin are consistent with an "umbrella-like" structure of the pore* Proceedings of the National Academy of Sciences, USA, vol. 95 (Oct. 1998), pp. 12289-12294.

Gazit, E. and Shai, Y., *The Assembly and Organization of the a 5 and a7 Helices from the Pore-forming Domain of Bacillus thuringiensis δ-endotoxin* The Journal of Biological Chemistry, vol. 270, No. 6 (Feb. 10, 1995), pp. 2571-2578.

(Continued)

*Primary Examiner*—Anne Kubelik
(74) *Attorney, Agent, or Firm*—Syngenta Participations AG

(57) ABSTRACT

Compositions and methods for controlling plant pests are disclosed. In particular, novel nucleic acid sequences encoding modified Cry3A toxins having increased toxicity to corn rootworm are provided. By inserting a protease recognition site, such as cathepsin G, that is recognized by a gut protease of a target insect in at least one position of a Cry3A toxin a modified Cry3A toxin having significantly greater toxicity, particularly to western and northern corn rootworm is designed. Further, a method of making the modified Cry3A toxins and methods of using the modified cry3A nucleic acid sequences, for example in microorganisms to control insects or in transgenic plants to confer protection from insect damage, and a method of using the modified Cry3A toxins, and compositions and formulations comprising the modified Cry3A toxins, for example applying the modified Cry3A toxins or compositions or formulations to insect-infested areas, or to prophylactically treat insect-susceptible areas or plants to confer protection against the insect pests are disclosed.

60 Claims, No Drawings

OTHER PUBLICATIONS

Gillikin et al, *Partial Characterization of Digestive Tract Proteinases from Western Corn Rootworm Larvae, Diabrotica virgifera* Archives of Insect Biochemistry and Physiology, vol. 19 (1992), pp. 285-298.

Li et al, *Crystal structure of insecticidal δ-endotoxin from Bacillus thuringiensis at 2.5 Å resolution* Nature, vol. 353 (Oct. 31, 1991), pp. 815-821.

Martinez-Ramirez, A.C. and Real M.D., *Proteolytic Processing of Bacillus thuringiensis CryIIIA Toxin and Specific Binding to Brush-Border Membrane Vesicles of Leptinotarsa decemlineata (Colorado Potato Beetle)* Pesticide Biochemistry and Physiology, vol. 54 (1996), pp. 115-122, Article No. 0015.

McPherson et al, *Characterization of the Cleopteran-Specific Protein Gene of Bacillus Thuringiensis Var. Tenebrionis* Bio/Technology, vol. 6 (1998), pp. 61-66.

Oppert, B., *Protease Interactions With Bacillus thuringiensis Insecticidal Toxins* Archives of Insect Biochemistry and Physiology, vol. 42 (1999), pp. 1-12.

Sekar et al., *Molecular cloning and characterization of the insecticidal crystal protein gene of Bacillus thuringiensis var. tenebrionis* Proceedings of the National Academy of Sciences, USA, vol. 84 (Oct. 1987), pp. 7036-7040.

Slaney et al, *Mode of Action of Bacillus Thuringiensis Toxin CryIIIA: An Analysis of Toxicity in Leptinotarsa Decemlineata (Say) and Diabrotica Undecimpunctata Howardi Barber* Insect Biochemistry Molecular Biology, vol. 22, No. 1 (1992), pp. 9-18.

Sutton et al, *Synthetic cryIIIA gene from Bacillus thuringiensis improved for high expression in plants* Transgenic Research, vol. 1 (1992), pp. 228-236.

Wu, S.J., Dean, D.H., *Functional Significance of Loops in The Receptor Binding Domain of Bacillus thuringiensis CryIIIA δ-Endotoxin* Journal of Molecular Biology, vol. 255 (1996), pp. 628-640.

Wu et al, *Enhanced toxicity of Bacillus thuringiensis Cry3A δ-Endotoxin in coleopterans by mutagenesis in a receptor binding loop* Federation of European Biochemical Societies Letters, vol. 473 (2000), pp. 227-232.

* cited by examiner

US 7,030,295 B2

MODIFIED CRY3A TOXINS AND NUCLEIC ACID SEQUENCES CODING THEREFOR

This application claims the benefit of U.S. Provisional Application No. 60/316,421 filed Aug. 31, 2001 that is incorporated herein by reference in its entirety.

FIELD OF THE INVENTION

The present invention relates to the fields of protein engineering, plant molecular biology and pest control. More particularly, the present invention relates to novel modified Cry3A toxins and nucleic acid sequences whose expression results in the modified Cry3A toxins, and methods of making and methods of using the modified Cry3A toxins and corresponding nucleic acid sequences to control insects.

BACKGROUND OF THE INVENTION

Species of corn rootworm are considered to be the most destructive corn pests. In the United States the three important species are *Diabrotica virgifera virgifera*, the western corn rootworm; *D. longicornis barberi*, the northern corn rootworm and *D. undecimpunctata howardi*, the southern corn rootworm. Only western and northern corn rootworms are considered primary pests of corn in the US Corn Belt. Corn rootworm larvae cause the most substantial plant damage by feeding almost exclusively on corn roots. This injury has been shown to increase plant lodging, to reduce grain yield and vegetative yield as well as alter the nutrient content of the grain. Larval feeding also causes indirect effects on maize by opening avenues through the roots for bacterial and fungal infections which lead to root and stalk rot diseases. Adult corn rootworms are active in cornfields in late summer where they feed on ears, silks and pollen, interfering with normal pollination.

Corn rootworms are mainly controlled by intensive applications of chemical pesticides, which are active through inhibition of insect growth, prevention of insect feeding or reproduction, or cause death. Good corn rootworm control can thus be reached, but these chemicals can sometimes also affect other, beneficial organisms. Another problem resulting from the wide use of chemical pesticides is the appearance of resistant insect varieties. Yet another problem is due to the fact that corn rootworm larvae feed underground thus making it difficult to apply rescue treatments of insecticides. Therefore, most insecticide applications are made prophylactically at the time of planting. This practice results in a large environmental burden. This has been partially alleviated by various farm management practices, but there is an increasing need for alternative pest control mechanisms.

Biological pest control agents, such as *Bacillus thuringiensis* (Bt) strains expressing pesticidal toxins like δ-endotoxins, have also been applied to crop plants with satisfactory results against primarily lepidopteran insect pests. The δ-endotoxins are proteins held within a crystalline matrix that are known to possess insecticidal activity when ingested by certain insects. The various δ-endotoxins have been classified based upon their spectrum of activity and sequence homology. Prior to 1990, the major classes were defined by their spectrum of activity with the Cry1 proteins active against Lepidoptera (moths and butterflies), Cry2 proteins active against both Lepidoptera and Diptera (flies and mosquitoes), Cry3 proteins active against Coleoptera (beetles) and Cry4 proteins active against Diptera (Hofte and Whitely, 1989, Microbiol. Rev. 53:242–255). Recently a new nomenclature was developed which systematically classifies the Cry proteins based on amino acid sequence homology rather than insect target specificities (Crickmore et al. 1998, Microbiol. Molec. Biol. Rev. 62:807–813).

The spectrum of insecticidal activity of an individual δ-endotoxin from Bt is quite narrow, with a given δ-endotoxin being active against only a few species within an Order. For instance, the Cry3A protein is known to be very toxic to the Colorado potato beetle, *Leptinotarsa decemlineata*, but has very little or no toxicity to related beetles in the genus *Diabrotica* (Johnson et al., 1993, J. Econ. Entomol. 86:330–333). According to Slaney et al. (1992, Insect Biochem. Molec. Biol. 22:9–18) the Cry3A protein is at least 2000 times less toxic to southern corn rootworm larvae than to the Colorado potato beetle. It is also known that Cry3A has little or no toxicity to the western corn rootworm.

Specificity of the δ-endotoxins is the result of the efficiency of the various steps involved in producing an active toxin protein and its subsequent interaction with the epithelial cells in the insect mid-gut. To be insecticidal, most known δ-endotoxins must first be ingested by the insect and proteolytically activated to form an active toxin. Activation of the insecticidal crystal proteins is a multi-step process. After ingestion, the crystals must first be solubilized in the insect gut. Once solubilized, the δ-endotoxins are activated by specific proteolytic cleavages. The proteases in the insect gut can play a role in specificity by determining where the δ-endotoxin is processed. Once the δ-endotoxin has been solubilized and processed it binds to specific receptors on the surface of the insects' mid-gut epithelium and subsequently integrates into the lipid bilayer of the brush border membrane. Ion channels then form disrupting the normal function of the midgut eventually leading to the death of the insect.

In Lepidoptera, gut proteases process δ-endotoxins from 130–140 kDa protoxins to toxic proteins of approximately 60–70 kDa. Processing of the protoxin to toxin has been reported to proceed by removal of both N- and C-terminal amino acids with the exact location of processing being dependent on the specific insect gut fluids involved (Ogiwara et al., 1992, J. Invert. Pathol. 60:121–126). The proteolytic activation of a δ-endotoxin can play a significant role in determining its specificity. For example, a δ-endotoxin from Bt var. aizawa, called IC1, has been classified as a Cry1Ab protein based on its sequence homology with other known Cry1Ab proteins. Cry1Ab proteins are typically active against lepidopteran insects. However, the IC1 protein has activity against both lepidopteran and dipteran insects depending upon how the protein is processed (Haider et al. 1986, Euro. J. Biochem. 156: 531–540). In a dipteran gut, a 53 kDa active IC1 toxin is obtained, whereas in a lepidopteran gut, a 55 kDa active IC1 toxin is obtained. IC1 differs from the holotype HD-1 Cry1Ab protein by only four amino acids, so gross changes in the receptor binding region do not seem to account for the differences in activity. The different proteolytic cleavages in the two different insect guts possibly allow the activated molecules to fold differently thus exposing different regions capable of binding different receptors. The specificity therefore, appears to reside with the gut proteases of the different insects.

Coleopteran insects have guts that are more neutral to acidic and coleopteran-specific δ-endotoxins are similar to the size of the activated lepidopteran-specific toxins. Therefore, the processing of coleopteran-specific δ-endotoxins was formerly considered unnecessary for toxicity. However, recent data suggests that coleopteran-active δ-endotoxins are solubilized and proteolyzed to smaller toxic polypeptides. The 73 kDa Cry3A δ-endotoxin protein produced by

*B. thuringiensis* var. *tenebrionis* is readily processed in the bacterium at the N-terminus, losing 49–57 residues during or after crystal formation to produce the commonly isolated 67 kDa form (Carroll et al., 1989, Biochem. J. 261:99–105). McPherson et al., 1988 (Biotechnology 6:61–66) also demonstrated that the native cry3A gene contains two functional translational initiation codons in the same reading frame, one coding for the 73 kDa protein and the other coding for the 67 kDa protein starting at Met-1 and Met-48 respectively, of the deduced amino acid sequence (See SEQ ID NO: 2). Both proteins then can be considered naturally occurring full-length Cry3A proteins. Treatment of soluble 67 kDa Cry3A protein with either trypsin or insect gut extract results in a cleavage product of 55 kDa with Asn-159 of the deduced amino acid sequence at the N-terminus. This polypeptide was found to be as toxic to a susceptible coleopteran insect as the native 67 kDa Cry3A toxin. (Carroll et al. Ibid). Thus, a natural trypsin recognition site exists between Arg-158 and Asn-159 of the deduced amino acid sequence of the native Cry3A toxin (SEQ ID NO: 2). Cry3A can also be cleaved by chymotrypsin, resulting in three polypeptides of 49, 11, and 6 kDa. N-terminal analysis of the 49 and 6 kDa components showed the first amino acid residue to be Ser-162 and Tyr-588, respectively (Carroll et al., 1997 J. Invert. Biol. 70:41–49). Thus, natural chymotrypsin recognition sites exist in Cry3A between His-161 and Ser-162 and between Tyr-587 and Tyr-588 of the deduced amino acid sequence (SEQ ID NO: 2). The 49 kDa chymotrypsin product appears to be more soluble at neutral pH than the native 67 kDa protein or the 55 kDa trypsin product and retains full insecticidal activity against the Cry3A-susceptible insects, Colorado potato beetle and mustard beetle, (*Phaedon cochleariae*).

Insect gut proteases typically function in aiding the insect in obtaining needed amino acids from dietary protein. The best understood insect digestive proteases are serine proteases that appear to be the most common (Englemann and Geraerts, 1980, J. Insect Physiol. 261:703–710), particularly in lepidopteran species. The majority of coleopteran larvae and adults, for example Colorado potato beetle, have slightly acidic midguts, and cysteine proteases provide the major proteolytic activity (Wolfson and Mudock, 1990, J. Chem. Ecol. 16:1089–1102). More precisely, Thie and Houseman (1990, Insect Biochem. 20:313–318) identified and characterized the cysteine proteases, cathepsin B and H, and the aspartyl protease, cathepsin D in Colorado potato beetle. Gillikin et al. (1992, Arch. Insect Biochem. Physiol. 19:285–298) characterized the proteolytic activity in the guts of western corn rootworm larvae and found 15, primarily cysteine, proteases. Until disclosed in this invention, no reports have indicated that the serine protease, cathepsin G, exists in western corn rootworm. The diversity and different activity levels of the insect gut proteases may influence an insect's sensitivity to a particular Bt toxin.

Many new and novel Bt strains and δ-endotoxins with improved or novel biological activities have been described over the past five years including strains active against nematodes (EP 0517367A1). However, relatively few of these strains and toxins have activity against coleopteran insects. Further, none of the now known coleopteran-active δ-endotoxins, for example Cry3A, Cry3B, Cry3C, Cry7A, Cry8A, Cry8B, and Cry8C, have sufficient oral toxicity against corn rootworm to provide adequate field control if delivered, for example, through microbes or transgenic plants. Therefore, other approaches for producing novel toxins active against corn rootworm need to be explored.

As more knowledge has been gained as to how the δ-endotoxins function, attempts to engineer δ-endotoxins to have new activities have increased. Engineering δ-endotoxins was made more possible by the solving of the three dimensional structure of Cry3A in 1991 (Li et al., 1991, Nature 353:815–821). The protein has three structural domains: the N-terminal domain I, from residues 1–290, consists of 7 alpha helices, domain II, from residues 291–500, contains three beta-sheets and the C-terminal domain III, from residues 501–644, is a beta-sandwich. Based on this structure, a hypothesis has been formulated regarding the structure/function relationship of the δ-endotoxins. It is generally thought that domain I is primarily responsible for pore formation in the insect gut membrane (Gazit and Shai, 1993, Appl. Environ. Microbiol. 57:2816–2820), domain II is primarily responsible for interaction with the gut receptor (Ge et al., 1991, J. Biol. Chem. 32:3429–3436) and that domain III is most likely involved with protein stability (Li et al. 1991, supra) as well as having a regulatory impact on ion channel activity (Chen et al., 1993, PNAS 90:9041–9045).

Lepidopteran-active δ-endotoxins have been engineered in attempts to improve specific activity or to broaden the spectrum of insecticidal activity. For example, the silk moth (*Bombyx mori*) specificity domain from Cry1Aa was moved to Cry1Ac, thus imparting a new insecticidal activity to the resulting chimeric protein (Ge et al. 1989, PNAS 86: 4037–4041). Also, Bosch et al. 1998 (U.S. Pat. No. 5,736, 131), created a new lepidopteran-active toxin by substituting domain III of Cry1E with domain III of Cry1C thus producing a Cry1E–Cry1C hybrid toxin with a broader spectrum of lepidopteran activity.

Several attempts at engineering the coleopteran-active δ-endotoxins have been reported. Van Rie et al., 1997, (U.S. Pat. No. 5,659,123) engineered Cry3A by randomly replacing amino acids, thought to be important in solvent accessibility, in domain II with the amino acid alanine. Several of these random replacements confined to receptor binding domain II were reportedly involved in increased western corn rootworm toxicity. However, others have shown that some alanine replacements in domain II of Cry3A result in disruption of receptor binding or structural instability (Wu and Dean, 1996, J. Mol. Biol. 255: 628–640). English et al., 1999, (Intl. Pat. Appl. Publ. No. WO 99/31248) reported amino acid substitutions in Cry3Bb that caused increases in toxicity to southern and western corn rootworm. However, of the 35 reported Cry3Bb mutants, only three, with mutations primarily in domain II and the domain II-domain I interface, were active against western corn rootworm. Further, the differences in toxicity of wild-type Cry3Bb against western corn rootworm in the same assays were greater than any of the differences between the mutated Cry3Bb toxins and the wild-type Cry3Bb. Therefore, improvements in toxicity of the Cry3Bb mutants appear to be confined primarily to southern corn rootworm.

There remains a need to design new and effective pest control agents that provide an economic benefit to farmers and that are environmentally acceptable. Particularly needed are modified Cry3A toxins that control western corn rootworm, the major pest of corn in the United States, that are or could become resistant to existing insect control agents. Furthermore, agents whose application minimizes the burden on the environment, as through transgenic plants, are desirable.

SUMMARY

In view of these needs, it is an object of the present invention to provide novel nucleic acid sequences encoding modified Cry3A toxins having increased toxicity to corn rootworm. By inserting a protease recognition site that is recognized by a target-insect gut protease in at least one position of a Cry3A toxin, in accordance with the present invention, a modified Cry3A toxin having significantly greater toxicity, particularly to western and northern corn rootworm is designed. The invention is further drawn to the novel modified Cry3A toxins resulting from the expression of the nucleic acid sequences, and to compositions and formulations containing the modified Cry3A toxins, which are capable of inhibiting the ability of insect pests to survive, grow and reproduce, or of limiting insect-related damage or loss to crop plants. The invention is further drawn to a method of making the modified Cry3A toxins and to methods of using the modified cry3A nucleic acid sequences, for example in microorganisms to control insects or in transgenic plants to confer protection from insect damage, and to a method of using the modified Cry3A toxins, and compositions and formulations comprising the modified Cry3A toxins, for example applying the modified Cry3A toxins or compositions or formulations to insect-infested areas, or to prophylactically treat insect-susceptible areas or plants to confer protection against the insect pests.

The novel modified Cry3A toxins described herein are highly active against insects. For example, the modified Cry3A toxins of the present invention can be used to control economically important insect pests such as western corn rootworm (*Diabrotica virgifera virgifera*) and northern corn rootworm (*D. longicornis barberi*). The modified Cry3A toxins can be used singly or in combination with other insect control strategies to confer maximal pest control efficiency with minimal environmental impact.

According to one aspect, the present invention provides an isolated nucleic acid molecule comprising a nucleotide sequence that encodes a modified Cry3A toxin, wherein the modified Cry3A toxin comprises at least one additional protease recognition site that does not naturally occur in a Cry3A toxin. The additional protease recognition site, which is recognized by a gut protease of a target insect, is inserted at approximately the same position as a naturally occurring protease recognition site in the Cry3A toxin. The modified Cry3A toxin causes higher mortality to a target insect than the mortality caused by a Cry3A toxin to the same target insect. Preferably, the modified Cry3A toxin causes at least about 50% mortality to a target insect to which a Cry3A toxin causes only up to about 30% mortality.

In one embodiment of this aspect, the gut protease of a target insect is selected from the group consisting of serine proteases, cysteine proteases and aspartic proteases. Preferable serine proteases according to this embodiment include cathepsin G, trypsin, chymotrypsin, carboxypeptidase, endopeptidase and elastase, most preferably cathepsin G.

In another embodiment of this aspect, the additional protease recognition site is inserted in either domain I or domain III or in both domain I and domain III of the Cry3A toxin. Preferably, the additional protease recognition site is inserted in either domain I or domain III or in both domain I and domain III at a position that replaces, is adjacent to, or is within a naturally occurring protease recognition site.

In a yet another embodiment, the additional protease recognition site is inserted in domain I between amino acids corresponding to amino acid numbers 154 and 162 of SEQ ID NO: 2. Preferably, the additional protease recognition site is inserted between amino acid numbers 154 and 162 of SEQ ID NO: 2 or between amino acid numbers 107 and 115 of SEQ ID NO: 4.

In still another embodiment, the additional protease recognition site is inserted between amino acids corresponding to amino acid numbers 154 and 160 of SEQ ID NO: 2. Preferably, the additional protease recognition site is inserted between amino acid numbers 154 and 160 of SEQ ID NO: 2 or between amino acid numbers 107 and 113 of SEQ ID NO: 4.

In a further embodiment, the additional protease recognition site is inserted in domain I between amino acids corresponding to amino acid numbers 154 and 158 of SEQ ID NO: 2. Preferably, the additional protease recognition site is inserted in domain I between amino acid numbers 154 and 158 of SEQ ID NO: 2 or between amino acid numbers 107 and 111 of SEQ ID NO: 4.

In another embodiment, the additional protease recognition site is inserted in domain III between amino acids corresponding to amino acid numbers 583 and 589 of SEQ ID NO: 2. Preferably, the additional protease site is inserted in domain III between amino acid numbers 583 and 589 of SEQ ID NO: 2 or between amino acid numbers 536 and 542 of SEQ ID NO: 4.

In still another embodiment, the additional protease recognition site is inserted in domain III between amino acids corresponding to amino acid numbers 583 and 588 of SEQ ID NO: 2. Preferably, the additional protease site is inserted in domain III between amino acid numbers 583 and 588 of SEQ ID NO: 2 or between amino acid numbers 536 and 541 of SEQ ID NO: 4.

In yet another embodiment, the additional protease recognition site is inserted in domain III between amino acids corresponding to amino acid numbers 587 and 588 of SEQ ID NO: 2. Preferably, the additional protease site is inserted in domain III between amino acid numbers 587 and 588 of SEQ ID NO: 2 or between amino acid numbers 540 and 541 of SEQ ID NO: 4.

In one embodiment, the additional protease recognition site is inserted in domain I and domain III of the unmodified Cry3A toxin. Preferably, the additional protease recognition site is inserted in domain I at a position that replaces or is adjacent to a naturally occurring protease recognition site and in domain III at a position that is within, replaces, or is adjacent to a naturally occurring protease recognition site.

In another embodiment, the additional protease recognition site is inserted in domain I between amino acids corresponding to amino acid numbers 154 and 160 and in domain III between amino acids corresponding to amino acid numbers 587 and 588 of SEQ ID NO: 2. Preferably, the additional protease recognition site is inserted in domain I between amino acid numbers 154 and 160 and in domain III between amino acid numbers 587 and 588 of SEQ ID NO: 2 or in domain I between amino acid numbers 107 and 113 and in domain III between amino acid numbers 540 and 541 of SEQ ID NO: 4.

In yet another embodiment, the additional protease recognition site is located in domain I between amino acids corresponding to amino acid numbers 154 and 158 and in domain III between amino acids corresponding to amino acid numbers 587 and 588 of SEQ ID NO: 2. Preferably, the additional protease recognition site is inserted in domain I between amino acid numbers 154 and 158 and in domain III between amino acid numbers 587 and 588 of SEQ ID NO: 2 or in domain I between amino acid numbers 107 and 111 and in domain III between amino acid numbers 540 and 541 of SEQ ID NO: 4.

In another embodiment, the additional protease recognition site is located in domain I between amino acids corresponding to amino acid numbers 154 and 158 and in domain III between amino acids corresponding to amino acid numbers 583 and 588 of SEQ ID NO: 2. Preferably, the additional protease recognition site is inserted in domain I between amino acid numbers 154 and 158 and in domain III between amino acid numbers 583 and 588 of SEQ ID NO: 2 or in domain I between amino acid numbers 107 and 111 and in domain III between amino acid numbers 536 and 541 of SEQ ID NO: 4.

In a preferred embodiment, the isolated nucleic acid molecule of the present invention comprises nucleotides 1–1791 of SEQ ID NO: 6, nucleotides 1–1806 of SEQ ID NO: 8, nucleotides 1–1818 of SEQ ID NO: 10, nucleotides 1–1794 of SEQ ID NO: 12, nucleotides 1–1 812 of SEQ ID NO: 14, nucleotides 1–1812 of SEQ ID NO: 16, nucleotides 1–1818 of SEQ ID NO: 18, or nucleotides 1–1791 of SEQ ID NO: 20.

In another preferred embodiment, the isolated nucleic acid molecule of the invention encodes a modified Cry3A toxin comprising the amino acid sequence set forth in SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21.

According to one embodiment of the invention, the isolated nucleic acid molecule encodes a modified Cry3A toxin that is active against a coleopteran insect. Preferably, the modified Cry3A toxin has activity against western corn rootworm.

The present invention provides a chimeric gene comprising a heterologous promoter sequence operatively linked to the nucleic acid molecule of the invention. The present invention also provides a recombinant vector comprising such a chimeric gene. Further, the present invention provides a transgenic non-human host cell comprising such a chimeric gene. A transgenic host cell according to this aspect of the invention may be a bacterial cell or a plant cell, preferably, a plant cell. The present invention further provides a transgenic plant comprising such a plant cell. A transgenic plant according to this aspect of the invention may be sorghum, wheat, sunflower, tomato, potato, cole crops, cotton, rice, soybean, sugar beet, sugarcane, tobacco, barley, oilseed rape, or maize, preferably, maize. The present invention also provides seed from the group of transgenic plants consisting of sorghum, wheat, sunflower, tomato, potato, cole crops, cotton, rice, soybean, sugar beet, sugarcane, tobacco, barley, oilseed rape, and maize. In a particularly preferred embodiment, the seed is from a transgenic maize plant.

In another aspect, the present invention provides toxins produced by the expression of the nucleic acid molecules of the present invention. In a preferred embodiment, the toxin is produced by the expression of the nucleic acid molecule comprising nucleotides 1–1791 of SEQ ID NO: 6, nucleotides 1–1806 of SEQ ID NO: 8, nucleotides 1–1818 of SEQ ID NO: 10, nucleotides 1–1794 of SEQ ID NO: 12, nucleotides 1–1812 of SEQ ID NO: 14, nucleotides 1–1812 of SEQ ID NO: 16, nucleotides 1–1818 of SEQ ID NO: 18, or nucleotides 1–1791 of SEQ ID NO: 20.

In another embodiment, the toxins of the invention are active against coleopteran insects, preferably against western corn rootworm.

In one embodiment, a toxin of the present invention comprises the amino acid sequence set forth in SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21.

The present invention also provides a composition comprising an effective insect-controlling amount of a toxin according to the invention.

In another aspect, the present invention provides a method of producing a toxin that is active against insects, comprising: (a) obtaining a host cell comprising a chimeric gene, which itself comprises a heterologous promoter sequence operatively linked to the nucleic acid molecule of the invention; and (b) expressing the nucleic acid molecule in the transgenic host cell, which results in at least one toxin that is active against insects.

In a further aspect, the present invention provides a method of producing an insect-resistant transgenic plant, comprising introducing a nucleic acid molecule of the invention into the transgenic plant, wherein the nucleic acid molecule is expressible in the transgenic plant in an effective amount to control insects. In a preferred embodiment, the insects are coleopteran insects, preferably western corn rootworm.

In yet a further aspect, the present invention provides a method of controlling insects, comprising delivering to the insects an effective amount of a toxin of the invention. According to one embodiment, the insects are coleopteran insects, preferably, western corn rootworm.

Preferably, the toxin is delivered to the insects orally. In one preferred embodiment, the toxin is delivered orally through a transgenic plant comprising a nucleic acid sequence that expresses a toxin of the present invention.

Also provided by the present invention is a method of making a modified Cry3A toxin, comprising: (a) obtaining a cry3A toxin gene which encodes a Cry3A toxin; (b) identifying a gut protease of a target insect; (c) obtaining a nucleotide sequence which encodes a recognition sequence for the gut protease; (d) inserting the nucleotide sequence of (c) into either domain I or domain III or both domain I and domain III at a position that replaces, is within, or adjacent to a nucleotide sequence that codes for a naturally occurring protease recognition site in a cry3A toxin gene, thus creating a modified cry3A toxin gene; (e) inserting the modified cry3A toxin gene in an expression cassette; (f) expressing the modified cry3A toxin gene in a non-human host cell, resulting in the host cell producing a modified Cry3A toxin; and, (g) bioassaying the modified Cry3A toxin against a target insect, whereby the modified Cry3A toxin causes higher mortality to the target insect than the mortality caused by a Cry3A toxin. In a preferred embodiment, the modified Cry3A toxin causes at least about 50% mortality to the target insect when the Cry3A toxin causes up to about 30% mortality.

The present invention further provides a method of controlling insects wherein the transgenic plant further comprises a second nucleic acid sequence or groups of nucleic acid sequences that encode a second pesticidal principle. Particularly preferred second nucleic acid sequences are those that encode a δ-endotoxin, those that encode a Vegetative Insecticidal Protein toxin, disclosed in U.S. Pat. Nos. 5,849,870 and 5,877,012, incorporated herein by reference, or those that encode a pathway for the production of a non-proteinaceous pesticidal principle.

Yet another aspect of the present invention is the provision of a method for mutagenizing a nucleic acid molecule according to the present invention, wherein the nucleic acid molecule has been cleaved into populations of double-stranded random fragments of a desired size, comprising: (a)

adding to the population of double-stranded random fragments one or more single- or double-stranded oligonucleotides, wherein the oligonucleotides each comprise an area of identity and an area of heterology to a double-stranded template polynucleotide; (b) denaturing the resultant mixture of double-stranded random fragments and oligonucleotides into single-stranded fragments; (c) incubating the resultant population of single-stranded fragments with polymerase under conditions which result in the annealing of the single-stranded fragments at the areas of identity to form pairs of annealed fragments, the areas of identity being sufficient for one member of the pair to prime replication of the other, thereby forming a mutagenized double-stranded polynucleotide; and (d) repeating the second and third steps for at least two further cycles, wherein the resultant mixture in the second step of a further cycle includes the mutagenized double-stranded polynucleotide from the third step of the previous cycle, and wherein the further cycle forms a further mutagenized double-stranded polynucleotide.

Other aspects and advantages of the present invention will become apparent to those skilled in the art from a study of the following description of the invention and non-limiting examples.

BRIEF DESCRIPTION OF THE SEQUENCES IN THE SEQUENCE LISTING

SEQ ID NO: 1 is the native cry3A coding region.

SEQ ID NO: 2 is the amino acid sequence of the Cry3A toxin encoded by the native cry3A gene.

SEQ ID NO: 3 is the maize optimized cry3A coding region beginning at nucleotide 144 of the native cry3A coding region.

SEQ ID NO: 4 is the amino acid sequence of the Cry3A toxin encoded by the maize optimized cry3A gene.

SEQ ID NO: 5 is the nucleotide sequence of pCIB6850.

SEQ ID NO: 6 is the maize optimized modified cry3A054 coding sequence.

SEQ ID NO: 7 is the amino acid sequence encoded by the nucleotide sequence of SEQ ID NO: 6.

SEQ ID NO: 8 is the maize optimized modified cry3A055 coding sequence.

SEQ ID NO: 9 is the amino acid sequence encoded by the nucleotide sequence of SEQ ID NO: 8.

SEQ ID NO: 10 is the maize optimized modified cry3A085 coding sequence.

SEQ ID NO: 11 is the amino acid sequence encoded by the nucleotide sequence of SEQ ID NO: 10.

SEQ ID NO: 12 is the maize optimized modified cry3A082 coding sequence.

SEQ ID NO: 13 is the amino acid sequence encoded by the nucleotide sequence of SEQ ID NO: 12.

SEQ ID NO: 14 is the maize optimized modified cry3A058 coding sequence.

SEQ ID NO: 15 is the amino acid sequence encoded by the nucleotide sequence of SEQ ID NO: 14.

SEQ ID NO: 16 is the maize optimized modified cry3A057 coding sequence.

SEQ ID NO: 17 is the amino acid sequence encoded by the nucleotide sequence of SEQ ID NO: 16.

SEQ ID NO: 18 is the maize optimized modified cry3A056 coding sequence.

SEQ ID NO: 19 is the amino acid sequence encoded by the nucleotide sequence of SEQ ID NO: 18.

SEQ ID NO: 20 is the maize optimized modified cry3A083 coding sequence.

SEQ ID NO: 21 is the amino acid sequence encoded by the nucleotide sequence of SEQ ID NO: 20.

SEQ ID NOS: 22–34 are PCR primers useful in the present invention.

SEQ ID NO: 35 is an amino acid sequence comprising a cathepsin G recognition site.

SEQ ID NO: 36 is an amino acid sequence comprising a cathepsin G recognition site.

SEQ ID NO: 37 is an amino acid sequence comprising a cathepsin G recognition site.

SEQ ID NO: 38 is an amino acid sequence comprising a cathepsin G recognition site.

DEFINITIONS

For clarity, certain terms used in the specification are defined and presented as follows:

"Activity" of the modified Cry3A toxins of the invention is meant that the modified Cry3A toxins function as orally active insect control agents, have a toxic effect, or are able to disrupt or deter insect feeding, which may or may not cause death of the insect. When a modified Cry3A toxin of the invention is delivered to the insect, the result is typically death of the insect, or the insect does not feed upon the source that makes the modified Cry3A toxin available to the insect.

"Adjacent to"—According to the present invention, an additional protease recognition site is "adjacent to" a naturally occurring protease recognition site when the additional protease recognition site is within four residues, preferably within three residues, more preferably within two residues, and most preferably within one residue of a naturally occurring protease recognition site. For example, an additional protease recognition site inserted between Pro-154 and Arg-158 of the deduced amino acid sequence of a Cry3A toxin (SEQ ID NO: 2) is "adjacent to" the naturally occurring trypsin recognition site located between Arg-158 and Asn-159 of the deduced amino acid sequence of the Cry3A toxin (SEQ ID NO: 2).

The phrase "approximately the same position" as used herein to describe the location where an additional protease recognition site is inserted into a Cry3A toxin in relation to a naturally occurring protease recognition site, means that the location is at most four residues away from a naturally occurring protease recognition site. The location can also be three or two residues away from a naturally occurring protease recognition site. The location can also be one residue away from a naturally occurring protease recognition site. "Approximately the same position" can also mean that the additional protease recognition site is inserted within a naturally occurring protease recognition site.

"Associated with/operatively linked" refer to two nucleic acid sequences that are related physically or functionally. For example, a promoter or regulatory DNA sequence is said to be "associated with" a DNA sequence that codes for an RNA or a protein if the two sequences are operatively linked, or situated such that the regulatory DNA sequence will affect the expression level of the coding or structural DNA sequence.

A "chimeric gene" or "chimeric construct" is a recombinant nucleic acid sequence in which a promoter or regulatory nucleic acid sequence is operatively linked to, or associated with, a nucleic acid sequence that codes for an mRNA or which is expressed as a protein, such that the regulatory nucleic acid sequence is able to regulate transcription or expression of the associated nucleic acid coding sequence. The regulatory nucleic acid sequence of the chimeric gene is not normally operatively linked to the associated nucleic acid sequence as found in nature.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

To "control" insects means to inhibit, through a toxic effect, the ability of insect pests to survive, grow, feed, and/or reproduce, or to limit insect-related damage or loss in crop plants. To "control" insects may or may not mean killing the insects, although it preferably means killing the insects.

Corresponding to: in the context of the present invention, "corresponding to" means that when the amino acid sequences of variant Cry3A δ-endotoxins are aligned with each other, the amino acids that "correspond to" certain enumerated positions in the present invention are those that align with these positions in the Cry3A toxin (SEQ ID NO: 2), but that are not necessarily in these exact numerical positions relative to the particular Cry3A amino acid sequence of the invention. For example, the maize optimized cry3A gene (SEQ ID NO: 3) of the invention encodes a Cry3A toxin (SEQ ID NO: 4) that begins at Met-48 of the Cry3A toxin (SEQ ID NO: 2) encoded by the native cry3A gene (SEQ ID NO: 1). Therefore, according to the present invention, amino acid numbers 107–115, including all numbers in between, and 536–541, including all numbers in between, of SEQ ID NO: 4 correspond to amino acid numbers 154–163, and all numbers in between, and 583–588, and all numbers in between, respectively, of SEQ ID NO: 2.

A "Cry3A toxin", as used herein, refers to an approximately 73 kDa *Bacillus thuringiensis* var. *tenebrionis* (Kreig et al., 1983, Z. Angew. Entomol. 96:500–508) (Bt) coleopteran-active protein (Sekar et al., 1987, Proc. Nalt. Acad. Sci. 84:7036–7040), for example SEQ ID NO: 2, as well as any truncated lower molecular weight variants, derivable from a Cry3A toxin, for example SEQ ID NO: 4, and retaining substantially the same toxicity as the Cry3A toxin. The lower molecular weight variants can be obtained by protease cleavage of naturally occurring protease recognition sites of the Cry3A toxin or by a second translational initiation codon in the same frame as the translational initiation codon coding for the 73 kDa Cry3A toxin. The amino acid sequence of a Cry3A toxin and the lower molecular weight variants thereof can be found in a toxin naturally occurring in Bt. A Cry3A toxin can be encoded by a native Bt gene as in SEQ ID NO: 1 or by a synthetic coding sequence as in SEQ ID NO: 3. A "Cry3A toxin" does not have any additional protease recognition sites over the protease recognition sites that naturally occur in the Cry3A toxin. A Cry3A toxin can be isolated, purified or expressed in a heterologous system.

A "cry3A gene", as used herein, refers to the nucleotide sequence of SEQ ID NO: 1 or SEQ ID NO: 3. A cry3A gene (Sekar et al., 1987, Proc. Natl. Acad. Sci. 84:7036–7040) can be naturally occurring, as found in *Bacillus thuringiensis* var. *tenebrionis* (Kreig et al., 1983, Z. Angew. Entomol. 96:500–508), or synthetic and encodes a Cry3A toxin. The cry3A gene of this invention can be referred to as the native cry3A gene as in SEQ ID NO: 1 or the maize-optimized cry3A gene as in SEQ ID NO: 3.

To "deliver" a toxin means that the toxin comes in contact with an insect, resulting in toxic effect and control of the insect. The toxin can be delivered in many recognized ways, e.g., orally by ingestion by the insect or by contact with the insect via transgenic plant expression, formulated protein composition(s), sprayable protein composition(s), a bait matrix, or any other art-recognized toxin delivery system.

"Effective insect-controlling amount" means that concentration of toxin that inhibits, through a toxic effect, the ability of insects to survive, grow, feed and/or reproduce, or to limit insect-related damage or loss in crop plants. "Effective insect-controlling amount" may or may not mean killing the insects, although it preferably means killing the insects.

"Expression cassette" as used herein means a nucleic acid sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

A "gut protease" is a protease naturally found in the digestive tract of an insect. This protease is usually involved in the digestion of ingested proteins.

A "heterologous" nucleic acid sequence is a nucleic acid sequence not naturally associated with a host cell into which it is introduced, including non-naturally occurring multiple copies of a naturally occurring nucleic acid sequence.

A "homologous" nucleic acid sequence is a nucleic acid sequence naturally associated with a host cell into which it is introduced.

"Homologous recombination" is the reciprocal exchange of nucleic acid fragments between homologous nucleic acid molecules.

"Insecticidal" is defined as a toxic biological activity capable of controlling insects, preferably by killing them.

A nucleic acid sequence is "isocoding with" a reference nucleic acid sequence when the nucleic acid sequence encodes a polypeptide having the same amino acid sequence as the polypeptide encoded by the reference nucleic acid sequence.

An "isolated" nucleic acid molecule or an isolated toxin is a nucleic acid molecule or toxin that, by the hand of man, exists apart from its native environment and is therefore not a product of nature. An isolated nucleic acid molecule or toxin may exist in a purified form or may exist in a non-native environment such as, for example, a recombinant host cell.

A "modified Cry3A toxin" of this invention, refers to a Cry3A-derived toxin having at least one additional protease recognition site that is recognized by a gut protease of a target insect, which does not naturally occur in a Cry3A toxin. A modified Cry3A toxin is not naturally occurring and, by the hand of man, comprises an amino acid sequence that is not identical to a naturally occurring toxin found in *Bacillus thuringiensis*. The modified Cry3A toxin causes higher mortality to a target insect than the mortality caused by a Cry3A toxin to the same target insect.

A "modified cry3A gene" according to this invention, refers to a cry3A-derived gene comprising the coding sequence of at least one additional protease recognition site that does not naturally occur in an unmodified cry3A gene. The modified cry3A gene can be derived from a native cry3A gene or from a synthetic cry3A gene.

A "naturally occurring protease recognition site" is a location within a Cry3A toxin that is cleaved by a non-insect derived protease or by a protease or gut extract from an insect species susceptible to the Cry3A toxin. For example, a naturally occurring protease recognition site, recognized by trypsin and proteases found in a susceptible insect gut extract, exists between Arg-158 and Asn-159 of the deduced Cry3A toxin amino acid sequence (SEQ ID NO: 2). Naturally occurring protease recognition sites, recognized by chymotrypsin, exist between His-161 and Ser-162 as well as between Tyr-587 and Tyr-588 of the deduced Cry3A toxin amino acid sequence (SEQ ID NO: 2).

A "nucleic acid molecule" or "nucleic acid sequence" is a linear segment of single- or double-stranded DNA or RNA that can be isolated from any source. In the context of the present invention, the nucleic acid molecule is preferably a segment of DNA.

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "promoter" is an untranslated DNA sequence upstream of the coding region that contains the binding site for RNA polymerase and initiates transcription of the DNA. The promoter region may also include other elements that act as regulators of gene expression.

A "protoplast" is an isolated plant cell without a cell wall or with only parts of the cell wall.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

"Replaces" a naturally occurring protease recognition site—According to the present invention, an additional protease recognition site "replaces" a naturally occurring protease recognition site when insertion of the additional protease recognition site eliminates the naturally occurring protease recognition site. For example, an additional protease recognition site inserted between Pro-154 and Pro-160 of the deduced amino acid sequence of a Cry3A toxin (SEQ ID NO: 2) which eliminates the Arg-158 and Asn-159 residues "replaces" the naturally occurring trypsin recognition site located between Arg-158 and Asn-159 of the deduced amino acid sequence of the Cry3A toxin (SEQ ID NO: 2).

"Serine proteases", describe the same group of enzymes that catalyze the hydrolysis of covalent peptidic bonds using a mechanism based on nucleophilic attack of the targeted peptidic bond by a serine. Serine proteases are sequence specific. That is, each serine protease recognizes a specific sub-sequence within a protein where enzymatic recognition occurs.

A "target insect" is an insect pest species that has little or no susceptibility to a Cry3A toxin and is identified as being a candidate for using the technology of the present invention to control. This control can be achieved through several means but most preferably through the expression of the nucleic acid molecules of the invention in transgenic plants.

A "target insect gut protease" is a protease found in the gut of a target insect whose recognition site can be inserted into a Cry3A toxin to create a modified Cry3A toxin of the invention.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

"Within" a naturally occurring protease recognition site—According to the present invention, an additional protease recognition site is "within" a naturally occurring protease recognition site when the additional protease recognition site lies between the amino acid residue that comes before and the amino acid residue that comes after the naturally occurring protease recognition site. For example, an additional protease recognition site inserted between Tyr-587 and Tyr-588 of the deduced amino acid sequence of a Cry3A toxin (SEQ ID NO: 2) is "within" a naturally occurring chymotrypsin recognition site located between Tyr-587 and Tyr-588 of the deduced amino acid sequence of the Cry3A toxin (SEQ ID NO: 2). The insertion of an additional protease recognition site within a naturally occurring protease recognition site may or may not change the recognition of the naturally occurring protease recognition site by a protease.

Nucleotides are indicated by their bases by the following standard abbreviations: adenine (A), cytosine (C), thymine (T), and guanine (G). Amino acids ate likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

DESCRIPTION

This invention relates to modified cry3A nucleic acid sequences whose expression results in modified Cry3A toxins, and to the making and using of the modified Cry3A toxins to control insect pests. The expression of the modified cry3A nucleic acid sequences results in modified Cry3A toxins that can be used to control coleopteran insects such as western corn rootworm and northern corn rootworm. A modified Cry3A toxin of the present invention comprises at least one additional protease recognition site that does not naturally occur in a Cry3A toxin. The additional protease recognition site, which is recognized by a gut protease of a target insect, is inserted at approximately the same position as a naturally occurring protease recognition site in a Cry3A toxin. The modified Cry3A toxin causes higher mortality to a target insect than the mortality caused by a Cry3A toxin to the same target insect. Preferably, the modified Cry3A toxin causes at least about 50% mortality to the target insect to which a Cry3A toxin causes up to about 30% mortality.

In one preferred embodiment, the invention encompasses an isolated nucleic acid molecule that encodes a modified Cry3A toxin, wherein the additional protease recognition site is recognized by the target insect gut protease, cathepsin G. Cathepsin G activity is determined to be present in the gut of the target insect, western corn rootworm, as described in Example 2. Preferably, the substrate amino acid sequence, AAPF (SEQ ID NO: 35), used to determine the presence of the cathepsin G activity is inserted into the Cry3A toxin according to the present invention. Other cathepsin G recognition sites can also be used according to the present invention, for example, AAPM (SEQ ID NO: 36), AVPF (SEQ ID NO: 37), PFLF (SEQ ID NO: 38) or other cathepsin G recognition sites as determined by the method of Tanaka et al., 1985 (Biochemistry 24:2040–2047), incorporated herein by reference. Protease recognition sites of other proteases identified in a target insect gut can be used, for example, protease recognition sites recognized by other serine proteases, cysteine proteases and aspartic proteases. Preferable serine proteases encompassed by this embodiment include trypsin, chymotrypsin, carboxypeptidase, endopeptidase and elastase.

In another preferred embodiment, the invention encompasses an isolated nucleic acid molecule that encodes a modified Cry3A toxin wherein the additional protease recognition site is inserted in either domain I or domain III or in both domain I and domain III of the Cry3A toxin. Preferably, the additional protease recognition site is inserted in domain I, domain III, or domain I and domain III at a position that replaces, is adjacent to, or is within a naturally occurring protease recognition site in the Cry3A toxin. Specifically exemplified herein are nucleic acid molecules that encode modified Cry3A toxins that comprise a cathepsin G recognition site inserted in domain I, domain III, or domain I and domain III at a position that replaces, is adjacent to, or is within a naturally occurring protease recognition site in the unmodified Cry3A toxin.

Specifically exemplified teachings of methods to make modified cry3A nucleic acid molecules that encode modified Cry3A toxins can be found in Example 3. Those skilled in the art will recognize that other methods known in the art can also be used to insert additional protease recognition sites into Cry3A toxins according to the present invention.

In another preferred embodiment, the invention encompasses an isolated nucleic acid molecule that encodes a modified Cry3A toxin wherein the additional protease recognition site is inserted in domain I between amino acids corresponding to amino acid numbers 154 and 162 of SEQ ID NO: 2. Preferably, the additional protease recognition site is inserted between amino acid numbers 154 and 162 of SEQ ID NO: 2 or between amino acid numbers 107 and 115 of SEQ ID NO: 4. In a preferred embodiment, the additional protease recognition site is inserted between amino acids corresponding to amino acid numbers 154 and 160 of SEQ ID NO: 2. Preferably, the additional protease recognition site is inserted between amino acid number 154 and 160 of SEQ ID NO: 2 or between amino acid numbers 107 and 113 of SEQ ID NO: 4. Specifically exemplified herein is a nucleic acid molecule, designated cry3A054 (SEQ ID NO: 6), that encodes the modified Cry3A054 toxin (SEQ ID NO: 7) comprising a cathepsin G recognition site inserted in domain I between amino acid numbers 107 and 113 of SEQ ID NO: 4. The cathepsin G recognition site replaces a naturally occurring trypsin recognition site and is adjacent to a naturally occurring chymotrypsin recognition site. When expressed in a heterologous host, the nucleic acid molecule of SEQ ID NO: 6 results in insect control activity against western corn rootworm and northern corn rootworm, showing that the nucleic acid sequence set forth in SEQ ID NO: 6 is sufficient for such insect control activity.

In another preferred embodiment, the additional protease recognition site is inserted in domain I between amino acids corresponding to amino acid numbers 154 and 158 of SEQ ID NO: 2. Preferably, the additional protease recognition site is inserted in domain I between amino acid numbers 154 and 158 of SEQ ID NO: 2 or between amino acid numbers 107 and 111 of SEQ ID NO: 4. Specifically exemplified herein are nucleic acid molecules, designated cry3A055 (SEQ ID NO: 8), that encodes the modified Cry3A055 toxin (SEQ ID NO: 9), and cry3A085 (SEQ ID NO: 10), that encodes the modified Cry3A085 toxin (SEQ ID NO: 1), comprising a cathepsin G recognition site inserted in domain I between amino acid numbers 107 and 111 of SEQ ID NO: 4. The cathepsin G recognition site is adjacent to naturally occurring trypsin and chymotrypsin recognition sites. When expressed in a heterologous host, the nucleic acid molecule of SEQ ID NO: 8 or SEQ ID NO: 10 results in insect control activity against western corn rootworm and northern corn rootworm, showing that the nucleic acid sequence set forth in SEQ ID NO: 8 or SEQ ID NO: 10 is sufficient for such insect control activity.

In a preferred embodiment, the invention encompasses an isolated nucleic acid molecule that encodes a modified Cry3A toxin wherein the additional protease recognition site is inserted in domain III between amino acids corresponding to amino acid numbers 583 and 589 of SEQ ID NO: 2. Preferably, the additional protease site is inserted in domain III between amino acid numbers 583 and 589 of SEQ ID NO: 2 or between amino acid numbers 536 and 542 of SEQ ID NO: 4.

In another preferred embodiment, the invention encompasses an isolated nucleic acid molecule that encodes a modified Cry3A toxin wherein the additional protease recognition site is inserted in domain III between amino acids corresponding to amino acid numbers 583 and 588 of SEQ ID NO: 2. Preferably, the additional protease site is inserted in domain III between amino acid numbers 583 and 588 of SEQ ID NO: 2 or between amino acid numbers 536 and 541 of SEQ ID NO: 4. Specifically exemplified herein is a nucleic acid molecule, designated cry3A082 (SEQ ID NO: 12), that encodes the modified Cry3A082 toxin (SEQ ID NO: 13) comprising a cathepsin G recognition site inserted in domain III between amino acid numbers 536 and 541 of SEQ ID NO: 4. The cathepsin G recognition site replaces a naturally occurring chymotrypsin recognition site. When expressed in a heterologous host, the nucleic acid molecule of SEQ ID NO: 12 results in insect control activity against western corn rootworm and northern corn rootworm, showing that the nucleic acid sequence set forth in SEQ ID NO: 12 is sufficient for such insect control activity.

In another preferred embodiment, the additional protease recognition site is inserted in domain III between amino acids corresponding to amino acid numbers 587 and 588 of SEQ ID NO: 2. Preferably, the additional protease site is inserted in domain III between amino acid numbers 587 and 588 of SEQ ID NO: 2 or between amino acid numbers 540 and 541 of SEQ ID NO: 4. Specifically exemplified herein is a nucleic acid molecule, designated cry3A058 (SEQ ID NO: 14), that encodes the modified Cry3A058 toxin (SEQ ID NO: 15) comprising a cathepsin G recognition site inserted in domain III between amino acid numbers 540 and 541 of SEQ ID NO: 4. The cathepsin G recognition site is within a naturally occurring chymotrypsin recognition site. When expressed in a heterologous host, the nucleic acid molecule of SEQ ID NO: 14 results in insect control activity against western corn rootworm and northern corn rootworm, showing that the nucleic acid sequence set forth in SEQ ID NO: 14 is sufficient for such insect control activity.

In yet another preferred embodiment, the invention encompasses an isolated nucleic acid molecule that encodes a modified Cry3A toxin wherein the additional protease recognition site is inserted in domain I between amino acids corresponding to amino acid numbers 154 and 160 and in domain III between amino acids corresponding to amino acid numbers 587 and 588 of SEQ ID NO: 2. Preferably, the additional protease recognition site is inserted in domain I between amino acid numbers 154 and 160 and in domain III between amino acid numbers 587 and 588 of SEQ ID NO: 2 or in domain I between amino acid numbers 107 and 113 and in domain III between amino acid numbers 540 and 541 of SEQ ID NO: 4. Specifically exemplified herein is a nucleic acid molecule, designated cry3A057 (SEQ ID NO: 16), that encodes the modified Cry3A057 toxin (SEQ ID NO: 17) comprising a cathepsin G recognition site inserted in domain I between amino acid numbers 107 and 113 and in domain III between amino acid numbers 540 and 541 of SEQ ID NO: 4. The cathepsin G recognition site replaces a naturally occurring trypsin recognition site and is adjacent to a naturally occurring chymotrypsin recognition site in domain I and is within a naturally occurring chymotrypsin recognition site in domain III. When expressed in a heterologous host, the nucleic acid molecule of SEQ ID NO: 16 results in insect control activity against western corn rootworm and northern corn rootworm, showing that the nucleic acid sequence set forth in SEQ ID NO: 16 is sufficient for such insect control activity.

In yet another preferred embodiment, the additional protease recognition site is located in domain I between amino acids corresponding to amino acid numbers 154 and 158 and in domain III between amino acids corresponding to amino acid numbers 587 and 588 of SEQ ID NO: 2. Preferably, the additional protease recognition site is inserted in domain I between amino acid numbers 154 and 158 and in domain III between amino acid numbers 587 and 588 of SEQ ID NO: 2 or in domain I between amino acid numbers 107 and 111 and in domain III between amino acid numbers 540 and 541 of SEQ ID NO: 4. Specifically exemplified herein is the nucleic acid molecule designated cry3A056 (SEQ ID NO: 18), which encodes the modified Cry3A056 toxin (SEQ ID NO: 19) comprising a cathepsin G recognition site inserted in domain I between amino acid numbers 107 and 111 and in domain III between amino acid numbers 540 and 541 of SEQ ID NO: 4. The cathepsin G recognition site is adjacent to naturally occurring trypsin and chymotrypsin recognition sites in domain I and is within a naturally occurring chymotrypsin recognition site in domain III. When expressed in a heterologous host, the nucleic acid molecule of SEQ ID NO: 18 results in insect control activity against western corn rootworm and northern corn rootworm, showing that the nucleic acid sequence set forth in SEQ ID NO: 18 is sufficient for such insect control activity.

In still another preferred embodiment, the additional protease recognition site is located in domain I between amino acids corresponding to amino acid numbers 154 and 158 and in domain III between amino acids corresponding to amino acid numbers 583 and 588 of SEQ ID NO: 2. Preferably, the additional protease recognition site is inserted in domain I between amino acid numbers 154 and 158 and in domain III between amino acid numbers 583 and 588 of SEQ ID NO: 2 or in domain I between amino acid numbers 107 and 111 and in domain III between amino acid numbers 536 and 541 of SEQ ID NO: 4. Specifically exemplified herein is a nucleic acid molecule, designated cry3A083 (SEQ ID NO: 20), which encodes the modified Cry3A083 toxin (SEQ ID NO: 21) comprising a cathepsin G recognition site inserted in domain I between amino acid numbers 107 and 111 and in domain III between amino acid numbers 536 and 541 of SEQ ID NO: 4. The cathepsin G recognition site is adjacent to naturally occurring trypsin and chymotrypsin recognition sites in domain I and replaces a naturally occurring chymotrypsin recognition site in domain III. When expressed in a heterologous host, the nucleic acid molecule of SEQ ID NO: 20 results in insect control activity against western corn rootworm and northern corn rootworm, showing that the nucleic acid sequence set forth in SEQ ID NO: 20 is sufficient for such insect control activity.

In a preferred embodiment, the isolated nucleic acid molecule of the present invention comprises nucleotides 1–1791 of SEQ ID NO: 6, nucleotides 1–1806 of SEQ ID NO: 8, nucleotides 1–1812 of SEQ ID NO: 10, nucleotides 1–1794 of SEQ ID NO: 12, nucleotides 1–1818 of SEQ ID NO: 14, nucleotides 1–1812 of SEQ ID NO: 16, nucleotides 1–1791 of SEQ ID NO: 18, and nucleotides 1–1818 of SEQ ID NO: 20.

In another preferred embodiment, the invention encompasses the isolated nucleic acid molecule that encodes a modified Cry3A toxin comprising the amino acid sequence set forth in SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21.

The present invention also encompasses recombinant vectors comprising the nucleic acid sequences of this invention. In such vectors, the nucleic acid sequences are preferably comprised in expression cassettes comprising regulatory elements for expression of the nucleotide sequences in a host cell capable of expressing the nucleotides sequences. Such regulatory elements usually comprise promoter and termination signals and preferably also comprise elements allowing efficient translation of polypeptides encoded by the nucleic acid sequences of the present invention. Vectors comprising the nucleic acid sequences are usually capable of replication in particular host cells, preferably as extrachromosomal molecules, and are therefore used to amplify the nucleic acid sequences of this invention in the host cells. In one embodiment, host cells for such vectors are microorganisms, such as bacteria, in particular *Bacillus thuringiensis* or *E. coli*. In another embodiment, host cells for such recombinant vectors are endophytes or epiphytes. A preferred host cell for such vectors is a eukaryotic cell, such as a plant cell. Plant cells such as maize cells are most preferred host cells. In another preferred embodiment, such vectors are viral vectors and are used for replication of the nucleotide sequences in particular host cells, e.g. insect cells or plant cells. Recombinant vectors are also used for transformation of the nucleotide sequences of this invention into host cells, whereby the nucleotide sequences are stably integrated into the DNA of such host cells. In one, such host cells are prokaryotic cells. In a preferred embodiment, such host cells are eukaryotic cells, such as plant cells. In a most preferred embodiment, the host cells are plant cells, such as maize cells.

In another aspect, the present invention encompasses modified Cry3A toxins produced by the expression of the nucleic acid molecules of the present invention.

In preferred embodiments, the modified Cry3A toxins of the invention comprise a polypeptide encoded by a nucleotide sequence of the invention. In a further preferred embodiment, the modified Cry3A toxin is produced by the expression of the nucleic acid molecule comprising nucleotides 1–1791 of SEQ ID NO: 6, nucleotides 1–1806 of SEQ ID NO: 8, nucleotides 1–1812 of SEQ ID NO: 10, nucleotides 1–1794 of SEQ ID NO: 12, nucleotides 1–1818 of SEQ ID NO: 14, nucleotides 1–1812 of SEQ ID NO: 16, nucleotides 1–1791 of SEQ ID NO: 18, and nucleotides 1–1818 of SEQ ID NO: 20.

In a preferred embodiment, a modified Cry3A toxin of the present invention comprises the amino acid sequence set forth in SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21.

The modified Cry3A toxins of the present invention have insect control activity when tested against insect pests in bioassays. In another preferred embodiment, the modified Cry3A toxins of the invention are active against coleopteran insects, preferably against western corn rootworm and northern corn rootworm. The insect controlling properties of the modified Cry3A toxins of the invention are further illustrated in Examples 4 and 6.

The present invention also encompasses a composition comprising an effective insect-controlling amount of a modified Cry3A toxin according to the invention.

In another preferred embodiment, the invention encompasses a method of producing a modified Cry3A toxin that is active against insects, comprising: (a) obtaining a host cell comprising a chimeric gene, which itself comprises a heterologous promoter sequence operatively linked to the nucleic acid molecule of the invention; and (b) expressing the nucleic acid molecule in the transgenic host cell, which results in at least one modified Cry3A toxin that is active against insects.

In a further preferred embodiment, the invention encompasses a method of producing an insect-resistant transgenic plant, comprising introducing a nucleic acid molecule of the invention into the transgenic plant, wherein the nucleic acid molecule is expressible in the transgenic plant in an effective amount to control insects. In a preferred embodiment, the insects are coleopteran insects, preferably western corn rootworm and northern corn rootworm.

In yet a further preferred embodiment, the invention encompasses a method of controlling insects, comprising delivering to the insects an effective amount of a modified Cry3A toxin of the invention. According to this embodiment, the insects are coleopteran insects, preferably, western corn rootworm and northern corn rootworm. Preferably, the modified Cry3A toxin is delivered to the insects orally. In one preferred aspect, the toxin is delivered orally through a transgenic plant comprising a nucleic acid sequence that expresses a modified Cry3A toxin of the present invention.

The present invention also encompasses a method of making a modified Cry3A toxin, comprising: (a) obtaining a cry3A toxin gene which encodes a Cry3A toxin; (b) identifying a gut protease of a target insect; (c) obtaining a nucleotide sequence which encodes a recognition site for the gut protease; (d) inserting the nucleotide sequence of (c) into either domain I or domain III or both domain I and domain III at a position that replaces, is within, or adjacent to a nucleotide sequence that codes for a naturally occurring protease recognition site in the cry3A toxin gene, thus creating a modified cry3A toxin gene; (e) inserting the modified cry3A toxin gene in an expression cassette; (f) expressing the modified cry3A toxin gene in a non-human host cell, resulting in the host cell producing a modified Cry3A toxin; and, (g) bioassaying the modified Cry3A toxin against a target insect, which causes higher mortality to the target insect than the mortality caused by a Cry3A toxin. In a preferred embodiment, the modified Cry3A toxin causes at least about 50% mortality to the target insect when the Cry3A toxin causes up to about 30% mortality.

The present invention further encompasses a method of controlling insects wherein the transgenic plant further comprises a second nucleic acid sequence or groups of nucleic acid sequences that encode a second pesticidal principle. Particularly preferred second nucleic acid sequences are those that encode a δ-endotoxin, those that encode a Vegetative Insecticidal Protein toxin, disclosed in U.S. Pat. Nos. 5,849,870 and 5,877,012, incorporated herein by reference, or those that encode a pathway for the production of a non-proteinaceous principle.

In further embodiments, the nucleotide sequences of the invention can be further modified by incorporation of random mutations in a technique known as in vitro recombination or DNA shuffling. This technique is described in Stemmer et al., Nature 370:389–391 (1994) and U.S. Pat. No. 5,605,793, which are incorporated herein by reference. Millions of mutant copies of a nucleotide sequence are produced based on an original nucleotide sequence of this invention and variants with improved properties, such as increased insecticidal activity, enhanced stability, or different specificity or ranges of target-insect pests are recovered. The method encompasses forming a mutagenized double-stranded polynucleotide from a template double-stranded polynucleotide comprising a nucleotide sequence of this invention, wherein the template double-stranded polynucleotide has been cleaved into double-stranded-random fragments of a desired size, and comprises the steps of adding to the resultant population of double-stranded random fragments one or more single or double-stranded oligonucleotides, wherein said oligonucleotides comprise an area of identity and an area of heterology to the double-stranded template polynucleotide; denaturing the resultant mixture of double-stranded random fragments and oligonucleotides into single-stranded fragments; incubating the resultant population of single-stranded fragments with a polymerase under conditions which result in the annealing of said single-stranded fragments at said areas of identity to form pairs of annealed fragments, said areas of identity being sufficient for one member of a pair to prime replication of the other, thereby forming a mutagenized double-stranded polynucleotide; and repeating the second and third steps for at least two further cycles, wherein the resultant mixture in the second step of a further cycle includes the mutagenized double-stranded polynucleotide from the third step of the previous cycle, and the further cycle forms a further mutagenized double-stranded polynucleotide. In a preferred embodiment, the concentration of a single species of double-stranded random fragment in the population of double-stranded random fragments is less than 1% by weight of the total DNA. In a further preferred embodiment, the template double-stranded polynucleotide comprises at least about 100 species of polynucleotides. In another preferred embodiment, the size of the double-stranded random fragments is from about 5 bp to 5 kb. In a further preferred embodiment, the fourth step of the method comprises repeating the second and the third steps for at least 10 cycles.

Expression of the Nucleotide Sequences in Heterologous Microbial Hosts

As biological insect control agents, the insecticidal modified Cry3A toxins are produced by expression of the nucleotide sequences in heterologous host cells capable of expressing the nucleotide sequences. In a first embodiment, *B. thuringiensis* cells comprising modifications of a nucleotide sequence of this invention are made. Such modifications encompass mutations or deletions of existing regulatory elements, thus leading to altered expression of the nucleotide sequence, or the incorporation of new regulatory elements controlling the expression of the nucleotide sequence. In another embodiment, additional copies of one or more of the nucleotide sequences are added to *Bacillus thuringiensis* cells either by insertion into the chromosome or by introduction of extrachromosomally replicating molecules containing the nucleotide sequences.

In another embodiment, at least one of the nucleotide sequences of the invention is inserted into an appropriate expression cassette, comprising a promoter and termination signal. Expression of the nucleotide sequence is constitutive, or an inducible promoter responding to various types of stimuli to initiate transcription is used. In a preferred embodiment, the cell in which the toxin is expressed is a microorganism, such as a virus, bacteria, or a fungus. In a preferred embodiment, a virus, such as a baculovirus, contains a nucleotide sequence of the invention in its genome and expresses large amounts of the corresponding insecticidal toxin after infection of appropriate eukaryotic cells that are suitable for virus replication and expression of the nucleotide sequence. The insecticidal toxin thus produced is used as an insecticidal agent. Alternatively, baculoviruses engineered to include the nucleotide sequence are used to infect insects in vivo and kill them either by expression of the insecticidal toxin or by a combination of viral infection and expression of the insecticidal toxin.

Bacterial cells are also hosts for the expression of the nucleotide sequences of the invention. In a preferred embodiment, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera *Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces* and *Xanthomonas*. Symbiotic fungi, such as *Trichoderma* and *Gliocladium* are also possible hosts for expression of the inventive nucleotide sequences for the same purpose.

Techniques for these genetic manipulations are specific for the different available hosts and are known in the art. For example, the expression vectors pKK223-3 and pKK223-2 can be used to express heterologous genes in *E. coli*, either in transcriptional or translational fusion, behind the tac or trc promoter. For the expression of operons encoding multiple ORFs, the simplest procedure is to insert the operon into a vector such as pKK223-3 in transcriptional fusion, allowing the cognate ribosome binding site of the heterologous genes to be used. Techniques for overexpression in gram-positive species such as Bacillus are also known in the art and can be used in the context of this invention (Quax et al. In: Industrial Microorganisms:Basic and Applied Molecular Genetics, Eds. Baltz et al., American Society for Microbiology, Washington (1993)). Alternate systems for overexpression rely for example, on yeast vectors and include the use of Pichia, Saccharomyces and Kluyveromyces (Sreekrishna, In: Industrial microorganisms:basic and applied molecular genetics, Baltz, Hegeman, and Skatrud eds., American Society for Microbiology, Washington (1993); Dequin & Barre, Biotechnology L2:173–177 (1994); van den Berg et al., Biotechnology 8:135–139 (1990)).

Plant Transformation

In a particularly preferred embodiment, at least one of the insecticidal modified Cry3A toxins of the invention is expressed in a higher organism, e.g., a plant. In this case, transgenic plants expressing effective amounts of the modified Cry3A toxins protect themselves from insect pests. When the insect starts feeding on such a transgenic plant, it also ingests the expressed modified Cry3A toxins. This will deter the insect from further biting into the plant tissue or may even harm or kill the insect. A nucleotide sequence of the present invention is inserted into an expression cassette, which is then preferably stably integrated in the genome of said plant. In another preferred embodiment, the nucleotide sequence is included in a non-pathogenic self-replicating virus. Plants transformed in accordance with the present invention may be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar beet, sunflower, rapeseed, clover, tobacco, carrot, cotton, alfalfa, rice, potato, eggplant, cucumber, Arabidopsis, and woody plants such as coniferous and deciduous trees.

Once a desired nucleotide sequence has been transformed into a particular plant species, it may be propagated in that species or moved into other varieties of the same species, particularly including commercial varieties, using traditional breeding techniques.

A nucleotide sequence of this invention is preferably expressed in transgenic plants, thus causing the biosynthesis of the corresponding modified Cry3A toxin in the transgenic plants. In this way, transgenic plants with enhanced resistance to insects are generated. For their expression in transgenic plants, the nucleotide sequences of the invention may require other modifications and optimization. Although in many cases genes from microbial organisms can be expressed in plants at high levels without modification, low expression in transgenic plants may result from microbial nucleotide sequences having codons that are not preferred in plants. It is known in the art that all organisms have specific preferences for codon usage, and the codons of the nucleotide sequences described in this invention can be changed to conform with plant preferences, while maintaining the amino acids encoded thereby. Furthermore, high expression in plants is best achieved from coding sequences that have at least about 35% GC content, preferably more than about 45%, more preferably more than about 50%, and most preferably more than about 60%. Microbial nucleotide sequences that have low GC contents may express poorly in plants due to the existence of ATTTA motifs that may destabilize messages, and AATAAA motifs that may cause inappropriate polyadenylation. Although preferred gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477–498 (1989)). In addition, the nucleotide sequences are screened for the existence of illegitimate splice sites that may cause message truncation. All changes required to be made within the nucleotide sequences such as those described above are made using well known techniques of site directed mutagenesis, PCR, and synthetic gene construction using the methods described in the published patent applications EP 0 385 962 (to Monsanto), EP 0 359 472 (to Lubrizol, and WO 93/07278 (to Ciba-Geigy).

In one embodiment of the invention a cry3A gene is made according to the procedure disclosed in U.S. Pat. No. 5,625,136, herein incorporated by reference. In this procedure, maize preferred codons, i.e., the single codon that most frequently encodes that amino acid in maize, are used. The maize preferred codon for a particular amino acid might be derived, for example, from known gene sequences from maize. Maize codon usage for 28 genes from maize plants is found in Murray et al., Nucleic Acids Research 17:477–498 (1989), the disclosure of which is incorporated herein by reference. A synthetic sequence made with maize optimized codons is set forth in SEQ ID NO: 3.

In this manner, the nucleotide sequences can be optimized for expression in any plant. It is recognized that all or any part of the gene sequence may be optimized or synthetic. That is, synthetic or partially optimized sequences may also be used.

For efficient initiation of translation, sequences adjacent to the initiating methionine may require modification. For example, they can be modified by the inclusion of sequences known to be effective in plants. Joshi has suggested an appropriate consensus for plants (NAR 15:6643–6653 (1987)) and Clonetech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (whilst leaving the second amino acid unmodified), or alternatively up to and including the GTC subsequent to the ATG (with the possibility of modifying the second amino acid of the transgene).

Expression of the nucleotide sequences in transgenic plants is driven by promoters that function in plants. The choice of promoter will vary depending on the temporal and spatial requirements for expression, and also depending on the target species. Thus, expression of the nucleotide sequences of this invention in leaves, in stalks or stems, in ears, in inflorescences (e.g. spikes, panicles, cobs, etc.), in roots, and/or seedlings is preferred. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

Preferred promoters that are expressed constitutively include promoters from genes encoding actin or ubiquitin and the CaMV 35S and 19S promoters. The nucleotide sequences of this invention can also be expressed under the regulation of promoters that are chemically regulated. This enables the insecticidal modified Cry3A toxins to be synthesized only when the crop plants are treated with the inducing chemicals. Preferred technology for chemical induction of gene expression is detailed in the published application EP 0 332 104 (to Ciba-Geigy) and U.S. Pat. No. 5,614,395. A preferred promoter for chemical induction is the tobacco PR-1a promoter.

A preferred category of promoters is that which is wound inducible. Numerous promoters have been described which are expressed at wound sites and also at the sites of phytopathogen infection. Ideally, such a promoter should only be active locally at the sites of infection, and in this way the insecticidal modified Cry3A toxins only accumulate in cells that need to synthesize the insecticidal modified Cry3A toxins to kill the invading insect pest. Preferred promoters of this kind include those described by Stanford et al. Mol. Gen. Genet. 215:200–208 (1989), Xu et al. Plant Molec. Biol. 22:573–588 (1993), Logemann et al. Plant Cell 1:151–158 (1989), Rohrmeier & Lehle, Plant Molec. Biol. 22:783–792 (1993), Firek et al. Plant Molec. Biol. 22:129–142 (1993), and Warner et al. Plant J. 3:191–201 (1993).

Tissue-specific or tissue-preferential promoters useful for the expression of the modified Cry3A toxin genes in plants, particularly maize, are those which direct expression in root, pith, leaf or pollen, particularly root. Such promoters, e.g. those isolated from PEPC or trpA, are disclosed in U.S. Pat. No. 5,625,136, or MTL, disclosed in U.S. Pat. No. 5,466,785. Both U.S. patents are herein incorporated by reference in their entirety.

Further preferred embodiments are transgenic plants expressing the nucleotide sequences in a wound-inducible or pathogen infection-inducible manner.

In addition to promoters, a variety of transcriptional terminators are also available for use in chimeric gene construction using the modified Cry3A toxin genes of the present invention. Transcriptional terminators are responsible for the termination of transcription beyond the transgene and its correct polyadenylation. Appropriate transcriptional terminators and those that are known to function in plants include the CaMV 35S terminator, the tml terminator, the nopaline synthase terminator, the pea rbcS E9 terminator and others known in the art. These can be used in both monocotyledons and dicotyledons. Any available terminator known to function in plants can be used in the context of this invention.

Numerous other sequences can be incorporated into expression cassettes described in this invention. These include sequences that have been shown to enhance expression such as intron sequences (e.g. from Adhl and bronzel) and viral leader sequences (e.g. from TMV, MCMV and AMV).

It may be preferable to target expression of the nucleotide sequences of the present invention to different cellular localizations in the plant. In some cases, localization in the cytosol may be desirable, whereas in other cases, localization in some subcellular organelle may be preferred. Subcellular localization of transgene-encoded enzymes is undertaken using techniques well known in the art. Typically, the DNA encoding the target peptide from a known organelle-targeted gene product is manipulated and fused upstream of the nucleotide sequence. Many such target sequences are known for the chloroplast and their functioning in heterologous constructions has been shown. The expression of the nucleotide sequences of the present invention is also targeted to the endoplasmic reticulum or to the vacuoles of the host cells. Techniques to achieve this are well known in the art.

Vectors suitable for plant transformation are described elsewhere in this specification. For *Agrobacterium*-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. Biotechnology 4:1093–1096 (1986)). For both direct gene transfer and *Agrobacterium*-mediated transfer, transformation is usually (but not necessarily) undertaken with a selectable marker that may provide resistance to an antibiotic (kanamycin, hygromycin or methotrexate) or a herbicide (basta). Plant transformation vectors comprising the modified Cry3A toxin genes of the present invention may also comprise genes (e.g. phosphomannose isomerase; PMI) which provide for positive selection of the transgenic plants as disclosed in U.S. Pat. Nos. 5,767,378 and 5,994,629, herein incorporated by reference. The choice of selectable marker is not, however, critical to the invention.

In another embodiment, a nucleotide sequence of the present invention is directly transformed into the plastid genome. A major advantage of plastid transformation is that plastids are generally capable of expressing bacterial genes without substantial codon optimization, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) Proc. Nati. Acad. Sci. USA 91, 7301–7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Nati. Acad. Sci. USA 87, 8526–8530; Staub, J. M., and Maliga, P. (1992) Plant Cell 4, 39–45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601–606). Substantial increases in transformation frequency are obtained by replacement of the recessive rRNA or r-protein antibiotic resistance genes with a dominant selectable marker, the bacterial aadA gene encoding the spectinomycin-cletoxifying enzyme aminoglycoside-3'-adenyltransferase (Svab, Z., and Maliga, P. (1993) Proc. Natl. Acad. Sci. USA 90, 913–917). Previously, this marker had been used successfully for high-frequency transformation of the plastid genome of the green alga *Chlamydomonas reinhardtii* (Goldschmidt-Clermont, M. (1991) Nucl. Acids Res. 19:4083–4089). Other selectable markers useful for plastid transformation are known in the art and encompassed within the scope of the invention. Typically, approximately 15–20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid-targeting vector and transformed into the plastid genome of a desired plant host. Plants homoplastic for plastid genomes containing a nucleotide sequence of the present invention are obtained, and are preferentially capable of high expression of the nucleotide sequence.

Combinations of Insect Control Principles

The modified Cry3A toxins of the invention can be used in combination with Bt δ-endotoxins or other pesticidal principles to increase pest target range. Furthermore, the use of the modified Cry3A toxins of the invention in combination with Bt δ-endotoxins or other pesticidal principles of a distinct nature has particular utility for the prevention and/or management of insect resistance.

Other insecticidal principles include, for example, lectins, α-amylase, peroxidase and cholesterol oxidase. Vegetative Insecticidal Protein genes, such as vip1A(a) and vip2A(a) as disclosed in U.S. Pat. No. 5,889,174 and herein incorporated by reference, are also useful in the present invention.

This co-expression of more than one insecticidal principle in the same transgenic plant can be achieved by genetically engineering a plant to contain and express all the genes necessary. Alternatively, a plant, Parent 1, can be genetically engineered for the expression of genes of the present invention. A second plant, Parent 2, can be genetically engineered for the expression of a supplemental insect control principle. By crossing Parent 1 with Parent 2, progeny plants are obtained which express all the genes introduced into Parents 1 and 2.

Transgenic seed of the present invention can also be treated with an insecticidal seed coating as described in U.S. Pat. Nos. 5,849,320 and 5,876,739, herein incorporated by reference. Where both the insecticidal seed coating and the transgenic seed of the invention are active against the same target insect, the combination is useful (i) in a method for enhancing activity of a modified Cry3A toxin of the invention against the target insect and (ii) in a method for preventing development of resistance to a modified Cry3A toxin of the invention by providing a second mechanism of action against the target insect. Thus, the invention provides a method of enhancing activity against or preventing development of resistance in a target insect, for example corn rootworm, comprising applying an insecticidal seed coating to a transgenic seed comprising one or more modified Cry3A toxins of the invention.

Even where the insecticidal seed coating is active against a different insect, the insecticidal seed coating is useful to expand the range of insect control, for example by adding an insecticidal seed coating that has activity against lepidopteran insects to the transgenic seed of the invention, which has activity against coleopteran insects, the coated transgenic seed produced controls both lepidopteran and coleopteran insect pests.

EXAMPLES

The invention will be further described by reference to the following detailed examples. These examples are provided for the purposes of illustration only, and are not intended to be limiting unless otherwise specified. Standard recombinant DNA and molecular cloning techniques used here are well known in the art and are described by J. Sambrook, et al., Molecular Cloning: *A Laboratory Manual, 3d Ed.,* Cold Spring Harbor, N.Y.: Cold Spring Harbor Laboratory Press (2001); by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, New York, John Wiley and Sons Inc., (1988), Reiter, et al., *Methods in Arabidopsis Research*, World Scientific Press (1992), and Schultz et al., *Plant Molecular Biology Manual*, Kluwer Academic Publishers (1998).

Example 1

Maize Optimized cry3A Gene Construction

The maize optimized cry3A gene was made according to the procedure disclosed in U.S. Pat. No. 5,625,136, herein incorporated by reference in its entirety. In this procedure, maize preferred codons, i.e., the single codon that most frequently encodes that amino acid in maize, is used. The maize preferred codon for a particular amino acid is derived from known gene sequences from maize. Maize codon usage for 28 genes from maize plants is found in Murray et al., Nucleic Acids Research 17:477–498 (1989). The synthetic cry3A sequence made with maize optimized codons is set forth in SEQ ID NO: 3.

Example 2

Identification of Cathepsin-G Enzymatic Activity in Western Corn Rootworm Guts

Cathepsin G-like (serine protease) and cathepsin B-like (cysteine protease) enzymatic activities in western corn rootworm guts were measured using colorimetric substrates. Each 1 ml reaction contained about five homogenized midguts of the 3rd instar of western corn rootworm and approximately 1 mg of substrate dissolved in reaction buffer (10 mM Tris, 5 mM NaCl, 0.01 M DTT, pH 7.5). The cathepsin G substrate tested was Ala-Ala-Pro-Phe (SEQ ID NO: 35)-pNA and cathepsin B substrate, Arg-Arg-pNA. The reactions were incubated at approximately 28° C. for 1 hr. The intensity of yellow color formation, indicative of the efficiency of a protease to recognize the appropriate substrate, was compared in treatments vs. controls. The reactions were scored as negative (−) if no color or slight background color was detected. Reactions which were 25%, 50%, 75% or 100% above background were scored as +, ++, +++, or ++++, respectively. Results of the enzymatic assays are shown in the table 1.

TABLE 1

Results of Western Corn Rootworm Gut Protease Assay.

| Reaction | Product Color intensity |
| --- | --- |
| WCR gut only | − |
| Cathepsin B substrate only | − |
| Cathepsin G substrate only | − |
| WCR gut + Cathepsin B substrate | + |
| WCR gut + Cathepsin G substrate | +++ |

This is the first time that the serine protease cathepsin G activity has been identified in western corn rootworm guts. Western corn rootworm guts clearly have stronger cathepsin G, the serine protease, activity compared to cathepsin B, the cysteine protease, activity. The AAPF sequence (SEQ ID NO: 35) was selected as the cathepsin G protease recognition site for creating modified Cry3A toxins of the present invention.

Example 3

Construction of Modified cry3A Genes

Modified cry3A genes comprising a nucleotide sequence that encodes the cathepsin G recognition site in domain I, domain III, or domain I and domain III were made using overlap PCR. The maize optimized cry3A gene (SEQ ID NO: 2), comprised in plasmid pCIB6850 (SEQ ID NO: 5), was used as the starting template. Eight modified cry3A gene constructs, which encode modified Cry3A toxins, were made; cry3A054, cry3A055, and cry3A085, which comprise the cathepsin G recognition site coding sequence in domain I; cry3A058, cry3A082, which comprise the cathepsin G recognition site coding sequence in domain III; cry3A056, cry3A057, cry3A083, which comprise the cathepsin G recognition site coding sequence in domain I and domain III. The eight modified cry3A genes and the modified Cry3A toxins they encode are described as follows:

cry3A054 Comprised in pCMS054 cry3A054 (SEQ ID NO: 6) comprises a nucleotide sequence encoding a modified Cry3A toxin. Three overlap PCR primer pairs were used to insert the nucleotide sequence encoding the cathepsin G recognition site into the maize optimized cry3A gene:

```
                                            (SEQ ID NO:22)
1. BamExt1-5'-GGATCCACCATGACGGCCGAC-3'
                                            (SEQ ID NO:23)
   AAPFtail3-5'-GAACGGTGCAGCGGGGTTCTTCTGCCAGC-3'

(SEQ ID NO:24)
2. Tail5mod-5'-GCTGCACCGTTCCCCCACAGCCAGGGCCG-3'
                                            (SEQ ID NO:25)
   XbaIExt2-5'-TCTAGACCCACGTTGTACCAC-3'

(SEQ ID NO:22)
3. BamExt1-5'-GGATCCACCATGACGGCCGAC-3'
                                            (SEQ ID NO:25)
   XbaIExt2-5'-TCTAGACCCACGTTGTACCAC-3'
```

Primer pair 1 and primer pair 2 generated two unique PCR products. These products were then combined in equal parts and primer pair 3 was used to join the products to generate one PCR fragment that was cloned back into the original pCIB6850 template. The modified cry3A054 gene was then transferred to pBluescript (Stratagene). The resulting plasmid was designated pCMS054 and comprises the cry3A054 gene (SEQ ID NO: 6).

The modified Cry3A054 toxin (SEQ ID NO: 7), encoded by the modified cry3A gene comprised in pCMS054, has a cathepsin G recognition site, comprising the amino acid sequence AAPF (SEQ ID NO: 35), inserted in domain I between amino acids 107 and 113 of the Cry3A toxin set forth in SEQ ID NO: 4. The cathepsin G recognition site replaces the naturally occurring trypsin recognition site and is adjacent to a naturally occurring chymotrypsin recognition site.

cry3A055 Comprised in pCMS055 cry3A055 (SEQ ID NO: 8) comprises a nucleotide sequence encoding a modified Cry3A toxin. Three overlap PCR primer pairs were used to insert the nucleotide sequence encoding the cathepsin G recognition site into the maize optimized cry3A gene:

```
                                            (SEQ ID NO:22)
1. BamExt1-5'-GGATCCACCATGACGGCCGAC-3'
                                            (SEQ ID NO:23)
   AAPFtail3-5'-GAACGGTGCAGCGGGGTTCTTCTGCCAGC-3'

(SEQ ID NO:26)
2. AAPFtail4-5'-GCTGCACCGTTCCGCAACCCCCACAGCCA-3'
                                            (SEQ ID NO:25)
   XbaIExt2-5'-TCTAGACCCACGTTGTACCAC-3'

(SEQ ID NO:22)
3. BamExt1-5'-GGATCCACCATGACGGCCGAC-3'
                                            (SEQ ID NO:25)
   XbaIExt2-5'-TCTAGACCCACGTTGTACCAC-3'
```

Primer pair 1 and primer pair 2 generated two unique PCR products. These products were then combined in equal parts and primer pair 3 was used to join the products to generate one PCR fragment that was cloned back into the original pCIB6850 template. The modified cry3A055 gene was then transferred to pBluescript (Stratagene). The resulting plasmid was designated pCMS055 and comprises the cry3A055 gene (SEQ ID NO: 8).

The modified Cry3A055 toxin (SEQ ID NO: 9), encoded by the modified cry3A gene comprised in pCMS055, has a cathepsin G recognition site comprising the amino acid sequence AAPF (SEQ ID NO: 35) inserted in domain I between amino acids 107 and 111 of the Cry3A toxin set forth in SEQ ID NO: 4. The cathepsin G recognition site is adjacent to a natural trypsin and chymotrypsin recognition site.

cry3A058 Comprised in pCMS058 cry3A058 (SEQ ID NO: 14) comprises a nucleotide sequence encoding a modified Cry3A toxin. Three overlap PCR primer pairs were used to insert the nucleotide sequence encoding the cathepsin G recognition site into the maize optimized cry3A gene:

```
                                            (SEQ ID NO:27)
1. SalExt-5'-GAGCGTCGACTTCTTCAAC-3'
                                            (SEQ ID NO:28)
   AAPF-Y2-5'-GAACGGTGCAGCGTATTGGTTGAAGGGGGC-3'

(SEQ ID NO:29)
2. AAPF-Y1-5'-GCTGCACCGTTCTACTTCGACAAGACCATC-3'
                                            (SEQ ID NO:30)
   SacExt-5'-GAGCTCAGATCTAGTTCACGG-3'

(SEQ ID NO:27)
3. SalExt-5'-GAGCGTCGACTTCTTCAAC-3'
                                            (SEQ ID NO:30)
   SacExt-5'-GAGCTCAGATCTAGTTCACGG-3'
```

Primer pair 1 and primer pair 2 generated two unique PCR products. These products were then combined in equal parts and primer pair 3 was used to join the products to generate one PCR fragment that was cloned back into the original pCIB6850 template. The modified cry3A058 gene was then transferred to pBluescript (Stratagene). The resulting plasmid was designated pCMS058 and comprises the cry3A058 gene (SEQ ID NO: 14).

The modified Cry3A058 toxin (SEQ ID NO: 15), encoded by the modified cry3A gene, has a cathepsin G recognition site, comprising the amino acid sequence AAPF (SEQ ID NO: 35), inserted in domain III between amino acids 540 and 541 of the Cry3A toxin set forth in SEQ ID NO: 4. The cathepsin G recognition site is within a naturally occurring chymotrypsin recognition site.

pCMS082 Comprising cry3A082 cry3A082 (SEQ ID NO: 12) comprises a nucleotide sequence encoding a modified Cry3A toxin. A QuikChange Site Directed Mutagenesis PCR primer pair was used to insert the nucleotide sequence encoding the cathepsin G recognition site into the maize optimized cry3A gene:

```
                                            (SEQ ID NO:31)
   BBmod1-5'-CGGGGCCCCCGCTGCACCGTTCTACTTCGACA-3'

(SEQ ID NO:32)
   BBmod2-5'-TGTCGAAGTAGAACGGTGCAGCGGGGGCCCCG-3'
```

The primer pair generated a unique PCR product. This product was cloned back into the original pCIB6850 template. The modified cry3A082 gene was then transferred to pBluescript (Stratagene). The resulting plasmid was designated pCMS082 and comprises the cry3A082 gene (SEQ ID NO: 12).

The modified Cry3A082 toxin (SEQ ID NO: 13), encoded by the modified cry3A gene, has a cathepsin G recognition site, comprising the amino acid sequence AAPF (SEQ ID NO: 35), inserted in domain III between amino acids 539 and 542 of the Cry3A toxin set forth in SEQ ID NO: 4. The cathepsin G recognition site replaces a naturally occurring chymotrypsin recognition site.

cry3A056 Comprised in pCMS056 cry3A056 (SEQ ID NO: 18) comprises a nucleotide sequence encoding a modified Cry3A toxin. Six overlap PCR primer pairs were used to insert two cathepsin G recognition sites into the maize optimized cry3A gene:

```
                                            (SEQ ID NO:22)
1. BamExt1-5'-GGATCCACCATGACGGCCGAC-3'
                                            (SEQ ID NO:23)
   AAPFtail3-5'-GAACGGTGCAGCGGGGTTCTTCTGCCAGC-3'

(SEQ ID NO:26)
2. AAPFtail4-5'-GCTGCACCGTTCCGCAACCCCCACAGCCA-3'
                                            (SEQ ID NO:25)
   XbaIExt2-5'-TCTAGACCCACGTTGTACCAC-3'

(SEQ ID NO:22)
3. BamExt1-5'-GGATCCACCATGACGGCCGAC-3'
                                            (SEQ ID NO:25)
   XbaIExt2-5'-TCTAGACCCACGTTGTACCAC-3'

(SEQ ID NO:27)
4. SalExt-5'-GAGCGTCGACTTCTTCAAC-3'
                                            (SEQ ID NO:28)
   AAPF-Y2-5'-GAACGGTGCAGCGTATTGGTTGAAGGGGGC-3'

(SEQ ID NO:29)
5. AAPF-Y1-5'-GCTGCACCGTTCTACTTCGACAAGACCATC-3'
                                            (SEQ ID NO:30)
   SacExt-5'-GAGCTCAGATCTAGTTCACGG-3'

(SEQ ID NO:27)
6. SalExt-5'-GAGCGTCGACTTCTTCAAC-3'
                                            (SEQ ID NO:30)
   SacExt-5'-GAGCTCAGATCTAGTTCACGG-3'
```

Primer pair 1 and primer pair 2 generated two unique PCR products. These products were combined in equal parts and primer pair 3 is used to join the products to generate one PCR fragment that was cloned back into the original pCIB6850 plasmid. The modified cry3A055 gene was then transferred to pBluescript (Stratagene). The resulting plasmid was designated pCMS055. Primer pair 4 and primer pair 5 generated another unique set of fragments that were joined by another PCR with primer pair 6. This fragment was cloned into domain III of the modified cry3A055 gene comprised in pCMS055. The resulting plasmid was designated pCMS056 and comprises the cry3A056 gene (SEQ ID NO: 18).

The modified Cry3A056 toxin (SEQ ID NO: 19), encoded by the modified cry3A gene, has a cathepsin G recognition site, comprising the amino acid sequence AAPF (SEQ ID NO: 35), inserted in domain I between amino acids 107 and 111 and in domain III between amino acids 540 and 541 of the Cry3A toxin set forth in SEQ ID NO: 4. The cathepsin G recognition site is adjacent to a naturally occurring trypsin and chymotrypsin recognition site in domain I and is within a naturally occurring chymotrypsin recognition site in domain III.

cry3A057 Comprised in pCMS057 cry3A057 (SEQ ID NO: 16) comprises a nucleotide sequence encoding a modified Cry3A toxin. Six overlap PCR primer pairs are used to insert two cathepsin G recognition sites into the maize optimized cry3A gene:

```
                                            (SEQ ID NO:22)
1. BamExt1-5'-GGATCCACCATGACGGCCGAC-3'
                                            (SEQ ID NO:23)
   AAPFtail3-5'-GAACGGTGCAGCGGGGTTCTTCTGCCAGC-3'

(SEQ ID NO:24)
2. Tail5mod-5'-GCTGCACCGTTCCCCCACAGCCAGGGCCG-3'
                                            (SEQ ID NO:25)
   XbaIExt2-5'-TCTAGACCCACGTTGTACCAC-3'

(SEQ ID NO:22)
3. BamExt1-5'-GGATCCACCATGACGGCCGAC-3'
                                            (SEQ ID NO:25)
   XbaIExt2-5'-TCTAGACCCACGTTGTACCAC-3'

(SEQ ID NO:27)
4. SalExt-5'-GAGCGTCGACTTCTTCAAC-3'
                                            (SEQ ID NO:28)
   AAPF-Y2-5'-GAACGGTGCAGCGTATTGGTTGAAGGGGGC-3'

(SEQ ID NO:29)
5. AAPF-Y1-5'-GCTGCACCGTTCTACTTCGACAAGACCATC-3'
                                            (SEQ ID NO:30)
   SacExt-5'-GAGCTCAGATCTAGTTCACGG-3'

(SEQ ID NO:27)
6. SalExt-5'-GAGCGTCGACTTCTTCAAC-3'
                                            (SEQ ID NO:30)
   SacExt-5'-GAGCTCAGATCTAGTTCACGG-3'
```

Primer pair 1 and primer pair 2 generated two unique PCR products. These products were combined in equal parts and primer pair 3 was used to join the products to generate one PCR fragment that was cloned back into the original pCIB6850 plasmid. The modified cry3A054 gene was then transferred to pBluescript (Stratagene). The resulting plasmid was designated pCMS054. Primer pair 4 and primer pair 5 generated another unique set of fragments that were joined by another PCR with primer pair 6. This fragment was cloned into domain III of the modified cry3A054 gene comprised in pCMS054. The resulting plasmid was designated pCMS057 and comprises the cry3A057 gene (SEQ ID NO: 16).

The modified Cry3A057 toxin (SEQ ID NO: 17), encoded by the modified cry3A gene, has a cathepsin G recognition site, comprising the amino acid sequence AAPF (SEQ ID NO: 35), inserted in domain I between amino acids 107 and 113 and in domain III between amino acids 540 and 541 of the Cry3A toxin set forth in SEQ ID NO: 4. The cathepsin G recognition site replaces a naturally occurring trypsin recognition site and is adjacent to a naturally occurring chymotrypsin recognition site in domain I and is within a naturally occurring chymotrypsin recognition site in domain III.

cry3A083 Comprised in pCMS083 cry3A083 (SEQ ID NO: 20) comprises a nucleotide sequence encoding a modified Cry3A toxin. Three overlap PCR primer pairs and one QuikChange Site Directed Mutagenesis PCR primer pair were used to insert two cathepsin G recognition sites into the maize optimized cry3A gene:

```
                                            (SEQ ID NO:22)
1. BamExt1-5'-GGATCCACCATGACGGCCGAC-3'
                                            (SEQ ID NO:23)
   AAPFtail3-5'-GAACGGTGCAGCGGGGTTCTTCTGCCAGC-3'

(SEQ ID NO:26)
2. AAPFtail4-5'-GCTGCACCGTTCCGCAACCCCCACAGCCA-3'
                                            (SEQ ID NO:25)
   XbaIExt2-5'-TCTAGACCCACGTTGTACCAC-3'

(SEQ ID NO:22)
3. BamExt1-5'-GGATCCACCATGACGGCCGAC-3'
                                            (SEQ ID NO:25)
```

```
                    -continued
XbaIExt2-5'-TCTAGACCCACGTTGTACCAC-3'

(SEQ ID NO:31)
BBmod1-5'-CGGGGCCCCCGCTGCACCGTTCTACTTCGACA-3'
                                        (SEQ ID NO:32)
BBmod2-5'-TGTCGAAGTAGAACGGTGCAGCGGGGCCCCG-3'
```

Primer pair 1 and primer pair 2 generated two unique PCR products. These products were combined in equal parts and primer pair 3 was used to join the products to generate one PCR fragment that was cloned back into the original pCIB6850 plasmid. The modified cry3A055 gene was then transferred to pBluescript (Stratagene). The resulting plasmid was designated pCMS055. Primer pair 4 generated another unique fragment that was cloned into domain III of the modified cry3A comprised in pCMS055. The resulting plasmid was designated pCMS083 and comprises the cry3A083 gene (SEQ ID NO: 20).

The modified Cry3A083 toxin (SEQ ID NO: 21), encoded by the modified cry3A gene, has a cathepsin G recognition site, comprising the amino acid sequence AAPF (SEQ ID NO: 35), inserted in domain I between amino acids 107 and 111 and between amino acids 539 and 542 of the Cry3A toxin set forth in SEQ ID NO: 4. The cathepsin G recognition site is adjacent to a naturally occurring trypsin and chymotrypsin recognition site in domain I and replaces a naturally occurring chymotrypsin recognition site in domain III.

cry3A085 Comprised in pCMS085

The cry3A085 gene (SEQ ID NO: 10) comprises a cathepsin G coding sequence at the same position as in the cry3A055 gene described above. The cry3A085 gene has an additional 24 nucleotides inserted at the 5' end which encode amino acids 41–47 of the deduced amino acid sequence set forth in SEQ ID NO: 2 as well as an additional methionine. The additional nucleotides are inserted at the 5' end of the cry3A055 gene using the following PCR primer pair:

```
mo3Aext-5'-GGATCCACCATGAACTACAAGGAGTTCCTCCGCATGACCGCCGACAAC-3'    (SEQ ID NO:33)

CMS16-5'-CCTCCACCTGCTCCATGAAG-3'                                  (SEQ ID NO:34)
```

The modified Cry3A085 toxin (SEQ ID NO: 11), encoded by the modified cry3A gene, has a cathepsin G recognition site, comprising the amino acid sequence AAPF (SEQ ID NO: 35), inserted in domain I between amino acids corresponding to 107 and 111 of the Cry3A toxin set forth in SEQ ID NO: 4 and has an additional eight amino acid residues at the N-terminus of which the second residue corresponds to amino acid number 41 of the amino acid sequence set forth in SEQ ID NO: 2.

Example 4

Insecticidal Activity of Modified Cry3A Toxins

Modified Cry3A toxins were tested for insecticidal activity against western corn rootworm, northern corn rootworm and southern corn rootworm in insect bioassays. Bioassays were performed using a diet incorporation method. *E. coli* clones that express one of the modified Cry3A toxins of the invention were grown overnight. 500 μl of an overnight culture was sonicated and then mixed with 500 μl of molten artificial diet (Marrone et al. (1985) *J. of Economic Entomology* 78:290–293). The molten diet was dispensed into small petri dishes, allowed to solidify and then 20 neonate corn rootworm were placed on the diet. The petri dishes were held at approximately 30° C. Mortality was recorded after approximately 6 days. All of the modified Cry3A toxins cause 50%–100% mortality to western and northern corn rootworm whereas the unmodified Cry3A toxin causes 0%–30% mortality. The modified Cry3A toxins had no activity against southern corn rootworm.

Example 5

Creation of Transgenic Maize Plants Comprising Modified cry3A Coding Sequences

Three modified cry3A genes, cry3A055, representative of a domain I modification, cry3A058, representative of a domain III modification, and cry3A056, representative of a domain I and domain III modification, were chosen for transformation into maize plants. An expression cassette comprising a modified cry3A coding sequence is transferred to a suitable vector for *Agrobacterium*-mediated maize transformation. For this example, an expression cassette comprises, in addition to the modified cry3A gene, the MTL promoter (U.S. Pat. No. 5,466,785) and the nos terminater which is known in the art.

Transformation of immature maize embryos is performed essentially as described in Negrotto et al., 2000, Plant Cell Reports 19: 798–803. For this example, all media constituents are as described in Negrotto et al., supra. However, various media constituents known in the art may be substituted.

The genes used for transformation are cloned into a vector suitable for maize transformation. Vectors used in this example contain the phosphomannose isomerase (PMI) gene for selection of transgenic lines (Negrotto et al. (2000) Plant Cell Reports 19: 798–803).

*Agrobacterium* strain LBA4404 (pSBI) containing the plant transformation plasmid is grown on YEP (yeast extract (5 g/L), peptone (10 g/L), NaCl (5 g/L), 15 g/l agar, pH 6.8) solid medium for 2–4 days at 28° C. Approximately $0.8 \times 10^9$ *Agrobacterium* are suspended in LS-inf media supplemented with 100 μM As (Negrotto et al., (2000) Plant Cell Rep 19: 798–803). Bacteria are pre-induced in this medium for 30–60 minutes.

Immature embryos from A188 or other suitable genotype are excised from 8–12 day old ears into liquid LS-inf+100 μM As. Embryos are rinsed once with fresh infection medium. *Agrobacterium* solution is then added and embryos are vortexed for 30 seconds and allowed to settle with the bacteria for 5 minutes. The embryos are then transferred scutellum side up to LSAs medium and cultured in the dark for two to three days. Subsequently, between 20 and 25 embryos per petri plate are transferred to LSDc medium supplemented with cefotaxime (250 mg/l) and silver nitrate (1.6 mg/l) and cultured in the dark for 28° C. for 10 days.

Immature embryos, producing embryogenic callus are transferred to LSD1M0.5S medium. The cultures are selected on this medium for 6 weeks with a subculture step at 3 weeks. Surviving calli are transferred to Reg1 medium supplemented with mannose. Following culturing in the light (16 hour light/8 hour dark regiment), green tissues are then transferred to Reg2 medium without growth regulators and incubated for 1–2 weeks. Plantlets are transferred to Magenta GA-7 boxes (Magenta Corp, Chicago Ill.) containing Reg3 medium and grown in the light. After 2–3 weeks, plants are tested for the presence of the PMI genes and the modified cry3A genes by PCR. Positive plants from the PCR assay are transferred to the greenhouse and tested for resistance to corn rootworm.

Example 6

Analysis of Transgenic Maize Plants

Corn Rootworm Efficacy

Root Excision Bioassay

Plants are sampled as they are being transplanted from Magenta GA-7 boxes into soil. This allows the roots to be sampled from a reasonably sterile environment relative to soil conditions. Sampling consists of cutting a small piece of root (ca. 2–4 cm long) and placing it onto enriched phytagar (phytagar, 12 g., sucrose, 9 g., MS salts, 3 ml., MS vitamins, 3 ml., Nystatin(25 mg/ml), 3 ml., Cefotaxime (50 mg/ml), 7 ml., Aureomycin (50 mg/ml), 7 ml., Streptomycin (50 mg/ml), 7 ml., dH$_2$O, 600 ml) in a small petri-dish. Negative controls are either transgenic plants that are PCR negative for the modified cry3A gene from the same experiment, or from non-transgenic plants (of a similar size to test plants) that are being grown in the phytotron. If sampling control roots from soil, the root samples are washed with water to remove soil residue, dipped in Nystatin solution (5 mg/ml), removed from the dip, blotted dry with paper toweling, and placed into a phytagar dish.

Root samples are inoculated with western corn rootworms by placing 10 first instar larvae onto the inside surface of the lid of each phytagar dish and the lids then tightly resealed. Larvae are handled using a fine tip paintbrush. After all dishes are inoculated, the tray of dishes is placed in the dark at room temperature until data collection.

At 3–4 days post inoculation, data is collected. The percent mortality of the larvae is calculated along with a visual damage rating of the root. Feeding damage is rated as high, moderate, low, or absent and given a numerical value of 3, 2, 1 or 0, respectively. Root samples causing at least 40% mortality and having a damage rating of 2 or less are considered positive.

Results in the following table show that plants expressing a modified Cry3A toxin cause from 40–100% mortality to western corn rootworm whereas control plants cause 0–30% mortality. Also, plants expressing a modified Cry3A toxin sustain significantly less feeding damage than control plants.

TABLE 2

Results of Root Excision Bioassay.

| T0 Event | Modified Cry3A Toxin Expressed | Percent Mortality Per Plant | | | | | Mean Damage Rating Per Event |
|---|---|---|---|---|---|---|---|
| | | A | B | C | D | E | |
| 240A7 | Cry3A055 | 80 | 40 | 80 | 60 | | 0.8 |
| 240B2 | Cry3A055 | 60 | 60 | 60 | 80 | | 1.25 |
| 240B9 | Cry3A055 | 40 | 60 | 60 | 100 | | 1 |
| 240B10 | Cry3A055 | 80 | 40 | 60 | | | 1 |
| 240A15 | Cry3A055 | 80 | 60 | 50 | 70 | 70 | 0.6 |
| 240A5 | Cry3A055 | 60 | 80 | 60 | | | 0.33 |
| 240A9 | Cry3A055 | 50 | 60 | 60 | 70 | 70 | 1.6 |
| 244A4 | Cry3A058 | 50 | | | | | 1 |
| 244A7 | Cry3A058 | 40 | 40 | 60 | | | 1.3 |

TABLE 2-continued

Results of Root Excision Bioassay.

| T0 Event | Modified Cry3A Toxin Expressed | Percent Mortality Per Plant | | | | | Mean Damage Rating Per Event |
|---|---|---|---|---|---|---|---|
| | | A | B | C | D | E | |
| 244A5 | Cry3A058 | 50 | | | | | 1 |
| 244B7 | Cry3A058 | 90 | | | | | 1 |
| 244B6 | Cry3A058 | 50 | 40 | 60 | | | 1 |
| 243A3 | Cry3A056 | 50 | 90 | 80 | 60 | | 1.25 |
| 243A4 | Cry3A056 | 50 | 80 | 60 | | | 1.7 |
| 243B1 | Cry3A056 | 80 | 90 | | | | 0.5 |
| 243B4 | Cry3A056 | 70 | 60 | 50 | 80 | | 1.5 |
| 245B2 | Cry3A056 | 90 | 50 | 70 | 60 | | 1 |
| WT1 | — | 0 | 10 | 20 | 10 | 0 | 2.6 |
| WT2 | — | 0 | 30 | 0 | 0 | 20 | 2.8 |

Whole Plant Bioassay

Some positive plants identified using the root excision bioassay described above are evaluated for western corn rootworm resistance using a whole plant bioassay. Plants are infested generally within 3 days after the root excision assay is completed.

Western corn rootworm eggs are preincubated so that hatch occurs 2–3 days after plant inoculation. Eggs are suspended in 0.2% agar and applied to the soil around test plants at approximately 200 eggs/plant.

Two weeks after the eggs hatch, plants are evaluated for damage caused by western corn rootworm larvae. Plant height attained, lodging, and root mass are criteria used to determine if plants are resistant to western corn rootworm feeding damage. At the time of evaluation, control plants typically are smaller than modified Cry3A plants. Also, non-transgenic control plants and plants expressing the unmodified Cry3A toxin encoded by the maize optimized cry3A gene have lodged (stems loose in soil or stems at an angle of greater than 30° from vertical, including laying completely horizontal) during this time due to severe pruning (completely cut) of most of the roots resulting in no root mass accumulation. At the time of evaluation, plants expressing a modified Cry3A toxin of the invention are taller than control plants, have not lodged (stems remain tightly intact to soil and are vertical), and have a large intact root mass due to the insecticidal activity of the modified Cry3A toxin.

ELISA Assay

ELISA analysis according to the method disclosed in U.S. Pat. No. 5,625,136 is used for the quantitative determination of the level of modified and unmodified Cry3A protein in transgenic plants.

TABLE 3

Whole Plant Bioassay Results and Protein Levels

| Transgenic Maize Plant | Type of Cry3A Toxin Expressed | Cry3A Protein Level in Roots (ng/mg) | Plant Lodged[a] | Intact Root Mass[b] |
|---|---|---|---|---|
| 240A2E | modified Cry3A055 | 224 | − | + |
| 240A9C | modified Cry3A055 | 71 | − | + |
| 240B9D | modified Cry3A055 | 204 | − | + |
| 240B9E | modified Cry3A055 | 186 | − | + |
| 240B10D | modified Cry3A055 | 104 | − | + |
| 240B10E | modified Cry3A055 | 70 | − | + |
| 240A15E | modified Cry3A055 | 122 | − | + |

TABLE 3-continued

Whole Plant Bioassay Results and Protein Levels

| Transgenic Maize Plant | Type of Cry3A Toxin Expressed | Cry3A Protein Level in Roots (ng/mg) | Plant Lodged[a] | Intact Root Mass[b] |
|---|---|---|---|---|
| 240B4D | modified Cry3A055 | 97 | − | + |
| 243B5A | modified Cry3A056 | 41 | − | + |
| 244A7A | modified Cry3A058 | 191 | − | + |
| 710-2-51 | maize optimized | 39 | + | − |
| 710-2-54 | maize optimized | 857 | + | − |
| 710-2-61 | maize optimized | 241 | + | − |
| 710-2-67 | maize optimized | 1169 | + | − |
| 710-2-68 | maize optimized | 531 | + | − |
| 710-2-79 | maize optimized | 497 | + | − |
| 710-2-79 | maize optimized | 268 | + | − |
| WT1 Control | — | 0 | + | − |
| WT2 Control | — | 0 | + | − |

[a] A "−" indicates that the plant was standing vertical and therefore not lodged; a "+" indicates that the plant stem was greater than 30° from vertical, including laying completely horizontal.
[b] A "+" indicates that the plant had an intact root mass that was not pruned by corn rootworm feeding; a "−" indicates that the plant had little or no intact root mass due to severe pruning of the roots.

What is claimed is:

1. An isolated nucleic acid molecule comprising a nucleotide sequence that encodes a modified Cry3A toxin comprising a cathepsin G recognition site, wherein said cathepsin G recognition site modifies a Cry3A toxin and is located at a position between amino acids corresponding to amino acid numbers 107 and 115 of SEQ ID NO: 4, wherein said cathepsin G recognition site is recognizable by a gut protease of western corn rootworm, and wherein said modified Cry3A toxin causes higher mortality to western corn rootworm than the mortality caused by said Cry3A toxin to western corn rootworm in an artificial diet bioassay.

2. The isolated nucleic acid molecule according to claim 1, wherein said cathepsin G recognition site is located between amino acid numbers 107 and 115 of SEQ ID NO:4.

3. The isolated nucleic acid molecule according to claim 1, wherein said cathepsin G recognition site is located between amino acids corresponding to amino acid numbers 107 and 113 of SEQ ID NO:4.

4. The isolated nucleic acid molecule according to claim 3, wherein said cathepsin G recognition site is located between amino acid numbers 107 and 113 of SEQ ID NO:4.

5. The isolated nucleic acid molecule according to claim 1, wherein said cathepsin G recognition site is located between amino acids corresponding to amino acid numbers 107 and 111 of SEQ ID NO:4.

6. The isolated nucleic acid molecule according to claim 5, wherein said cathepsin G recognition site is located between amino acid numbers 107 and 111 of SEQ ID NO:4.

7. The isolated nucleic acid molecule according to claim 1, wherein said modified Cry3A toxin causes at least 50% mortality to western corn rootworm to which said Cry3A toxin causes up to 30% mortality.

8. The isolated nucleic acid molecule according to claim 1, wherein said nucleotide sequence comprises nucleotides 1–1791 of SEQ ID NO: 6, nucleotides 1–1806 of SEQ ID NO: 8, or nucleotides 1–1812 of SEQ ID NO: 10.

9. The isolated nucleic acid molecule according to claim 1, wherein said modified Cry3A toxin comprises the amino acid sequence set forth in SEQ ID NO: 7, SEQ ID NO: 9, or SEQ ID NO: 11.

10. The isolated nucleic acid molecule according to claim 1, wherein said modified Cry3A toxin is active against northern corn rootworm.

11. A chimeric construct comprising a heterologous promoter sequence operatively linked to the nucleic acid molecule of claim 1.

12. A recombinant vector comprising the chimeric construct of claim 11.

13. A transgenic non-human host cell comprising the chimeric construct of claim 11.

14. The transgenic host cell according to claim 13, which is a bacterial cell.

15. The transgenic host cell according to claim 13, which is a plant cell.

16. A transgenic plant comprising the transgenic plant cell of claim 15.

17. The transgenic plant according to claim 16, wherein said plant is a maize plant.

18. Transgenic seed from the transgenic plant of claim 16, wherein the seed comprises the nucleic acid molecule.

19. Transgenic seed from the maize plant of claim 17, wherein the seed comprises the nucleic acid molecule.

20. A transgenic maize plant comprising a nucleotide sequence that encodes a modified Cry3A toxin comprising a cathepsin G recognition site, wherein said cathepsin G recognition site modifies a Cry3A toxin and is located at a position between amino acids corresponding to amino acid numbers 107 and 115 of SEQ ID NO:4, wherein said cathepsin G recognition site is recognizable by a gut protease of western corn rootworm, and wherein said transgenic plant expresses said modified Cry3A toxin in root tissue at a level that causes mortality to western corn rootworm.

21. The transgenic maize plant according to claim 20, wherein said cathepsin G recognition site is located between amino acid numbers 107 and 111 of SEQ ID NO:4.

22. The transgenic maize plant according to claim 20, wherein said nucleotide sequence comprises nucleotides 1–1806 of SEQ ID NO: 8.

23. The transgenic maize plant according to claim 20, wherein said modified Cry3A toxin comprises the amino acid sequence set forth in SEQ ID NO: 9.

24. The transgenic maize plant according to claim 20, wherein said root tissue causes 100% mortality to western corn rootworm.

25. The transgenic maize plant according to claim 20, wherein said root tissue causes 90% mortality to western corn rootworm.

26. The transgenic maize plant according to claim 20, wherein said root tissue causes 80% mortality to western corn rootworm.

27. The transgenic maize plant according to claim 20, wherein said root tissue causes 70% mortality to western corn rootworm.

28. The transgenic maize plant according to claim 20, wherein said root tissue causes 60% mortality to western corn rootworm.

29. The transgenic maize plant according to claim 20, wherein said root tissue causes 50% mortality to western corn rootworm.

30. The transgenic maize plant according to claim 20, wherein said root tissue causes 40% mortality to western corn rootworm.

31. The transgenic maize plant according to claim 20, wherein said transgenic plant expresses said modified Cry3A toxin at a level sufficient to prevent western corn rootworm from severely pruning the roots of the transgenic plant.

32. The transgenic maize plant according to claim 20, wherein said transgenic plant expresses said modified Cry3A toxin at a level sufficient to prevent western corn rootworm feeding damage from causing the plant to lodge.

33. The transgenic maize plant according to claim 20, which is an inbred plant.

34. The transgenic maize plant according to claim 20, which is a hybrid plant.

35. Transgenic seed from the plant of claim 33, wherein the seed comprises the nucleotide sequence.

36. Transgenic seed from the plant of claim 34, wherein the seed comprises the nucleotide sequence.

37. A method of controlling infestation of maize plants by western corn rootworm, the method comprising:
  a) providing the transgenic maize plant according to claim 20; and
  b) contacting said western corn rootworm with the plant.

38. A method of producing a modified Cry3A toxin, comprising:
  a) obtaining the transgenic host cell according to claim 14;
  b) culturing the transgenic host cell under conditions that allow the expression of the modified Cry3A toxin; and
  c) recovering the expressed modified Cry3A toxin.

39. A method of producing insect-resistant plants, comprising:
  a) stably integrating the nucleic acid molecule according to claim 1 into the genome of plant cells; and
  b) regenerating stably transformed plants from said transformed plant cells, wherein said stably transformed plants express an effective amount of a modified Cry3A toxin to render said transformed plant resistant to at least western corn rootworm.

40. A modified cry3A gene comprising a nucleotide sequence that encodes a modified Cry3A toxin comprising a cathepsin G recognition site, wherein said modified cry3A gene comprises a coding sequence encoding said cathepsin G recognition site, wherein said coding sequence modifies a cry3A gene and is inserted at a position between the codons that code for amino acids corresponding to amino acid numbers 107 and 115 of SEQ ID NO:4, wherein said cathepsin G recognition site is recognizable by a gut protease of western corn rootworm, and wherein said modified Cry3A toxin causes higher mortality to western corn rootworm than the mortality caused by said Cry3A toxin to western corn rootworm in an artificial diet bioassay.

41. The modified cry3A gene according to claim 40, wherein said nucleotide sequence comprises nucleotides 1–1791 of SEQ ID NO: 6, nucleotides 1–1806 of SEQ ID NO: 8, or nucleotides 1–1812 of SEQ ID NO: 10.

42. The modified cry3A gene according to claim 40, wherein said modified Cry3A toxin comprises the amino acid sequence set forth in SEQ ID NO: 7, SEQ ID NO: 9, or SEQ ID NO: 11.

43. The modified cry3A gene according to claim 40, wherein said modified Cry3A toxin is active against northern corn rootworm.

44. A chimeric construct comprising a heterologous promoter sequence operatively linked to the modified cry3A gene of claim 40.

45. A recombinant vector comprising the chimeric construct of claim 44.

46. A transgenic non-human host cell comprising the chimeric construct of claim 44.

47. The transgenic host cell according to claim 46, which is a bacterial cell.

48. The transgenic host cell according to claim 46, which is a plant cell.

49. A transgenic plant comprising the transgenic plant cell of claim 48.

50. The transgenic plant according to claim 49, wherein said plant is a maize plant.

51. Transgenic seed from the transgenic plant of claim 49, wherein the seed comprises the modified cry3A gene.

52. Transgenic seed from the maize plant of claim 50, wherein the seed comprises the modified cry3A gene.

53. A transgenic maize plant comprising a modified cry3A gene comprising a nucleotide sequence that encodes a modified Cry3A toxin comprising a cathepsin G recognition site, wherein said modified cry3A gene comprises a coding sequence encoding said cathepsin G recognition site, wherein said coding sequence modifies a cry3A gene and is inserted at a position between the codons that code for amino acids corresponding to amino acid numbers 107 and 115 of SEQ ID NO: 4, wherein said cathepsin G recognition site is recognizable by a gut protease of western corn rootworm, and wherein said transgenic plant expresses said modified Cry3A toxin in root tissue at a level that causes mortality to western corn rootworm.

54. The transgenic maize plant according to claim 53, wherein said nucleotide sequence comprises nucleotides 1–1806 of SEQ ID NO: 8.

55. The transgenic maize plant according to claim 53, wherein said modified Cry3A toxin comprises the amino acid sequence set forth in SEQ ID NO: 9.

56. The transgenic maize plant according to claim 53, which is an inbred plant.

57. The transgenic maize plant according to claim 53, which is a hybrid plant.

58. Transgenic seed from the plant of claim 53, wherein the seed comprises the modified cry3A gene.

59. Transgenic seed from the plant of claim 56, wherein the seed comprises the modified cry3A gene.

60. Transgenic seed from the plant of claim 57, wherein the seed comprises the modified cry3A gene.

* * * * *

SEQUENCE LISTING

<160> NUMBER OF SEQ ID NOS: 38

<210> SEQ ID NO 1
<211> LENGTH: 1932
<212> TYPE: DNA
<213> ORGANISM: Bacillus thuringiensis
<220> FEATURE:
<221> NAME/KEY: CDS
<222> LOCATION: (1)..(1932)
<223> OTHER INFORMATION: Native cry3A coding sequence according to Sekar
      et al. 1987,Proc.Natl. Aca. Sci. 84:7036-7040

<400> SEQUENCE: 1

```
atg aat ccg aac aat cga agt gaa cat gat aca ata aaa act act gaa      48
Met Asn Pro Asn Asn Arg Ser Glu His Asp Thr Ile Lys Thr Thr Glu
1               5                  10                  15 aat aat gag gtg cca act aac cat gtt caa tat cct tta gcg gaa act      96
Asn Asn Glu Val Pro Thr Asn His Val Gln Tyr Pro Leu Ala Glu Thr
            20                  25                  30 cca aat cca aca cta gaa gat tta aat tat aaa gag ttt tta aga atg     144
Pro Asn Pro Thr Leu Glu Asp Leu Asn Tyr Lys Glu Phe Leu Arg Met
        35                  40                  45 act gca gat aat aat acg gaa gca cta gat agc tct aca aca aaa gat     192
Thr Ala Asp Asn Asn Thr Glu Ala Leu Asp Ser Ser Thr Thr Lys Asp
    50                  55                  60 gtc att caa aaa ggc att tcc gta gta ggt gat ctc cta ggc gta gta     240
Val Ile Gln Lys Gly Ile Ser Val Val Gly Asp Leu Leu Gly Val Val
65                  70                  75                  80 ggt ttc ccg ttt ggt gga gcg ctt gtt tcg ttt tat aca aac ttt tta     288
Gly Phe Pro Phe Gly Gly Ala Leu Val Ser Phe Tyr Thr Asn Phe Leu
                85                  90                  95 aat act att tgg cca agt gaa gac ccg tgg aag gct ttt atg gaa caa     336
Asn Thr Ile Trp Pro Ser Glu Asp Pro Trp Lys Ala Phe Met Glu Gln
            100                 105                 110 gta gaa gca ttg atg gat cag aaa ata gct gat tat gca aaa aat aaa     384
Val Glu Ala Leu Met Asp Gln Lys Ile Ala Asp Tyr Ala Lys Asn Lys
        115                 120                 125
```

```
gct ctt gca gag tta cag ggc ctt caa aat aat gtc gaa gat tat gtg      432
Ala Leu Ala Glu Leu Gln Gly Leu Gln Asn Asn Val Glu Asp Tyr Val
    130             135                 140 agt gca ttg agt tca tgg caa aaa aat cct gtg agt tca cga aat cca      480
Ser Ala Leu Ser Ser Trp Gln Lys Asn Pro Val Ser Ser Arg Asn Pro
145             150                 155                 160 cat agc cag ggg cgg ata aga gag ctg ttt tct caa gca gaa agt cat      528
His Ser Gln Gly Arg Ile Arg Glu Leu Phe Ser Gln Ala Glu Ser His
                165                 170                 175 ttt cgt aat tca atg cct tcg ttt gca att tct gga tac gag gtt cta      576
Phe Arg Asn Ser Met Pro Ser Phe Ala Ile Ser Gly Tyr Glu Val Leu
                180                 185                 190 ttt cta aca aca tat gca caa gct gcc aac aca cat tta ttt tta cta      624
Phe Leu Thr Thr Tyr Ala Gln Ala Ala Asn Thr His Leu Phe Leu Leu
            195                 200                 205 aaa gac gct caa att tat gga gaa gaa tgg gga tac gaa aaa gaa gat      672
Lys Asp Ala Gln Ile Tyr Gly Glu Glu Trp Gly Tyr Glu Lys Glu Asp
        210                 215                 220 att gct gaa ttt tat aaa aga caa cta aaa ctt acg caa gaa tat act      720
Ile Ala Glu Phe Tyr Lys Arg Gln Leu Lys Leu Thr Gln Glu Tyr Thr
225                 230                 235                 240 gac cat tgt gtc aaa tgg tat aat gtt gga tta gat aaa tta aga ggt      768
Asp His Cys Val Lys Trp Tyr Asn Val Gly Leu Asp Lys Leu Arg Gly
                245                 250                 255 tca tct tat gaa tct tgg gta aac ttt aac cgt tat cgc aga gag atg      816
Ser Ser Tyr Glu Ser Trp Val Asn Phe Asn Arg Tyr Arg Arg Glu Met
                260                 265                 270 aca tta aca gta tta gat tta att gca cta ttt cca ttg tat gat gtt      864
Thr Leu Thr Val Leu Asp Leu Ile Ala Leu Phe Pro Leu Tyr Asp Val
            275                 280                 285 cgg cta tac cca aaa gaa gtt aaa acc gaa tta aca aga gac gtt tta      912
Arg Leu Tyr Pro Lys Glu Val Lys Thr Glu Leu Thr Arg Asp Val Leu
        290                 295                 300 aca gat cca att gtc gga gtc aac aac ctt agg ggc tat gga aca acc      960
Thr Asp Pro Ile Val Gly Val Asn Asn Leu Arg Gly Tyr Gly Thr Thr
305                 310                 315                 320 ttc tct aat ata gaa aat tat att cga aaa cca cat cta ttt gac tat     1008
Phe Ser Asn Ile Glu Asn Tyr Ile Arg Lys Pro His Leu Phe Asp Tyr
                325                 330                 335 ctg cat aga att caa ttt cac acg cgg ttc caa cca gga tat tat gga     1056
Leu His Arg Ile Gln Phe His Thr Arg Phe Gln Pro Gly Tyr Tyr Gly
                340                 345                 350 aat gac tct ttc aat tat tgg tcc ggt aat tat gtt tca act aga cca     1104
Asn Asp Ser Phe Asn Tyr Trp Ser Gly Asn Tyr Val Ser Thr Arg Pro
            355                 360                 365 agc ata gga tca aat gat ata atc aca tct cca ttc tat gga aat aaa     1152
Ser Ile Gly Ser Asn Asp Ile Ile Thr Ser Pro Phe Tyr Gly Asn Lys
        370                 375                 380 tcc agt gaa cct gta caa aat tta gaa ttt aat gga gaa aaa gtc tat     1200
Ser Ser Glu Pro Val Gln Asn Leu Glu Phe Asn Gly Glu Lys Val Tyr
385                 390                 395                 400 aga gcc gta gca aat aca aat ctt gcg gtc tgg ccg tcc gct gta tat     1248
Arg Ala Val Ala Asn Thr Asn Leu Ala Val Trp Pro Ser Ala Val Tyr
                405                 410                 415 tca ggt gtt aca aaa gtg gaa ttt agc caa tat aat gat caa aca gat     1296
Ser Gly Val Thr Lys Val Glu Phe Ser Gln Tyr Asn Asp Gln Thr Asp
                420                 425                 430 gaa gca agt aca caa acg tac gac tca aaa aga aat gtt ggc gcg gtc     1344
Glu Ala Ser Thr Gln Thr Tyr Asp Ser Lys Arg Asn Val Gly Ala Val
            435                 440                 445
```

-continued

```
agc tgg gat tct atc gat caa ttg cct cca gaa aca aca gat gaa cct      1392
Ser Trp Asp Ser Ile Asp Gln Leu Pro Pro Glu Thr Thr Asp Glu Pro
    450                 455                 460 cta gaa aag gga tat agc cat caa ctc aat tat gta atg tgc ttt tta      1440
Leu Glu Lys Gly Tyr Ser His Gln Leu Asn Tyr Val Met Cys Phe Leu
465                 470                 475                 480 atg cag ggt agt aga gga aca atc cca gtg tta act tgg aca cat aaa      1488
Met Gln Gly Ser Arg Gly Thr Ile Pro Val Leu Thr Trp Thr His Lys
                485                 490                 495 agt gta gac ttt ttt aac atg att gat tcg aaa aaa att aca caa ctt      1536
Ser Val Asp Phe Phe Asn Met Ile Asp Ser Lys Lys Ile Thr Gln Leu
            500                 505                 510 ccg tta gta aag gca tat aag tta caa tct ggt gct tcc gtt gtc gca      1584
Pro Leu Val Lys Ala Tyr Lys Leu Gln Ser Gly Ala Ser Val Val Ala
        515                 520                 525 ggt cct agg ttt aca gga gga gat atc att caa tgc aca gaa aat gga      1632
Gly Pro Arg Phe Thr Gly Gly Asp Ile Ile Gln Cys Thr Glu Asn Gly
    530                 535                 540 agt gcg gca act att tac gtt aca ccg gat gtg tcg tac tct caa aaa      1680
Ser Ala Ala Thr Ile Tyr Val Thr Pro Asp Val Ser Tyr Ser Gln Lys
545                 550                 555                 560 tat cga gct aga att cat tat gct tct aca tct cag ata aca ttt aca      1728
Tyr Arg Ala Arg Ile His Tyr Ala Ser Thr Ser Gln Ile Thr Phe Thr
                565                 570                 575 ctc agt tta gac ggg gca cca ttt aat caa tac tat ttc gat aaa acg      1776
Leu Ser Leu Asp Gly Ala Pro Phe Asn Gln Tyr Tyr Phe Asp Lys Thr
            580                 585                 590 ata aat aaa gga gac aca tta acg tat aat tca ttt aat tta gca agt      1824
Ile Asn Lys Gly Asp Thr Leu Thr Tyr Asn Ser Phe Asn Leu Ala Ser
        595                 600                 605 ttc agc aca cca ttc gaa tta tca ggg aat aac tta caa ata ggc gtc      1872
Phe Ser Thr Pro Phe Glu Leu Ser Gly Asn Asn Leu Gln Ile Gly Val
    610                 615                 620 aca gga tta agt gct gga gat aaa gtt tat ata gac aaa att gaa ttt      1920
Thr Gly Leu Ser Ala Gly Asp Lys Val Tyr Ile Asp Lys Ile Glu Phe
625                 630                 635                 640 att cca gtg aat                                                      1932
Ile Pro Val Asn
```

<210> SEQ ID NO 2
<211> LENGTH: 644
<212> TYPE: PRT
<213> ORGANISM: Bacillus thuringiensis

<400> SEQUENCE: 2

```
Met Asn Pro Asn Asn Arg Ser Glu His Asp Thr Ile Lys Thr Thr Glu
1               5                   10                  15

Asn Asn Glu Val Pro Thr Asn His Val Gln Tyr Pro Leu Ala Glu Thr
            20                  25                  30

Pro Asn Pro Thr Leu Glu Asp Leu Asn Tyr Lys Glu Phe Leu Arg Met
        35                  40                  45

Thr Ala Asp Asn Asn Thr Glu Ala Leu Asp Ser Ser Thr Thr Lys Asp
    50                  55                  60

Val Ile Gln Lys Gly Ile Ser Val Val Gly Asp Leu Leu Gly Val Val
65                  70                  75                  80

Gly Phe Pro Phe Gly Gly Ala Leu Val Ser Phe Tyr Thr Asn Phe Leu
                85                  90                  95

Asn Thr Ile Trp Pro Ser Glu Asp Pro Trp Lys Ala Phe Met Glu Gln
```

-continued

```
                100                 105                 110
Val Glu Ala Leu Met Asp Gln Lys Ile Ala Asp Tyr Ala Lys Asn Lys
            115                 120                 125
Ala Leu Ala Glu Leu Gln Gly Leu Gln Asn Asn Val Glu Asp Tyr Val
        130                 135                 140
Ser Ala Leu Ser Ser Trp Gln Lys Asn Pro Val Ser Ser Arg Asn Pro
145                 150                 155                 160
His Ser Gln Gly Arg Ile Arg Glu Leu Phe Ser Gln Ala Glu Ser His
                165                 170                 175
Phe Arg Asn Ser Met Pro Ser Phe Ala Ile Ser Gly Tyr Glu Val Leu
            180                 185                 190
Phe Leu Thr Thr Tyr Ala Gln Ala Ala Asn Thr His Leu Phe Leu Leu
        195                 200                 205
Lys Asp Ala Gln Ile Tyr Gly Glu Glu Trp Gly Tyr Glu Lys Glu Asp
210                 215                 220
Ile Ala Glu Phe Tyr Lys Arg Gln Leu Lys Leu Thr Gln Glu Tyr Thr
225                 230                 235                 240
Asp His Cys Val Lys Trp Tyr Asn Val Gly Leu Asp Lys Leu Arg Gly
                245                 250                 255
Ser Ser Tyr Glu Ser Trp Val Asn Phe Asn Arg Tyr Arg Arg Glu Met
            260                 265                 270
Thr Leu Thr Val Leu Asp Leu Ile Ala Leu Phe Pro Leu Tyr Asp Val
        275                 280                 285
Arg Leu Tyr Pro Lys Glu Val Lys Thr Glu Leu Thr Arg Asp Val Leu
        290                 295                 300
Thr Asp Pro Ile Val Gly Val Asn Asn Leu Arg Gly Tyr Gly Thr Thr
305                 310                 315                 320
Phe Ser Asn Ile Glu Asn Tyr Ile Arg Lys Pro His Leu Phe Asp Tyr
                325                 330                 335
Leu His Arg Ile Gln Phe His Thr Arg Phe Gln Pro Gly Tyr Tyr Gly
            340                 345                 350
Asn Asp Ser Phe Asn Tyr Trp Ser Gly Asn Tyr Val Ser Thr Arg Pro
        355                 360                 365
Ser Ile Gly Ser Asn Asp Ile Ile Thr Ser Pro Phe Tyr Gly Asn Lys
370                 375                 380
Ser Ser Glu Pro Val Gln Asn Leu Glu Phe Asn Gly Glu Lys Val Tyr
385                 390                 395                 400
Arg Ala Val Ala Asn Thr Asn Leu Ala Val Trp Pro Ser Ala Val Tyr
                405                 410                 415
Ser Gly Val Thr Lys Val Glu Phe Ser Gln Tyr Asn Asp Gln Thr Asp
            420                 425                 430
Glu Ala Ser Thr Gln Thr Tyr Asp Ser Lys Arg Asn Val Gly Ala Val
        435                 440                 445
Ser Trp Asp Ser Ile Asp Gln Leu Pro Pro Glu Thr Thr Asp Glu Pro
        450                 455                 460
Leu Glu Lys Gly Tyr Ser His Gln Leu Asn Tyr Val Met Cys Phe Leu
465                 470                 475                 480
Met Gln Gly Ser Arg Gly Thr Ile Pro Val Leu Thr Trp Thr His Lys
                485                 490                 495
Ser Val Asp Phe Phe Asn Met Ile Asp Ser Lys Lys Ile Thr Gln Leu
            500                 505                 510
Pro Leu Val Lys Ala Tyr Lys Leu Gln Ser Gly Ala Ser Val Val Ala
        515                 520                 525
```

-continued

```
Gly Pro Arg Phe Thr Gly Gly Asp Ile Ile Gln Cys Thr Glu Asn Gly
        530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
        595                 600                 605

Phe Ser Thr Pro Phe Glu Leu Ser Gly Asn Asn Leu Gln Ile Gly Val
    610                 615                 620

Thr Gly Leu Ser Ala Gly Asp Lys Val Tyr Ile Asp Lys Ile Glu Phe
625                 630                 635                 640

Ile Pro Val Asn
```

<210> SEQ ID NO 3
<211> LENGTH: 1803
<212> TYPE: DNA
<213> ORGANISM: Artificial Sequence
<220> FEATURE:
<221> NAME/KEY: CDS
<222> LOCATION: (1)..(1794)
<223> OTHER INFORMATION: Maize optimized cry3A coding sequence

<400> SEQUENCE: 3

```
atg acg gcc gac aac aac acc gag gcc ctg gac agc agc acc acc aag       48
Met Thr Ala Asp Asn Asn Thr Glu Ala Leu Asp Ser Ser Thr Thr Lys
1               5                   10                  15 gac gtg atc cag aag ggc atc agc gtg gtg ggc gac ctg ctg ggc gtg       96
Asp Val Ile Gln Lys Gly Ile Ser Val Val Gly Asp Leu Leu Gly Val
                20                  25                  30 gtg ggc ttc ccc ttc ggc ggc gcc ctg gtg agc ttc tac acc aac ttc      144
Val Gly Phe Pro Phe Gly Gly Ala Leu Val Ser Phe Tyr Thr Asn Phe
            35                  40                  45 ctg aac acc atc tgg ccc agc gag gac ccc tgg aag gcc ttc atg gag      192
Leu Asn Thr Ile Trp Pro Ser Glu Asp Pro Trp Lys Ala Phe Met Glu
        50                  55                  60 cag gtg gag gcc ctg atg gac cag aag atc gcc gac tac gcc aag aac      240
Gln Val Glu Ala Leu Met Asp Gln Lys Ile Ala Asp Tyr Ala Lys Asn
65                  70                  75                  80 aag gca ctg gcc gag cta cag ggc ctc cag aac aac gtg gag gac tat      288
Lys Ala Leu Ala Glu Leu Gln Gly Leu Gln Asn Asn Val Glu Asp Tyr
                85                  90                  95 gtg agc gcc ctg agc agc tgg cag aag aac ccc gtc tcg agc cgc aac      336
Val Ser Ala Leu Ser Ser Trp Gln Lys Asn Pro Val Ser Ser Arg Asn
            100                 105                 110 ccc cac agc cag ggc cgc atc cgc gag ctg ttc agc cag gcc gag agc      384
Pro His Ser Gln Gly Arg Ile Arg Glu Leu Phe Ser Gln Ala Glu Ser
        115                 120                 125 cac ttc cgc aac agc atg ccc agc ttc gcc atc agc ggc tac gag gtg      432
His Phe Arg Asn Ser Met Pro Ser Phe Ala Ile Ser Gly Tyr Glu Val
    130                 135                 140 ctg ttc ctg acc acc tac gcc cag gcc gcc aac acc cac ctg ttc ctg      480
Leu Phe Leu Thr Thr Tyr Ala Gln Ala Ala Asn Thr His Leu Phe Leu
145                 150                 155                 160 ctg aag gac gcc caa atc tac gga gag gag tgg ggc tac gag aag gag      528
Leu Lys Asp Ala Gln Ile Tyr Gly Glu Glu Trp Gly Tyr Glu Lys Glu
                165                 170                 175
```

```
gac atc gcc gag ttc tac aag cgc cag ctg aag ctg acc cag gag tac        576
Asp Ile Ala Glu Phe Tyr Lys Arg Gln Leu Lys Leu Thr Gln Glu Tyr
        180                 185                 190 acc gac cac tgc gtg aag tgg tac aac gtg ggt cta gac aag ctc cgc        624
Thr Asp His Cys Val Lys Trp Tyr Asn Val Gly Leu Asp Lys Leu Arg
    195                 200                 205 ggc agc agc tac gag agc tgg gtg aac ttc aac cgc tac cgc cgc gag        672
Gly Ser Ser Tyr Glu Ser Trp Val Asn Phe Asn Arg Tyr Arg Arg Glu
210                 215                 220 atg acc ctg acc gtg ctg gac ctg atc gcc ctg ttc ccc ctg tac gac        720
Met Thr Leu Thr Val Leu Asp Leu Ile Ala Leu Phe Pro Leu Tyr Asp
225                 230                 235                 240 gtg cgc ctg tac ccc aag gag gtg aag acc gag ctg acc cgc gac gtg        768
Val Arg Leu Tyr Pro Lys Glu Val Lys Thr Glu Leu Thr Arg Asp Val
            245                 250                 255 ctg acc gac ccc atc gtg ggc gtg aac aac ctg cgc ggc tac ggc acc        816
Leu Thr Asp Pro Ile Val Gly Val Asn Asn Leu Arg Gly Tyr Gly Thr
        260                 265                 270 acc ttc agc aac atc gag aac tac atc cgc aag ccc cac ctg ttc gac        864
Thr Phe Ser Asn Ile Glu Asn Tyr Ile Arg Lys Pro His Leu Phe Asp
    275                 280                 285 tac ctg cac cgc atc cag ttc cac acg cgt ttc cag ccc ggc tac tac        912
Tyr Leu His Arg Ile Gln Phe His Thr Arg Phe Gln Pro Gly Tyr Tyr
290                 295                 300 ggc aac gac agc ttc aac tac tgg agc ggc aac tac gtg agc acc cgc        960
Gly Asn Asp Ser Phe Asn Tyr Trp Ser Gly Asn Tyr Val Ser Thr Arg
305                 310                 315                 320 ccc agc atc ggc agc aac gac atc atc acc agc ccc ttc tac ggc aac       1008
Pro Ser Ile Gly Ser Asn Asp Ile Ile Thr Ser Pro Phe Tyr Gly Asn
            325                 330                 335 aag agc agc gag ccc gtg cag aac ctt gag ttc aac ggc gag aag gtg       1056
Lys Ser Ser Glu Pro Val Gln Asn Leu Glu Phe Asn Gly Glu Lys Val
        340                 345                 350 tac cgc gcc gtg gct aac acc aac ctg gcc gtg tgg ccc tct gca gtg       1104
Tyr Arg Ala Val Ala Asn Thr Asn Leu Ala Val Trp Pro Ser Ala Val
    355                 360                 365 tac agc ggc gtg acc aag gtg gag ttc agc cag tac aac gac cag acc       1152
Tyr Ser Gly Val Thr Lys Val Glu Phe Ser Gln Tyr Asn Asp Gln Thr
370                 375                 380 gac gag gcc agc acc cag acc tac gac agc aag cgc aac gtg ggc gcc       1200
Asp Glu Ala Ser Thr Gln Thr Tyr Asp Ser Lys Arg Asn Val Gly Ala
385                 390                 395                 400 gtg agc tgg gac agc atc gac cag ctg ccc ccc gag acc acc gac gag       1248
Val Ser Trp Asp Ser Ile Asp Gln Leu Pro Pro Glu Thr Thr Asp Glu
            405                 410                 415 ccc ctg gag aag ggc tac agc cac cag ctg aac tac gtg atg tgc ttc       1296
Pro Leu Glu Lys Gly Tyr Ser His Gln Leu Asn Tyr Val Met Cys Phe
        420                 425                 430 ctg atg cag ggc agc cgc ggc acc atc ccc gtg ctg acc tgg acc cac       1344
Leu Met Gln Gly Ser Arg Gly Thr Ile Pro Val Leu Thr Trp Thr His
    435                 440                 445 aag agc gtc gac ttc ttc aac atg atc gac agc aag aag atc acc cag       1392
Lys Ser Val Asp Phe Phe Asn Met Ile Asp Ser Lys Lys Ile Thr Gln
450                 455                 460 ctg ccc ctg gtg aag gcc tac aag ctc cag agc ggc gcc agc gtg gtg       1440
Leu Pro Leu Val Lys Ala Tyr Lys Leu Gln Ser Gly Ala Ser Val Val
465                 470                 475                 480 gca ggc ccc cgc ttc acc ggc ggc gac atc atc cag tgc acc gag aac       1488
Ala Gly Pro Arg Phe Thr Gly Gly Asp Ile Ile Gln Cys Thr Glu Asn
```

-continued

```
                          485                 490                 495
ggc agc gcc gcc acc atc tac gtg acc ccc gac gtg agc tac agc cag         1536
Gly Ser Ala Ala Thr Ile Tyr Val Thr Pro Asp Val Ser Tyr Ser Gln
            500                 505                 510 aag tac cgc gcc cgc atc cac tac gcc agc acc agc cag atc acc ttc         1584
Lys Tyr Arg Ala Arg Ile His Tyr Ala Ser Thr Ser Gln Ile Thr Phe
        515                 520                 525 acc ctg agc ctg gac ggg gcc ccc ttc aac caa tac tac ttc gac aag         1632
Thr Leu Ser Leu Asp Gly Ala Pro Phe Asn Gln Tyr Tyr Phe Asp Lys
    530                 535                 540 acc atc aac aag ggc gac acc ctg acc tac aac agc ttc aac ctg gcc         1680
Thr Ile Asn Lys Gly Asp Thr Leu Thr Tyr Asn Ser Phe Asn Leu Ala
545                 550                 555                 560 agc ttc agc acc cct ttc gag ctg agc ggc aac aac ctc cag atc ggc         1728
Ser Phe Ser Thr Pro Phe Glu Leu Ser Gly Asn Asn Leu Gln Ile Gly
                565                 570                 575 gtg acc ggc ctg agc gcc ggc gac aag gtg tac atc gac aag atc gag         1776
Val Thr Gly Leu Ser Ala Gly Asp Lys Val Tyr Ile Asp Lys Ile Glu
            580                 585                 590 ttc atc ccc gtg aac tag atctgagct                                       1803
Phe Ile Pro Val Asn
        595

<210> SEQ ID NO 4
<211> LENGTH: 597
<212> TYPE: PRT
<213> ORGANISM: Bacillus thuringiensis

<400> SEQUENCE: 4

Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Val Ser Ser Arg Asn
            100                 105                 110

Pro His Ser Gln Gly Arg Ile Arg Glu Leu Phe Ser Gln Ala Glu Ser
        115                 120                 125

His Phe Arg Asn Ser Met Pro Ser Phe Ala Ile Ser Gly Tyr Glu Val
    130                 135                 140

Leu Phe Leu Thr Thr Tyr Ala Gln Ala Ala Asn Thr His Leu Phe Leu
145                 150                 155                 160

Leu Lys Asp Ala Gln Ile Tyr Gly Glu Glu Trp Gly Tyr Glu Lys Glu
                165                 170                 175

Asp Ile Ala Glu Phe Tyr Lys Arg Gln Leu Lys Leu Thr Gln Glu Tyr
            180                 185                 190

Thr Asp His Cys Val Lys Trp Tyr Asn Val Gly Leu Asp Lys Leu Arg
        195                 200                 205

Gly Ser Ser Tyr Glu Ser Trp Val Asn Phe Asn Arg Tyr Arg Arg Glu
    210                 215                 220
```

-continued

```
Met Thr Leu Thr Val Leu Asp Leu Ile Ala Leu Phe Pro Leu Tyr Asp
225                 230                 235                 240

Val Arg Leu Tyr Pro Lys Glu Val Lys Thr Glu Leu Thr Arg Asp Val
            245                 250                 255

Leu Thr Asp Pro Ile Val Gly Val Asn Asn Leu Arg Gly Tyr Gly Thr
        260                 265                 270

Thr Phe Ser Asn Ile Glu Asn Tyr Ile Arg Lys Pro His Leu Phe Asp
    275                 280                 285

Tyr Leu His Arg Ile Gln Phe His Thr Arg Phe Gln Pro Gly Tyr Tyr
290                 295                 300

Gly Asn Asp Ser Phe Asn Tyr Trp Ser Gly Asn Tyr Val Ser Thr Arg
305                 310                 315                 320

Pro Ser Ile Gly Ser Asn Asp Ile Ile Thr Ser Pro Phe Tyr Gly Asn
            325                 330                 335

Lys Ser Ser Glu Pro Val Gln Asn Leu Glu Phe Asn Gly Glu Lys Val
        340                 345                 350

Tyr Arg Ala Val Ala Asn Thr Asn Leu Ala Val Trp Pro Ser Ala Val
    355                 360                 365

Tyr Ser Gly Val Thr Lys Val Glu Phe Ser Gln Tyr Asn Asp Gln Thr
370                 375                 380

Asp Glu Ala Ser Thr Gln Thr Tyr Asp Ser Lys Arg Asn Val Gly Ala
385                 390                 395                 400

Val Ser Trp Asp Ser Ile Asp Gln Leu Pro Pro Glu Thr Thr Asp Glu
            405                 410                 415

Pro Leu Glu Lys Gly Tyr Ser His Gln Leu Asn Tyr Val Met Cys Phe
        420                 425                 430

Leu Met Gln Gly Ser Arg Gly Thr Ile Pro Val Leu Thr Trp Thr His
    435                 440                 445

Lys Ser Val Asp Phe Phe Asn Met Ile Asp Ser Lys Lys Ile Thr Gln
450                 455                 460

Leu Pro Leu Val Lys Ala Tyr Lys Leu Gln Ser Gly Ala Ser Val Val
465                 470                 475                 480

Ala Gly Pro Arg Phe Thr Gly Gly Asp Ile Ile Gln Cys Thr Glu Asn
            485                 490                 495

Gly Ser Ala Ala Thr Ile Tyr Val Thr Pro Asp Val Ser Tyr Ser Gln
        500                 505                 510

Lys Tyr Arg Ala Arg Ile His Tyr Ala Ser Thr Ser Gln Ile Thr Phe
    515                 520                 525

Thr Leu Ser Leu Asp Gly Ala Pro Phe Asn Gln Tyr Tyr Phe Asp Lys
530                 535                 540

Thr Ile Asn Lys Gly Asp Thr Leu Thr Tyr Asn Ser Phe Asn Leu Ala
545                 550                 555                 560

Ser Phe Ser Thr Pro Phe Glu Leu Ser Gly Asn Asn Leu Gln Ile Gly
            565                 570                 575

Val Thr Gly Leu Ser Ala Gly Asp Lys Val Tyr Ile Asp Lys Ile Glu
        580                 585                 590

Phe Ile Pro Val Asn
    595
```

<210> SEQ ID NO 5
<211> LENGTH: 7208
<212> TYPE: DNA
<213> ORGANISM: Artificial Sequence
<220> FEATURE:

<221> NAME/KEY: misc_feature
<223> OTHER INFORMATION: pCIB6850

<400> SEQUENCE: 5

```
gatccaccat gacggccgac aacaacaccg aggccctgga cagcagcacc accaaggacg      60
tgatccagaa gggcatcagc gtggtgggcg acctgctggg cgtggtgggc ttccccttcg     120
gcggcgccct ggtgagcttc tacaccaact tcctgaacac catctggccc agcgaggacc     180
cctggaaggc cttcatggag caggtggagg ccctgatgga ccagaagatc gccgactacg     240
ccaagaacaa ggcactggcc gagctacagg gcctccagaa caacgtggag gactatgtga     300
gcgccctgag cagctggcag aagaaccccg tctcgagccg caaccccac agccagggcc     360
gcatccgcga gctgttcagc caggccgaga gccacttccg caacagcatg cccagcttcg     420
ccatcagcgg ctacgaggtg ctgttcctga ccacctacgc ccaggccgcc aacacccacc     480
tgttcctgct gaaggacgcc caaatctacg gagaggagtg gggctacgag aaggaggaca     540
tcgccgagtt ctacaagcgc cagctgaagc tgacccagga gtacaccgac cactgcgtga     600
agtggtacaa cgtgggtcta gacaagctcc gcggcagcag ctacgagagc tgggtgaact     660
tcaaccgcta ccgccgcgag atgaccccga ccgtgctgga cctgatcgcc ctgttccccc     720
tgtacgacgt gcgcctgtac cccaaggagt gaagaccga gctgacccgc gacgtgctga     780
ccgaccccat cgtgggcgtg aacaacctgc gcggctacgg caccaccttc agcaacatcg     840
agaactacat ccgcaagccc cacctgttcg actacctgca ccgcatccag ttccacacgc     900
gtttccagcc cggctactac ggcaacgaca gcttcaacta ctggagcggc aactacgtga     960
gcacccgccc cagcatcggc agcaacgaca tcatcaccag ccccttctac ggcaacaaga    1020
gcagcgagcc cgtgcagaac cttgagttca cggcgagaa ggtgtaccgc gccgtggcta    1080
acaccaacct ggccgtgtgg ccctctgcag tgtacagcgg cgtgaccaag gtggagttca    1140
gccagtacaa cgaccagacc gacgaggcca gcacccagac ctacgacagc aagcgcaacg    1200
tgggcgccgt gagctgggac agcatcgacc agctgccccc cgagaccacc gacgagcccc    1260
tggagaaggg ctacagccac cagctgaact acgtgatgtg cttcctgatg cagggcagcc    1320
gcggcaccat ccccgtgctg acctggaccc acaagagcgt cgacttcttc aacatgatcg    1380
acagcaagaa gatcacccag ctgccccctgg tgaaggccta caagctccag agcggcgcca    1440
gcgtggtggc aggccccgc ttcaccggcg cgacatcat ccagtgcacc gagaacggca    1500
gcgccgccac catctacgtg accccgacg tgagctacag ccagaagtac cgcgcccgca    1560
tccactacgc cagcaccagc cagatcacct tcaccctgag cctggacggg ccccccttca    1620
accaatacta cttcgacaag accatcaaca agggcgacac cctgacctac aacagcttca    1680
acctggccag cttcagcacc cctttcgagc tgagcggcaa caacctccag atcggcgtga    1740
ccggcctgag cgcggcgac aagtgtaca tcgacaagat cgagttcatc cccgtgaact    1800
agatctgagc tcaagatctg ttgtacaaaa accagcaact cactgcactg cacttcactt    1860
cacttcactg tatgaataaa agtctggtgt ctggttcctg atcgatgact gactactcca    1920
cttttgtcag aacttagtat gtatttgtat ttgtaaaata cttctatcaa taaaatttct    1980
aattcctaaa accaaaatcc agtgggtacc gaattcactg gccgtcgttt tacaacgtcg    2040
tgactgggaa aaccctggcg ttacccaact taatcgcctt gcagcacatc cccctttcgc    2100
cagctggcgt aatagcgaag aggcccgcac cgatcgccct tcccaacagt tgcgcagcct    2160
gaatggcgaa tggcgcctga tgcggtattt tctccttacg catctgtgcg gtatttcaca    2220
```

```
ccgcatatgg tgcactctca gtacaatctg ctctgatgcc gcatagttaa gccagccccg    2280
acacccgcca acacccgctg acgcgccctg acgggcttgt ctgctcccgg catccgctta    2340
cagacaagct gtgaccgtct ccgggagctg catgtgtcag aggttttcac cgtcatcacc    2400
gaaacgcgcg agacgaaagg gcctcgtgat acgcctattt ttataggtta atgtcatgat    2460
aataatggtt tcttagacgt caggtggcac ttttcgggga atgtgcgcg gaacccctat    2520 ttgtttattt ttctaaatac attcaaatat gtatccgctc atgagacaat aaccctgata    2580
aatgcttcaa taatattgaa aaggaagag tatgagtatt caacatttcc gtgtcgccct    2640
tattcccttt tttgcggcat tttgccttcc tgttttgct cacccagaaa cgctggtgaa    2700
agtaaaagat gctgaagatc agttgggtgc acgagtgggt tacatcgaac tggatctcaa    2760
cagcggtaag atccttgaga gttttcgccc cgaagaacgt tttccaatga tgagcacttt    2820
taaagttctg ctatgtggcg cggtattatc ccgtattgac gccgggcaag agcaactcgg    2880
tcgccgcata cactattctc agaatgactt ggttgagtac tcaccagtca cagaaaagca    2940
tcttacggat ggcatgacag taagagaatt atgcagtgct gccataacca tgagtgataa    3000
cactgcggcc aacttacttc tgacaacgat cggaggaccg aaggagctaa ccgcttttt    3060 gcacaacatg ggggatcatg taactcgcct tgatcgttgg gaaccggagc tgaatgaagc    3120
cataccaaac gacgagcgtg acaccacgat gcctgtagca atggcaacaa cgttgcgcaa    3180
actattaact ggcgaactac ttactctagc ttcccggcaa caattaatag actggatgga    3240
ggcggataaa gttgcaggac cacttctgcg ctcggccctt ccggctggct ggtttattgc    3300
tgataaatct ggagccggtg agcgtgggtc tcgcggtatc attgcagcac tggggccaga    3360
tggtaagccc tcccgtatcg tagttatcta cacgacgggg agtcaggcaa ctatggatga    3420
acgaaataga cagatcgctg agataggtgc ctcactgatt aagcattggt aactgtcaga    3480
ccaagtttac tcatatatac tttagattga tttaaaactt cattttaat ttaaaaggat    3540 ctaggtgaag atcctttttg ataatctcat gaccaaaatc ccttaacgtg agttttcgtt    3600
ccactgagcg tcagaccccg tagaaaagat caaaggatct tcttgagatc ctttttttct    3660
gcgcgtaatc tgctgcttgc aaacaaaaaa accaccgcta ccagcggtgg tttgtttgcc    3720
ggatcaagag ctaccaactc tttttccgaa ggtaactggc ttcagcagag cgcagatacc    3780
aaatactgtc cttctagtgt agccgtagtt aggccaccac ttcaagaact ctgtagcacc    3840
gcctacatac ctcgctctgc taatcctgtt accagtggct gctgccagtg gcgataagtc    3900
gtgtcttacc gggttggact caagacgata gttaccggat aaggcgcagc ggtcgggctg    3960
aacggggggt tcgtgcacac agcccagctt ggagcgaacg acctacaccg aactgagata    4020
cctacagcgt gagctatgag aaagcgccac gcttcccgaa gggagaaagg cggacaggta    4080
tccggtaagc ggcagggtcg gaacaggaga gcgcacgagg gagcttccag ggggaaacgc    4140
ctggtatctt tatagtcctg tcgggtttcg ccacctctga cttgagcgtc gatttttgtg    4200
atgctcgtca gggggggcgga gcctatggaa aaacgccagc aacgcggcct ttttacggtt    4260
cctggccttt tgctggcctt ttgctcacat gttctttcct gcgttatccc ctgattctgt    4320
ggataaccgt attaccgcct ttgagtgagc tgataccgct cgccgcagcc gaacgaccga    4380
gcgcagcgag tcagtgagcg aggaagcgga agagcgccca atacgcaaac cgcctctccc    4440
cgcgcgttgg ccgattcatt aatgcagctg gcacgacagg tttcccgact ggaaagcggg    4500
cagtgagcgc aacgcaatta atgtgagtta gctcactcat taggcacccc aggctttaca    4560
ctttatgctt ccggctcgta tgttgtgtgg aattgtgagc ggataacaat ttcacacagg    4620
```

```
aaacagctat gaccatgatt acgccaagct tgcacatgac aacaattgta agaggatgga    4680
gaccacaacg atccaacaat acttctgcga cgggctgtga agtatagaga agttaaacgc    4740
ccaaaagcca ttgtgtttgg aattttagt tattctattt tcatgatgt atcttcctct    4800 aacatgcctt aatttgcaaa tttggtataa ctactgattg aaaatatatg tatgtaaaaa    4860
aatactaagc atatttgtga agctaaacat gatgttattt aagaaaatat gttgttaaca    4920
gaataagatt aatatcgaaa tggaaacatc tgtaaattag aatcatctta caagctaaga    4980
gatgttcacg ctttgagaaa cttcttcaga tcatgaccgt agaagtagct ctccaagact    5040
caacgaaggc tgctgcaatt ccacaaatgc atgacatgca tccttgtaac cgtcgtcgcc    5100
gctataaaca cggataactc aattccctgc tccatcaatt tagaaatgag caagcaagca    5160
cccgatcgct caccccatat gcaccaatct gactcccaag tctctgtttc gcattagtac    5220
cgccagcact ccacctatag ctaccaattg agacctttcc agcctaagca gatcgattga    5280
tcgttagagt caaagagttg gtggtacggg tactttaact accatggaat gatggggcgt    5340
gatgtagagc ggaaagcgcc tccctacgcg gaacaacacc ctcgccatgc cgctcgacta    5400
cagcctcctc ctcgtcggcc gcccacaacg agggagcccg tggtcgcagc caccgaccag    5460
catgtctctg tgtcctcgtc cgacctcgac atgtcatggc aaacagtcgg acgccagcac    5520
cagactgacg acatgagtct ctgaagagcc cgccacctag aaagatccga gccctgctgc    5580
tggtagtggt aaccattttc gtcgcgctga cgcggagagc gagaggccag aaatttatag    5640
cgactgacgc tgtggcaggc acgctatcgg aggttacgac gtggcgggtc actcgacgcg    5700
gagttcacag gtcctatcct tgcatcgctc gggccggagt ttacgggact tatccttacg    5760
acgtgctcta aggttgcgat aacgggcgga ggaaggcgtg tggcgtgcgg agacggttta    5820
tacacgtagt gtgcgggagt gtgtttcgta gacgcgggaa agcacgacga cttacgaagg    5880
ttagtggagg aggaggacac actaaaatca ggacgcaaga aactcttcta ttatagtagt    5940
agagaagaga ttataggagt gtgggttgat tctaaagaaa atcgacgcag acaaccgtc    6000 aaaacggggtg ctttaatata gtagatatat atatatagag agagagagaa agtacaaagg    6060
atgcatttgt gtctgcatat gatcggagta ttactaacgg ccgtcgtaag aaggtccatc    6120
atgcgtggag cgagcccatt tggttggttg tcaggccgca gttaaggcct ccatatatga    6180
ttgtcgtcgg gcccataaca gcatctcctc caccagttta ttgtaagaat aaattaagta    6240
gagatatttg tcgtcgggca gaagaaactt ggacaagaag aagaagcaag ctaggccaat    6300
ttcttgccgg caagaggaag atagtggcct ctagtttata tatcggcgtg atgatgatgc    6360
tcctagctag aaatgagaga agaaaaacgg acgcgtgttt ggtgtgtgtc aatggcgtcc    6420
atccttccat cagatcagaa cgatgaaaaa gtcaagcacg gcatgcatag tatatgtata    6480
gcttgtttta gtgtggcttt gctgagacga atgaaagcaa cggcgggcat attttttcagt    6540 ggctgtagct ttcaggctga agagacgtg gcatgcaata attcagggaa ttcgtcagcc    6600
aattgaggta gctagtcaac ttgtacattg gtgcgagcaa ttttccgcac tcaggagggc    6660
tagtttgaga gtccaaaaac tataggagat taaagaggct aaaatcctct ccttatttaa    6720
ttttaaataa gtagtgtatt tgtattttaa ctccctccaac ccttccgatt ttatggctct    6780
caaactagca ttcagtctaa tgcatgcatg cttggctaga ggtcgtatgg ggttgttaat    6840
agcatagcta gctacaagtt aaccgggtct tttatattta ataaggacag gcaaagtatt    6900
acttacaaat aaagaataaa gctaggacga actcgtggat tattactaaa tcgaaatgga    6960
```

-continued

```
cgtaatattc caggcaagaa taattgttcg atcaggagac aagtggggca ttggaccggt    7020
tcttgcaagc aagagcctat ggcgtggtga cacggcgcgt tgcccataca tcatgcctcc    7080
atcgatgatc catcctcact tgctataaaa agaggtgtcc atggtgctca agctcagcca    7140
agcaaataag acgacttgtt tcattgattc ttcaagagat cgagcttctt ttgcaccaca    7200
aggtcgag                                                             7208
```

<210> SEQ ID NO 6
<211> LENGTH: 1801
<212> TYPE: DNA
<213> ORGANISM: Artificial Sequence
<220> FEATURE:
<221> NAME/KEY: CDS
<222> LOCATION: (1)..(1791)
<223> OTHER INFORMATION: Maize optimized modified cry3A054 coding
      sequence.
<220> FEATURE:
<221> NAME/KEY: misc_feature
<222> LOCATION: (322)..(333)
<223> OTHER INFORMATION: cathepsin G recognition site coding sequence

<400> SEQUENCE: 6

```
atg acg gcc gac aac aac acc gag gcc ctg gac agc agc acc acc aag      48
Met Thr Ala Asp Asn Asn Thr Glu Ala Leu Asp Ser Ser Thr Thr Lys
 1               5                  10                  15 gac gtg atc cag aag ggc atc agc gtg gtg ggc gac ctg ctg ggc gtg      96
Asp Val Ile Gln Lys Gly Ile Ser Val Val Gly Asp Leu Leu Gly Val
             20                  25                  30 gtg ggc ttc ccc ttc ggc ggc gcc ctg gtg agc ttc tac acc aac ttc     144
Val Gly Phe Pro Phe Gly Gly Ala Leu Val Ser Phe Tyr Thr Asn Phe
         35                  40                  45 ctg aac acc atc tgg ccc agc gag gac ccc tgg aag gcc ttc atg gag     192
Leu Asn Thr Ile Trp Pro Ser Glu Asp Pro Trp Lys Ala Phe Met Glu
     50                  55                  60 cag gtg gag gcc ctg atg gac cag aag atc gcc gac tac gcc aag aac     240
Gln Val Glu Ala Leu Met Asp Gln Lys Ile Ala Asp Tyr Ala Lys Asn
 65                  70                  75                  80 aag gca ctg gcc gag cta cag ggc ctc cag aac aac gtg gag gac tat     288
Lys Ala Leu Ala Glu Leu Gln Gly Leu Gln Asn Asn Val Glu Asp Tyr
                 85                  90                  95 gtg agc gcc ctg agc agc tgg cag aag aac ccc gct gca ccg ttc ccc     336
Val Ser Ala Leu Ser Ser Trp Gln Lys Asn Pro Ala Ala Pro Phe Pro
            100                 105                 110 cac agc cag ggc cgc atc cgc gag ctg ttc agc cag gcc gag agc cac     384
His Ser Gln Gly Arg Ile Arg Glu Leu Phe Ser Gln Ala Glu Ser His
        115                 120                 125 ttc cgc aac agc atg ccc agc ttc gcc atc agc ggc tac gag gtg ctg     432
Phe Arg Asn Ser Met Pro Ser Phe Ala Ile Ser Gly Tyr Glu Val Leu
    130                 135                 140 ttc ctg acc acc tac gcc cag gcc gcc aac acc cac ctg ttc ctg ctg     480
Phe Leu Thr Thr Tyr Ala Gln Ala Ala Asn Thr His Leu Phe Leu Leu
145                 150                 155                 160 aag gac gcc caa atc tac gga gag gag tgg ggc tac gag aag gag gac     528
Lys Asp Ala Gln Ile Tyr Gly Glu Glu Trp Gly Tyr Glu Lys Glu Asp
                165                 170                 175 atc gcc gag ttc tac aag cgc cag ctg aag ctg acc cag gag tac acc     576
Ile Ala Glu Phe Tyr Lys Arg Gln Leu Lys Leu Thr Gln Glu Tyr Thr
            180                 185                 190 gac cac tgc gtg aag tgg tac aac gtg ggt cta gac aag ctc cgc ggc     624
Asp His Cys Val Lys Trp Tyr Asn Val Gly Leu Asp Lys Leu Arg Gly
        195                 200                 205
```

```
agc agc tac gag agc tgg gtg aac ttc aac cgc tac cgc cgc gag atg     672
Ser Ser Tyr Glu Ser Trp Val Asn Phe Asn Arg Tyr Arg Arg Glu Met
210             215                 220 acc ctg acc gtg ctg gac ctg atc gcc ctg ttc ccc ctg tac gac gtg     720
Thr Leu Thr Val Leu Asp Leu Ile Ala Leu Phe Pro Leu Tyr Asp Val
225             230                 235                 240 cgc ctg tac ccc aag gag gtg aag acc gag ctg acc cgc gac gtg ctg     768
Arg Leu Tyr Pro Lys Glu Val Lys Thr Glu Leu Thr Arg Asp Val Leu
                245                 250                 255 acc gac ccc atc gtg ggc gtg aac aac ctg cgc ggc tac ggc acc acc     816
Thr Asp Pro Ile Val Gly Val Asn Asn Leu Arg Gly Tyr Gly Thr Thr
            260                 265                 270 ttc agc aac atc gag aac tac atc cgc aag ccc cac ctg ttc gac tac     864
Phe Ser Asn Ile Glu Asn Tyr Ile Arg Lys Pro His Leu Phe Asp Tyr
        275                 280                 285 ctg cac cgc atc cag ttc cac acg cgt ttc cag ccc ggc tac tac ggc     912
Leu His Arg Ile Gln Phe His Thr Arg Phe Gln Pro Gly Tyr Tyr Gly
    290                 295                 300 aac gac agc ttc aac tac tgg agc ggc aac tac gtg agc acc cgc ccc     960
Asn Asp Ser Phe Asn Tyr Trp Ser Gly Asn Tyr Val Ser Thr Arg Pro
305             310                 315                 320 agc atc ggc agc aac gac atc atc acc agc ccc ttc tac ggc aac aag    1008
Ser Ile Gly Ser Asn Asp Ile Ile Thr Ser Pro Phe Tyr Gly Asn Lys
                325                 330                 335 agc agc gag ccc gtg cag aac ctt gag ttc aac ggc gag aag gtg tac    1056
Ser Ser Glu Pro Val Gln Asn Leu Glu Phe Asn Gly Glu Lys Val Tyr
            340                 345                 350 cgc gcc gtg gct aac acc aac ctg gcc gtg tgg ccc tct gca gtg tac    1104
Arg Ala Val Ala Asn Thr Asn Leu Ala Val Trp Pro Ser Ala Val Tyr
        355                 360                 365 agc ggc gtg acc aag gtg gag ttc agc cag tac aac gac cag acc gac    1152
Ser Gly Val Thr Lys Val Glu Phe Ser Gln Tyr Asn Asp Gln Thr Asp
    370                 375                 380 gag gcc agc acc cag acc tac gac agc aag cgc aac gtg ggc gcc gtg    1200
Glu Ala Ser Thr Gln Thr Tyr Asp Ser Lys Arg Asn Val Gly Ala Val
385             390                 395                 400 agc tgg gac agc atc gac cag ctg ccc ccc gag acc acc gac gag ccc    1248
Ser Trp Asp Ser Ile Asp Gln Leu Pro Pro Glu Thr Thr Asp Glu Pro
                405                 410                 415 ctg gag aag ggc tac agc cac cag ctg aac tac gtg atg tgc ttc ctg    1296
Leu Glu Lys Gly Tyr Ser His Gln Leu Asn Tyr Val Met Cys Phe Leu
            420                 425                 430 atg cag ggc agc cgc ggc acc atc ccc gtg ctg acc tgg acc cac aag    1344
Met Gln Gly Ser Arg Gly Thr Ile Pro Val Leu Thr Trp Thr His Lys
        435                 440                 445 agc gtc gac ttc ttc aac atg atc gac agc aag aag atc acc cag ctg    1392
Ser Val Asp Phe Phe Asn Met Ile Asp Ser Lys Lys Ile Thr Gln Leu
    450                 455                 460 ccc ctg gtg aag gcc tac aag ctc cag agc ggc gcc agc gtg gtg gca    1440
Pro Leu Val Lys Ala Tyr Lys Leu Gln Ser Gly Ala Ser Val Val Ala
465             470                 475                 480 ggc ccc cgc ttc acc ggc ggc gac atc atc cag tgc acc gag aac ggc    1488
Gly Pro Arg Phe Thr Gly Gly Asp Ile Ile Gln Cys Thr Glu Asn Gly
                485                 490                 495 agc gcc gcc acc atc tac gtg acc ccc gac gtg agc tac agc cag aag    1536
Ser Ala Ala Thr Ile Tyr Val Thr Pro Asp Val Ser Tyr Ser Gln Lys
            500                 505                 510 tac cgc gcc cgc atc cac tac gcc agc acc agc cag atc acc ttc acc    1584
Tyr Arg Ala Arg Ile His Tyr Ala Ser Thr Ser Gln Ile Thr Phe Thr
        515                 520                 525
```

```
ctg agc ctg gac ggg gcc ccc ttc aac caa tac tac ttc gac aag acc      1632
Leu Ser Leu Asp Gly Ala Pro Phe Asn Gln Tyr Tyr Phe Asp Lys Thr
        530                 535                 540 atc aac aag ggc gac acc ctg acc tac aac agc ttc aac ctg gcc agc      1680
Ile Asn Lys Gly Asp Thr Leu Thr Tyr Asn Ser Phe Asn Leu Ala Ser
545                 550                 555                 560 ttc agc acc cct ttc gag ctg agc ggc aac aac ctc cag atc ggc gtg      1728
Phe Ser Thr Pro Phe Glu Leu Ser Gly Asn Asn Leu Gln Ile Gly Val
                565                 570                 575 acc ggc ctg agc gcc ggc gac aag gtg tac atc gac aag atc gag ttc      1776
Thr Gly Leu Ser Ala Gly Asp Lys Val Tyr Ile Asp Lys Ile Glu Phe
            580                 585                 590 atc ccc gtg aac tag atctgagctc                                       1801
Ile Pro Val Asn
        595
```

<210> SEQ ID NO 7
<211> LENGTH: 596
<212> TYPE: PRT
<213> ORGANISM: Artificial Sequence
<220> FEATURE:
<221> NAME/KEY: misc_feature
<222> LOCATION: (108)..(111)
<223> OTHER INFORMATION: cathepsin G recognition sequence

<400> SEQUENCE: 7

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65              70                  75                  80

Lys Ala Leu Ala Glu Leu Gln Gly Leu Gln Asn Asn Val Glu Asp Tyr
            85                  90                  95

Val Ser Ala Leu Ser Ser Trp Gln Lys Asn Pro Ala Ala Pro Phe Pro
        100                 105                 110

His Ser Gln Gly Arg Ile Arg Glu Leu Phe Ser Gln Ala Glu Ser His
    115                 120                 125

Phe Arg Asn Ser Met Pro Ser Phe Ala Ile Ser Gly Tyr Glu Val Leu
130                 135                 140

Phe Leu Thr Thr Tyr Ala Gln Ala Ala Asn Thr His Leu Phe Leu Leu
145                 150                 155                 160

Lys Asp Ala Gln Ile Tyr Gly Glu Glu Trp Gly Tyr Glu Lys Glu Asp
            165                 170                 175

Ile Ala Glu Phe Tyr Lys Arg Gln Leu Lys Leu Thr Gln Glu Tyr Thr
        180                 185                 190

Asp His Cys Val Lys Trp Tyr Asn Val Gly Leu Asp Lys Leu Arg Gly
    195                 200                 205

Ser Ser Tyr Glu Ser Trp Val Asn Phe Asn Arg Tyr Arg Arg Glu Met
210                 215                 220

Thr Leu Thr Val Leu Asp Leu Ile Ala Leu Phe Pro Leu Tyr Asp Val
225                 230                 235                 240

Arg Leu Tyr Pro Lys Glu Val Lys Thr Glu Leu Thr Arg Asp Val Leu
```

```
                    245                 250                 255
Thr Asp Pro Ile Val Gly Val Asn Asn Leu Arg Gly Tyr Gly Thr Thr
            260                 265                 270

Phe Ser Asn Ile Glu Asn Tyr Ile Arg Lys Pro His Leu Phe Asp Tyr
        275                 280                 285

Leu His Arg Ile Gln Phe His Thr Arg Phe Gln Pro Gly Tyr Tyr Gly
    290                 295                 300

Asn Asp Ser Phe Asn Tyr Trp Ser Gly Asn Tyr Val Ser Thr Arg Pro
305                 310                 315                 320

Ser Ile Gly Ser Asn Asp Ile Ile Thr Ser Pro Phe Tyr Gly Asn Lys
                325                 330                 335

Ser Ser Glu Pro Val Gln Asn Leu Glu Phe Asn Gly Glu Lys Val Tyr
            340                 345                 350

Arg Ala Val Ala Asn Thr Asn Leu Ala Val Trp Pro Ser Ala Val Tyr
        355                 360                 365

Ser Gly Val Thr Lys Val Glu Phe Ser Gln Tyr Asn Asp Gln Thr Asp
    370                 375                 380

Glu Ala Ser Thr Gln Thr Tyr Asp Ser Lys Arg Asn Val Gly Ala Val
385                 390                 395                 400

Ser Trp Asp Ser Ile Asp Gln Leu Pro Pro Glu Thr Thr Asp Glu Pro
                405                 410                 415

Leu Glu Lys Gly Tyr Ser His Gln Leu Asn Tyr Val Met Cys Phe Leu
            420                 425                 430

Met Gln Gly Ser Arg Gly Thr Ile Pro Val Leu Thr Trp Thr His Lys
        435                 440                 445

Ser Val Asp Phe Phe Asn Met Ile Asp Ser Lys Lys Ile Thr Gln Leu
    450                 455                 460

Pro Leu Val Lys Ala Tyr Lys Leu Gln Ser Gly Ala Ser Val Val Ala
465                 470                 475                 480

Gly Pro Arg Phe Thr Gly Gly Asp Ile Ile Gln Cys Thr Glu Asn Gly
                485                 490                 495

Ser Ala Ala Thr Ile Tyr Val Thr Pro Asp Val Ser Tyr Ser Gln Lys
            500                 505                 510

Tyr Arg Ala Arg Ile His Tyr Ala Ser Thr Ser Gln Ile Thr Phe Thr
        515                 520                 525

Leu Ser Leu Asp Gly Ala Pro Phe Asn Gln Tyr Tyr Phe Asp Lys Thr
    530                 535                 540

Ile Asn Lys Gly Asp Thr Leu Thr Tyr Asn Ser Phe Asn Leu Ala Ser
545                 550                 555                 560

Phe Ser Thr Pro Phe Glu Leu Ser Gly Asn Asn Leu Gln Ile Gly Val
                565                 570                 575

Thr Gly Leu Ser Ala Gly Asp Lys Val Tyr Ile Asp Lys Ile Glu Phe
            580                 585                 590

Ile Pro Val Asn
        595

<210> SEQ ID NO 8
<211> LENGTH: 1807
<212> TYPE: DNA
<213> ORGANISM: Artificial Sequence
<220> FEATURE:
<221> NAME/KEY: CDS
<222> LOCATION: (1)..(1806)
<223> OTHER INFORMATION: Maize optimized modified cry3A055 coding
      sequence.

<210> NAME/KEY: misc_feature
<222> LOCATION: (322)..(333)
<223> OTHER INFORMATION: Cathepsin G recognition site coding sequence.

<400> SEQUENCE: 8

```
atg acg gcc gac aac aac acc gag gcc ctg gac agc agc acc acc aag      48
Met Thr Ala Asp Asn Asn Thr Glu Ala Leu Asp Ser Ser Thr Thr Lys
1               5                  10                  15 gac gtg atc cag aag ggc atc agc gtg gtg ggc gac ctg ctg ggc gtg      96
Asp Val Ile Gln Lys Gly Ile Ser Val Val Gly Asp Leu Leu Gly Val
            20                  25                  30 gtg ggc ttc ccc ttc ggc ggc gcc ctg gtg agc ttc tac acc aac ttc     144
Val Gly Phe Pro Phe Gly Gly Ala Leu Val Ser Phe Tyr Thr Asn Phe
        35                  40                  45 ctg aac acc atc tgg ccc agc gag gac ccc tgg aag gcc ttc atg gag     192
Leu Asn Thr Ile Trp Pro Ser Glu Asp Pro Trp Lys Ala Phe Met Glu
    50                  55                  60 cag gtg gag gcc ctg atg gac cag aag atc gcc gac tac gcc aag aac     240
Gln Val Glu Ala Leu Met Asp Gln Lys Ile Ala Asp Tyr Ala Lys Asn
65                  70                  75                  80 aag gca ctg gcc gag cta cag ggc ctc cag aac aac gtg gag gac tat     288
Lys Ala Leu Ala Glu Leu Gln Gly Leu Gln Asn Asn Val Glu Asp Tyr
                85                  90                  95 gtg agc gcc ctg agc agc tgg cag aag aac ccc gct gca ccg ttc cgc     336
Val Ser Ala Leu Ser Ser Trp Gln Lys Asn Pro Ala Ala Pro Phe Arg
            100                 105                 110 aac ccc cac agc cag ggc cgc atc cgc gag ctg ttc agc cag gcc gag     384
Asn Pro His Ser Gln Gly Arg Ile Arg Glu Leu Phe Ser Gln Ala Glu
        115                 120                 125 agc cac ttc cgc aac agc atg ccc agc ttc gcc atc agc ggc tac gag     432
Ser His Phe Arg Asn Ser Met Pro Ser Phe Ala Ile Ser Gly Tyr Glu
    130                 135                 140 gtg ctg ttc ctg acc acc tac gcc cag gcc gcc aac acc cac ctg ttc     480
Val Leu Phe Leu Thr Thr Tyr Ala Gln Ala Ala Asn Thr His Leu Phe
145                 150                 155                 160 ctg ctg aag gac gcc caa atc tac gga gag gag tgg ggc tac gag aag     528
Leu Leu Lys Asp Ala Gln Ile Tyr Gly Glu Glu Trp Gly Tyr Glu Lys
                165                 170                 175 gag gac atc gcc gag ttc tac aag cgc cag ctg aag ctg acc cag gag     576
Glu Asp Ile Ala Glu Phe Tyr Lys Arg Gln Leu Lys Leu Thr Gln Glu
            180                 185                 190 tac acc gac cac tgc gtg aag tgg tac aac gtg ggt cta gac aag ctc     624
Tyr Thr Asp His Cys Val Lys Trp Tyr Asn Val Gly Leu Asp Lys Leu
        195                 200                 205 cgc ggc agc agc tac gag agc tgg gtg aac ttc aac cgc tac cgc cgc     672
Arg Gly Ser Ser Tyr Glu Ser Trp Val Asn Phe Asn Arg Tyr Arg Arg
    210                 215                 220 gag atg acc ctg acc gtg ctg gac ctg atc gcc ctg ttc ccc ctg tac     720
Glu Met Thr Leu Thr Val Leu Asp Leu Ile Ala Leu Phe Pro Leu Tyr
225                 230                 235                 240 gac gtg cgc ctg tac ccc aag gag gtg aag acc gag ctg acc cgc gac     768
Asp Val Arg Leu Tyr Pro Lys Glu Val Lys Thr Glu Leu Thr Arg Asp
                245                 250                 255 gtg ctg acc gac ccc atc gtg ggc gtg aac aac ctg cgc ggc tac ggc     816
Val Leu Thr Asp Pro Ile Val Gly Val Asn Asn Leu Arg Gly Tyr Gly
            260                 265                 270 acc acc ttc agc aac atc gag aac tac atc cgc aag ccc cac ctg ttc     864
Thr Thr Phe Ser Asn Ile Glu Asn Tyr Ile Arg Lys Pro His Leu Phe
        275                 280                 285 gac tac ctg cac cgc atc cag ttc cac acg cgt ttc cag ccc ggc tac     912
Asp Tyr Leu His Arg Ile Gln Phe His Thr Arg Phe Gln Pro Gly Tyr
```

```
Asp Tyr Leu His Arg Ile Gln Phe His Thr Arg Phe Gln Pro Gly Tyr
    290                 295                 300 tac ggc aac gac agc ttc aac tac tgg agc ggc aac tac gtg agc acc      960
Tyr Gly Asn Asp Ser Phe Asn Tyr Trp Ser Gly Asn Tyr Val Ser Thr
305                 310                 315                 320 cgc ccc agc atc ggc agc aac gac atc atc acc agc ccc ttc tac ggc     1008
Arg Pro Ser Ile Gly Ser Asn Asp Ile Ile Thr Ser Pro Phe Tyr Gly
                325                 330                 335 aac aag agc agc gag ccc gtg cag aac ctt gag ttc aac ggc gag aag     1056
Asn Lys Ser Ser Glu Pro Val Gln Asn Leu Glu Phe Asn Gly Glu Lys
            340                 345                 350 gtg tac cgc gcc gtg gct aac acc aac ctg gcc gtg tgg ccc tct gca     1104
Val Tyr Arg Ala Val Ala Asn Thr Asn Leu Ala Val Trp Pro Ser Ala
        355                 360                 365 gtg tac agc ggc gtg acc aag gtg gag ttc agc cag tac aac gac cag     1152
Val Tyr Ser Gly Val Thr Lys Val Glu Phe Ser Gln Tyr Asn Asp Gln
370                 375                 380 acc gac gag gcc agc acc cag acc tac gac agc aag cgc aac gtg ggc     1200
Thr Asp Glu Ala Ser Thr Gln Thr Tyr Asp Ser Lys Arg Asn Val Gly
385                 390                 395                 400 gcc gtg agc tgg gac agc atc gac cag ctg ccc ccc gag acc acc gac     1248
Ala Val Ser Trp Asp Ser Ile Asp Gln Leu Pro Pro Glu Thr Thr Asp
                405                 410                 415 gag ccc ctg gag aag ggc tac agc cac cag ctg aac tac gtg atg tgc     1296
Glu Pro Leu Glu Lys Gly Tyr Ser His Gln Leu Asn Tyr Val Met Cys
            420                 425                 430 ttc ctg atg cag ggc agc cgc ggc acc atc ccc gtg ctg acc tgg acc     1344
Phe Leu Met Gln Gly Ser Arg Gly Thr Ile Pro Val Leu Thr Trp Thr
        435                 440                 445 cac aag agc gtc gac ttc ttc aac atg atc gac agc aag aag atc acc     1392
His Lys Ser Val Asp Phe Phe Asn Met Ile Asp Ser Lys Lys Ile Thr
450                 455                 460 cag ctg ccc ctg gtg aag gcc tac aag ctc cag agc ggc gcc agc gtg     1440
Gln Leu Pro Leu Val Lys Ala Tyr Lys Leu Gln Ser Gly Ala Ser Val
465                 470                 475                 480 gtg gca ggc ccc cgc ttc acc ggc ggc gac atc atc cag tgc acc gag     1488
Val Ala Gly Pro Arg Phe Thr Gly Gly Asp Ile Ile Gln Cys Thr Glu
                485                 490                 495 aac ggc agc gcc gcc acc atc tac gtg acc ccc gac gtg agc tac agc     1536
Asn Gly Ser Ala Ala Thr Ile Tyr Val Thr Pro Asp Val Ser Tyr Ser
            500                 505                 510 cag aag tac cgc gcc cgc atc cac tac gcc agc acc agc cag atc acc     1584
Gln Lys Tyr Arg Ala Arg Ile His Tyr Ala Ser Thr Ser Gln Ile Thr
        515                 520                 525 ttc acc ctg agc ctg gac ggg gcc ccc ttc aac caa tac tac ttc gac     1632
Phe Thr Leu Ser Leu Asp Gly Ala Pro Phe Asn Gln Tyr Tyr Phe Asp
530                 535                 540 aag acc atc aac aag ggc gac acc ctg acc tac aac agc ttc aac ctg     1680
Lys Thr Ile Asn Lys Gly Asp Thr Leu Thr Tyr Asn Ser Phe Asn Leu
545                 550                 555                 560 gcc agc ttc agc acc cct ttc gag ctg agc ggc aac aac ctc cag atc     1728
Ala Ser Phe Ser Thr Pro Phe Glu Leu Ser Gly Asn Asn Leu Gln Ile
                565                 570                 575 ggc gtg acc ggc ctg agc gcc ggc gac aag gtg tac atc gac aag atc     1776
Gly Val Thr Gly Leu Ser Ala Gly Asp Lys Val Tyr Ile Asp Lys Ile
            580                 585                 590 gag ttc atc ccc gtg aac tag atc tga gct c                           1807
Glu Phe Ile Pro Val Asn     Ile     Ala
        595                         600
```

```
<210> SEQ ID NO 9
<211> LENGTH: 598
<212> TYPE: PRT
<213> ORGANISM: Artificial Sequence
<220> FEATURE:
<221> NAME/KEY: misc_feature
<222> LOCATION: (108)..(111)
<223> OTHER INFORMATION: Cathepsin G recognition sequence.

<400> SEQUENCE: 9

Met Thr Ala Asp Asn Asn Thr Glu Ala Leu Asp Ser Ser Thr Thr Lys
  1               5                  10                  15

Asp Val Ile Gln Lys Gly Ile Ser Val Val Gly Asp Leu Leu Gly Val
             20                  25                  30

Val Gly Phe Pro Phe Gly Gly Ala Leu Val Ser Phe Tyr Thr Asn Phe
         35                  40                  45

Leu Asn Thr Ile Trp Pro Ser Glu Asp Pro Trp Lys Ala Phe Met Glu
 50                  55                  60

Gln Val Glu Ala Leu Met Asp Gln Lys Ile Ala Asp Tyr Ala Lys Asn
 65                  70                  75                  80

Lys Ala Leu Ala Glu Leu Gln Gly Leu Gln Asn Asn Val Glu Asp Tyr
                 85                  90                  95

Val Ser Ala Leu Ser Ser Trp Gln Lys Asn Pro Ala Ala Pro Phe Arg
            100                 105                 110

Asn Pro His Ser Gln Gly Arg Ile Arg Glu Leu Phe Ser Gln Ala Glu
            115                 120                 125

Ser His Phe Arg Asn Ser Met Pro Ser Phe Ala Ile Ser Gly Tyr Glu
        130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                165                 170                 175

Glu Asp Ile Ala Glu Phe Tyr Lys Arg Gln Leu Lys Leu Thr Gln Glu
            180                 185                 190

Tyr Thr Asp His Cys Val Lys Trp Tyr Asn Val Gly Leu Asp Lys Leu
        195                 200                 205

Arg Gly Ser Ser Tyr Glu Ser Trp Val Asn Phe Asn Arg Tyr Arg Arg
210                 215                 220

Glu Met Thr Leu Thr Val Leu Asp Leu Ile Ala Leu Phe Pro Leu Tyr
225                 230                 235                 240

Asp Val Arg Leu Tyr Pro Lys Glu Val Lys Thr Glu Leu Thr Arg Asp
                245                 250                 255

Val Leu Thr Asp Pro Ile Val Gly Val Asn Asn Leu Arg Gly Tyr Gly
            260                 265                 270

Thr Thr Phe Ser Asn Ile Glu Asn Tyr Ile Arg Lys Pro His Leu Phe
        275                 280                 285

Asp Tyr Leu His Arg Ile Gln Phe His Thr Arg Phe Gln Pro Gly Tyr
    290                 295                 300

Tyr Gly Asn Asp Ser Phe Asn Tyr Trp Ser Gly Asn Tyr Val Ser Thr
305                 310                 315                 320

Arg Pro Ser Ile Gly Ser Asn Asp Ile Ile Thr Ser Pro Phe Tyr Gly
                325                 330                 335

Asn Lys Ser Ser Glu Pro Val Gln Asn Leu Glu Phe Asn Gly Glu Lys
            340                 345                 350

Val Tyr Arg Ala Val Ala Asn Thr Asn Leu Ala Val Trp Pro Ser Ala
```

```
                355                 360                 365
Val Tyr Ser Gly Val Thr Lys Val Glu Phe Ser Gln Tyr Asn Asp Gln
    370                 375                 380

Thr Asp Glu Ala Ser Thr Gln Thr Tyr Asp Ser Lys Arg Asn Val Gly
385                 390                 395                 400

Ala Val Ser Trp Asp Ser Ile Asp Gln Leu Pro Pro Glu Thr Thr Asp
                405                 410                 415

Glu Pro Leu Glu Lys Gly Tyr Ser His Gln Leu Asn Tyr Val Met Cys
                420                 425                 430

Phe Leu Met Gln Gly Ser Arg Gly Thr Ile Pro Val Leu Thr Trp Thr
            435                 440                 445

His Lys Ser Val Asp Phe Phe Asn Met Ile Asp Ser Lys Lys Ile Thr
        450                 455                 460

Gln Leu Pro Leu Val Lys Ala Tyr Lys Leu Gln Ser Gly Ala Ser Val
465                 470                 475                 480

Val Ala Gly Pro Arg Phe Thr Gly Gly Asp Ile Ile Gln Cys Thr Glu
                485                 490                 495

Asn Gly Ser Ala Ala Thr Ile Tyr Val Thr Pro Asp Val Ser Tyr Ser
                500                 505                 510

Gln Lys Tyr Arg Ala Arg Ile His Tyr Ala Ser Thr Ser Gln Ile Thr
            515                 520                 525

Phe Thr Leu Ser Leu Asp Gly Ala Pro Phe Asn Gln Tyr Tyr Phe Asp
        530                 535                 540

Lys Thr Ile Asn Lys Gly Asp Thr Leu Thr Tyr Asn Ser Phe Asn Leu
545                 550                 555                 560

Ala Ser Phe Ser Thr Pro Phe Glu Leu Ser Gly Asn Asn Leu Gln Ile
                565                 570                 575

Gly Val Thr Gly Leu Ser Ala Gly Asp Lys Val Tyr Ile Asp Lys Ile
                580                 585                 590

Glu Phe Ile Pro Val Asn
            595
```

<210> SEQ ID NO 10
<211> LENGTH: 1818
<212> TYPE: DNA
<213> ORGANISM: Artificial Sequence
<220> FEATURE:
<221> NAME/KEY: CDS
<222> LOCATION: (1)..(1818)
<223> OTHER INFORMATION: Maize optimized modified cry3A085 coding
      sequence.
<220> FEATURE:
<221> NAME/KEY: misc_feature
<222> LOCATION: (346)..(357)
<223> OTHER INFORMATION: Cathepsin G recognition site coding sequence.

<400> SEQUENCE: 10

```
atg aac tac aag gag ttc ctc cgc atg ac

```
                                                           -continued gac ccc tgg aag gcc ttc atg gag cag gtg gag gcc ctg atg gac cag        240
Asp Pro Trp Lys Ala Phe Met Glu Gln Val Glu Ala Leu Met Asp Gln
 65              70                  75                  80 aag atc gcc gac tac gcc aag aac aag gca ctg gcc gag cta cag ggc        288
Lys Ile Ala Asp Tyr Ala Lys Asn Lys Ala Leu Ala Glu Leu Gln Gly
                 85                  90                  95 ctc cag aac aac gtg gag gac tat gtg agc gcc ctg agc agc tgg cag        336
Leu Gln Asn Asn Val Glu Asp Tyr Val Ser Ala Leu Ser Ser Trp Gln
            100                 105                 110 aag aac ccc gct gca ccg ttc cgc aac ccc cac agc cag ggc cgc atc        384
Lys Asn Pro Ala Ala Pro Phe Arg Asn Pro His Ser Gln Gly Arg Ile
        115                 120                 125 cgc gag ctg ttc agc cag gcc gag agc cac ttc cgc aac agc atg ccc        432
Arg Glu Leu Phe Ser Gln Ala Glu Ser His Phe Arg Asn Ser Met Pro
    130                 135                 140 agc ttc gcc atc agc ggc tac gag gtg ctg ttc ctg acc acc tac gcc        480
Ser Phe Ala Ile Ser Gly Tyr Glu Val Leu Phe Leu Thr Thr Tyr Ala
145                 150                 155                 160 cag gcc gcc aac acc cac ctg ttc ctg ctg aag gac gcc caa atc tac        528
Gln Ala Ala Asn Thr His Leu Phe Leu Leu Lys Asp Ala Gln Ile Tyr
                165                 170                 175 gga gag gag tgg ggc tac gag aag gag gac atc gcc gag ttc tac aag        576
Gly Glu Glu Trp Gly Tyr Glu Lys Glu Asp Ile Ala Glu Phe Tyr Lys
            180                 185                 190 cgc cag ctg aag ctg acc cag gag tac acc gac cac tgc gtg aag tgg        624
Arg Gln Leu Lys Leu Thr Gln Glu Tyr Thr Asp His Cys Val Lys Trp
        195                 200                 205 tac aac gtg ggt cta gac aag ctc cgc ggc agc agc tac gag agc tgg        672
Tyr Asn Val Gly Leu Asp Lys Leu Arg Gly Ser Ser Tyr Glu Ser Trp
    210                 215                 220 gtg aac ttc aac cgc tac cgc cgc gag atg acc ctg acc gtg ctg gac        720
Val Asn Phe Asn Arg Tyr Arg Arg Glu Met Thr Leu Thr Val Leu Asp
225                 230                 235                 240 ctg atc gcc ctg ttc ccc ctg tac gac gtg cgc ctg tac ccc aag gag        768
Leu Ile Ala Leu Phe Pro Leu Tyr Asp Val Arg Leu Tyr Pro Lys Glu
                245                 250                 255 gtg aag acc gag ctg acc cgc gac gtg ctg acc gac ccc atc gtg ggc        816
Val Lys Thr Glu Leu Thr Arg Asp Val Leu Thr Asp Pro Ile Val Gly
            260                 265                 270 gtg aac aac ctg cgc ggc tac ggc acc acc ttc agc aac atc gag aac        864
Val Asn Asn Leu Arg Gly Tyr Gly Thr Thr Phe Ser Asn Ile Glu Asn
        275                 280                 285 tac atc cgc aag ccc cac ctg ttc gac tac ctg cac cgc atc cag ttc        912
Tyr Ile Arg Lys Pro His Leu Phe Asp Tyr Leu His Arg Ile Gln Phe
    290                 295                 300 cac acg cgt ttc cag ccc ggc tac tac ggc aac gac agc ttc aac tac        960
His Thr Arg Phe Gln Pro Gly Tyr Tyr Gly Asn Asp Ser Phe Asn Tyr
305                 310                 315                 320 tgg agc ggc aac tac gtg agc acc cgc ccc agc atc ggc agc aac gac       1008
Trp Ser Gly Asn Tyr Val Ser Thr Arg Pro Ser Ile Gly Ser Asn Asp
                325                 330                 335 atc atc acc agc ccc ttc tac ggc aac aag agc agc gag ccc gtg cag       1056
Ile Ile Thr Ser Pro Phe Tyr Gly Asn Lys Ser Ser Glu Pro Val Gln
            340                 345                 350 aac ctt gag ttc aac ggc gag aag gtg tac cgc gcc gtg gct aac acc       1104
Asn Leu Glu Phe Asn Gly Glu Lys Val Tyr Arg Ala Val Ala Asn Thr
        355                 360                 365 aac ctg gcc gtg tgg ccc tct gca gtg tac agc ggc gtg acc aag gtg       1152
Asn Leu Ala Val Trp Pro Ser Ala Val Tyr Ser Gly Val Thr Lys Val
```

|  |  |  |  |  |  |  |  |  |  |  |  |  |  |  |  |
|---|---|---|---|---|---|---|---|---|---|---|---|---|---|---|---|
| | | | 370 | | | | 375 | | | | 380 | | | | |
| gag | ttc | agc | cag | tac | aac | gac | cag | acc | gac | gag | gcc | agc | acc | cag | acc | 1200
| Glu | Phe | Ser | Gln | Tyr | Asn | Asp | Gln | Thr | Asp | Glu | Ala | Ser | Thr | Gln | Thr |
| 385 | | | | 390 | | | | 395 | | | | 400 | | | | tac gac agc aag cgc aac gtg ggc gcc gtg agc tgg gac agc atc gac   1248
Tyr Asp Ser Lys Arg Asn Val Gly Ala Val Ser Trp Asp Ser Ile Asp
            405                 410                 415 cag ctg ccc ccc gag acc acc gac gag ccc ctg gag aag ggc tac agc   1296
Gln Leu Pro Pro Glu Thr Thr Asp Glu Pro Leu Glu Lys Gly Tyr Ser
        420                 425                 430 cac cag ctg aac tac gtg atg tgc ttc ctg atg cag ggc agc cgc ggc   1344
His Gln Leu Asn Tyr Val Met Cys Phe Leu Met Gln Gly Ser Arg Gly
    435                 440                 445 acc atc ccc gtg ctg acc tgg acc cac aag agc gtc gac ttc ttc aac   1392
Thr Ile Pro Val Leu Thr Trp Thr His Lys Ser Val Asp Phe Phe Asn
450                 455                 460 atg atc gac agc aag aag atc acc cag ctg ccc ctg gtg aag gcc tac   1440
Met Ile Asp Ser Lys Lys Ile Thr Gln Leu Pro Leu Val Lys Ala Tyr
465                 470                 475                 480 aag ctc cag agc ggc gcc agc gtg gtg gca ggc ccc cgc ttc acc ggc   1488
Lys Leu Gln Ser Gly Ala Ser Val Val Ala Gly Pro Arg Phe Thr Gly
            485                 490                 495 ggc gac atc atc cag tgc acc gag aac ggc agc gcc gcc acc atc tac   1536
Gly Asp Ile Ile Gln Cys Thr Glu Asn Gly Ser Ala Ala Thr Ile Tyr
        500                 505                 510 gtg acc ccc gac gtg agc tac agc cag aag tac cgc gcc cgc atc cac   1584
Val Thr Pro Asp Val Ser Tyr Ser Gln Lys Tyr Arg Ala Arg Ile His
    515                 520                 525 tac gcc agc acc agc cag atc acc ttc acc ctg agc ctg gac ggg gcc   1632
Tyr Ala Ser Thr Ser Gln Ile Thr Phe Thr Leu Ser Leu Asp Gly Ala
530                 535                 540 ccc ttc aac caa tac tac ttc gac aag acc atc aac aag ggc gac acc   1680
Pro Phe Asn Gln Tyr Tyr Phe Asp Lys Thr Ile Asn Lys Gly Asp Thr
545                 550                 555                 560 ctg acc tac aac agc ttc aac ctg gcc agc ttc agc acc cct ttc gag   1728
Leu Thr Tyr Asn Ser Phe Asn Leu Ala Ser Phe Ser Thr Pro Phe Glu
            565                 570                 575 ctg agc ggc aac aac ctc cag atc ggc gtg acc ggc ctg agc gcc ggc   1776
Leu Ser Gly Asn Asn Leu Gln Ile Gly Val Thr Gly Leu Ser Ala Gly
        580                 585                 590 gac aag gtg tac atc gac aag atc gag ttc atc ccc gtg aac           1818
Asp Lys Val Tyr Ile Asp Lys Ile Glu Phe Ile Pro Val Asn
    595                 600                 605

<210> SEQ ID NO 11
<211> LENGTH: 606
<212> TYPE: PRT
<213> ORGANISM: Artificial Sequence
<220> FEATURE:
<221> NAME/KEY: misc_feature
<222> LOCATION: (116)..(119)
<223> OTHER INFORMATION: Cathepsin G recognition sequence.

<400> SEQUENCE: 11

Met Asn Tyr Lys Glu Phe Leu Arg Met Thr Ala Asp Asn Asn Thr Glu
1               5                   10                  15

Ala Leu Asp Ser Ser Thr Thr Lys Asp Val Ile Gln Lys Gly Ile Ser
            20                  25                  30

Val Val Gly Asp Leu Leu Gly Val Val Gly Phe Pro Phe Gly Gly Ala
        35                  40                  45

```
Leu Val Ser Phe Tyr Thr Asn Phe Leu Asn Thr Ile Trp Pro Ser Glu
 50                  55                  60

Asp Pro Trp Lys Ala Phe Met Glu Gln Val Glu Ala Leu Met Asp Gln
 65                  70                  75                  80

Lys Ile Ala Asp Tyr Ala Lys Asn Lys Ala Leu Ala Glu Leu Gln Gly
                 85                  90                  95

Leu Gln Asn Asn Val Glu Asp Tyr Val Ser Ala Leu Ser Ser Trp Gln
             100                 105                 110

Lys Asn Pro Ala Ala Pro Phe Arg Asn Pro His Ser Gln Gly Arg Ile
         115                 120                 125

Arg Glu Leu Phe Ser Gln Ala Glu Ser His Phe Arg Asn Ser Met Pro
     130                 135                 140

Ser Phe Ala Ile Ser Gly Tyr Glu Val Leu Phe Leu Thr Thr Tyr Ala
145                 150                 155                 160

Gln Ala Ala Asn Thr His Leu Phe Leu Leu Lys Asp Ala Gln Ile Tyr
                165                 170                 175

Gly Glu Glu Trp Gly Tyr Glu Lys Glu Asp Ile Ala Glu Phe Tyr Lys
            180                 185                 190

Arg Gln Leu Lys Leu Thr Gln Glu Tyr Thr Asp His Cys Val Lys Trp
        195                 200                 205

Tyr Asn Val Gly Leu Asp Lys Leu Arg Gly Ser Ser Tyr Glu Ser Trp
    210                 215                 220

Val Asn Phe Asn Arg Tyr Arg Arg Glu Met Thr Leu Thr Val Leu Asp
225                 230                 235                 240

Leu Ile Ala Leu Phe Pro Leu Tyr Asp Val Arg Leu Tyr Pro Lys Glu
                245                 250                 255

Val Lys Thr Glu Leu Thr Arg Asp Val Leu Thr Asp Pro Ile Val Gly
            260                 265                 270

Val Asn Asn Leu Arg Gly Tyr Gly Thr Thr Phe Ser Asn Ile Glu Asn
        275                 280                 285

Tyr Ile Arg Lys Pro His Leu Phe Asp Tyr Leu His Arg Ile Gln Phe
    290                 295                 300

His Thr Arg Phe Gln Pro Gly Tyr Tyr Gly Asn Asp Ser Phe Asn Tyr
305                 310                 315                 320

Trp Ser Gly Asn Tyr Val Ser Thr Arg Pro Ser Ile Gly Ser Asn Asp
                325                 330                 335

Ile Ile Thr Ser Pro Phe Tyr Gly Asn Lys Ser Ser Glu Pro Val Gln
            340                 345                 350

Asn Leu Glu Phe Asn Gly Glu Lys Val Tyr Arg Ala Val Ala Asn Thr
        355                 360                 365

Asn Leu Ala Val Trp Pro Ser Ala Val Tyr Ser Gly Val Thr Lys Val
    370                 375                 380

Glu Phe Ser Gln Tyr Asn Asp Gln Thr Asp Glu Ala Ser Thr Gln Thr
385                 390                 395                 400

Tyr Asp Ser Lys Arg Asn Val Gly Ala Val Ser Trp Asp Ser Ile Asp
                405                 410                 415

Gln Leu Pro Pro Glu Thr Thr Asp Glu Pro Leu Glu Lys Gly Tyr Ser
            420                 425                 430

His Gln Leu Asn Tyr Val Met Cys Phe Leu Met Gln Gly Ser Arg Gly
        435                 440                 445

Thr Ile Pro Val Leu Thr Trp Thr His Lys Ser Val Asp Phe Phe Asn
450                 455                 460

Met Ile Asp Ser Lys Lys Ile Thr Gln Leu Pro Leu Val Lys Ala Tyr
```

-continued

```
           465                 470                 475                 480
Lys Leu Gln Ser Gly Ala Ser Val Val Ala Gly Pro Arg Phe Thr Gly
                485                 490                 495

Gly Asp Ile Ile Gln Cys Thr Glu Asn Gly Ser Ala Ala Thr Ile Tyr
            500                 505                 510

Val Thr Pro Asp Val Ser Tyr Ser Gln Lys Tyr Arg Ala Arg Ile His
            515                 520                 525

Tyr Ala Ser Thr Ser Gln Ile Thr Phe Thr Leu Ser Leu Asp Gly Ala
        530                 535                 540

Pro Phe Asn Gln Tyr Tyr Phe Asp Lys Thr Ile Asn Lys Gly Asp Thr
545                 550                 555                 560

Leu Thr Tyr Asn Ser Phe Asn Leu Ala Ser Phe Ser Thr Pro Phe Glu
                565                 570                 575

Leu Ser Gly Asn Asn Leu Gln Ile Gly Val Thr Gly Leu Ser Ala Gly
            580                 585                 590

Asp Lys Val Tyr Ile Asp Lys Ile Glu Phe Ile Pro Val Asn
            595                 600                 605

<210> SEQ ID NO 12
<211> LENGTH: 1794
<212> TYPE: DNA
<213> ORGANISM: Artificial Sequence
<220> FEATURE:
<221> NAME/KEY: CDS
<222> LOCATION: (1)..(1794)
<223> OTHER INFORMATION: Maize optimized modified cry3A082 coding
      sequence.
<220> FEATURE:
<221> NAME/KEY: misc_feature
<222> LOCATION: (1609)..(1620)
<223> OTHER INFORMATION: Cathepsin G recognition site coding sequence

<400> SEQUENCE: 12 atg acg gcc gac aac aac acc gag gcc ctg gac agc agc acc acc aag      48
Met Thr Ala Asp Asn Asn Thr Glu Ala Leu Asp Ser Ser Thr Thr Lys
1               5                   10                  15 gac gtg atc cag aag ggc atc agc gtg gtg ggc gac ctg ctg ggc gtg      96
Asp Val Ile Gln Lys Gly Ile Ser Val Val Gly Asp Leu Leu Gly Val
            20                  25                  30 gtg ggc ttc ccc ttc ggc ggc gcc ctg gtg agc ttc tac acc aac ttc     144
Val Gly Phe Pro Phe Gly Gly Ala Leu Val Ser Phe Tyr Thr Asn Phe
        35                  40                  45 ctg aac acc atc tgg ccc agc gag gac ccc tgg aag gcc ttc atg gag     192
Leu Asn Thr Ile Trp Pro Ser Glu Asp Pro Trp Lys Ala Phe Met Glu
    50                  55                  60 cag gtg gag gcc ctg atg gac cag aag atc gcc gac tac gcc aag aac     240
Gln Val Glu Ala Leu Met Asp Gln Lys Ile Ala Asp Tyr Ala Lys Asn
65                  70                  75                  80 aag gca ctg gcc gag cta cag ggc ctc cag aac aac gtg gag gac tat     288
Lys Ala Leu Ala Glu Leu Gln Gly Leu Gln Asn Asn Val Glu Asp Tyr
                85                  90                  95 gtg agc gcc ctg agc agc tgg cag aag aac ccc gtc tcg agc cgc aac     336
Val Ser Ala Leu Ser Ser Trp Gln Lys Asn Pro Val Ser Ser Arg Asn
            100                 105                 110 ccc cac agc cag ggc cgc atc cgc gag ctg ttc agc cag gcc gag agc     384
Pro His Ser Gln Gly Arg Ile Arg Glu Leu Phe Ser Gln Ala Glu Ser
        115                 120                 125 cac ttc cgc aac agc atg ccc agc ttc gcc atc agc ggc tac gag gtg     432
His Phe Arg Asn Ser Met Pro Ser Phe Ala Ile Ser Gly Tyr Glu Val
    130                 135                 140
```

-continued

| | |
|---|---|
| ctg ttc ctg acc acc tac gcc cag gcc gcc aac acc cac ctg ttc ctg<br>Leu Phe Leu Thr Thr Tyr Ala Gln Ala Ala Asn Thr His Leu Phe Leu<br>145                150                  155                160 | 480 |
| ctg aag gac gcc caa atc tac gga gag gag tgg ggc tac gag aag gag<br>Leu Lys Asp Ala Gln Ile Tyr Gly Glu Glu Trp Gly Tyr Glu Lys Glu<br>                165                  170                  175 | 528 |
| gac atc gcc gag ttc tac aag cgc cag ctg aag ctg acc cag gag tac<br>Asp Ile Ala Glu Phe Tyr Lys Arg Gln Leu Lys Leu Thr Gln Glu Tyr<br>        180                  185                  190 | 576 |
| acc gac cac tgc gtg aag tgg tac aac gtg ggt cta gac aag ctc cgc<br>Thr Asp His Cys Val Lys Trp Tyr Asn Val Gly Leu Asp Lys Leu Arg<br>              195                  200                  205 | 624 |
| ggc agc agc tac gag agc tgg gtg aac ttc aac cgc tac cgc cgc gag<br>Gly Ser Ser Tyr Glu Ser Trp Val Asn Phe Asn Arg Tyr Arg Arg Glu<br>210                  215                  220 | 672 |
| atg acc ctg acc gtg ctg gac ctg atc gcc ctg ttc ccc ctg tac gac<br>Met Thr Leu Thr Val Leu Asp Leu Ile Ala Leu Phe Pro Leu Tyr Asp<br>225                230                  235                240 | 720 |
| gtg cgc ctg tac ccc aag gag gtg aag acc gag ctg acc cgc gac gtg<br>Val Arg Leu Tyr Pro Lys Glu Val Lys Thr Glu Leu Thr Arg Asp Val<br>                  245                  250                  255 | 768 |
| ctg acc gac ccc atc gtg ggc gtg aac aac ctg cgc ggc tac ggc acc<br>Leu Thr Asp Pro Ile Val Gly Val Asn Asn Leu Arg Gly Tyr Gly Thr<br>            260                  265                  270 | 816 |
| acc ttc agc aac atc gag aac tac atc cgc aag ccc cac ctg ttc gac<br>Thr Phe Ser Asn Ile Glu Asn Tyr Ile Arg Lys Pro His Leu Phe Asp<br>              275                  280                  285 | 864 |
| tac ctg cac cgc atc cag ttc cac acg cgt ttc cag ccc ggc tac tac<br>Tyr Leu His Arg Ile Gln Phe His Thr Arg Phe Gln Pro Gly Tyr Tyr<br>290                  295                  300 | 912 |
| ggc aac gac agc ttc aac tac tgg agc ggc aac tac gtg agc acc cgc<br>Gly Asn Asp Ser Phe Asn Tyr Trp Ser Gly Asn Tyr Val Ser Thr Arg<br>305                310                  315                320 | 960 |
| ccc agc atc ggc agc aac gac atc atc acc agc ccc ttc tac ggc aac<br>Pro Ser Ile Gly Ser Asn Asp Ile Ile Thr Ser Pro Phe Tyr Gly Asn<br>                  325                  330                  335 | 1008 |
| aag agc agc gag ccc gtg cag aac ctt gag ttc aac ggc gag aag gtg<br>Lys Ser Ser Glu Pro Val Gln Asn Leu Glu Phe Asn Gly Glu Lys Val<br>              340                  345                  350 | 1056 |
| tac cgc gcc gtg gct aac acc aac ctg gcc gtg tgg ccc tct gca gtg<br>Tyr Arg Ala Val Ala Asn Thr Asn Leu Ala Val Trp Pro Ser Ala Val<br>        355                  360                  365 | 1104 |
| tac agc ggc gtg acc aag gtg gag ttc agc cag tac aac gac cag acc<br>Tyr Ser Gly Val Thr Lys Val Glu Phe Ser Gln Tyr Asn Asp Gln Thr<br>370                  375                  380 | 1152 |
| gac gag gcc agc acc cag acc tac gac agc aag cgc aac gtg ggc gcc<br>Asp Glu Ala Ser Thr Gln Thr Tyr Asp Ser Lys Arg Asn Val Gly Ala<br>385                390                  395                400 | 1200 |
| gtg agc tgg gac agc atc gac cag ctg ccc ccc gag acc acc gac gag<br>Val Ser Trp Asp Ser Ile Asp Gln Leu Pro Pro Glu Thr Thr Asp Glu<br>                  405                  410                  415 | 1248 |
| ccc ctg gag aag ggc tac agc cac cag ctg aac tac gtg atg tgc ttc<br>Pro Leu Glu Lys Gly Tyr Ser His Gln Leu Asn Tyr Val Met Cys Phe<br>                  420                  425                  430 | 1296 |
| ctg atg cag ggc agc cgc ggc acc atc ccc gtg ctg acc tgg acc cac<br>Leu Met Gln Gly Ser Arg Gly Thr Ile Pro Val Leu Thr Trp Thr His<br>            435                  440                  445 | 1344 |
| aag agc gtc gac ttc ttc aac atg atc gac agc aag aag atc acc cag<br>Lys Ser Val Asp Phe Phe Asn Met Ile Asp Ser Lys Lys Ile Thr Gln<br>450                  455                  460 | 1392 |

-continued

```
ctg ccc ctg gtg aag gcc tac aag ctc cag agc ggc gcc agc gtg gtg      1440
Leu Pro Leu Val Lys Ala Tyr Lys Leu Gln Ser Gly Ala Ser Val Val
465                 470                 475                 480 gca ggc ccc cgc ttc acc ggc ggc gac atc atc cag tgc acc gag aac      1488
Ala Gly Pro Arg Phe Thr Gly Gly Asp Ile Ile Gln Cys Thr Glu Asn
                485                 490                 495 ggc agc gcc gcc acc atc tac gtg acc ccc gac gtg agc tac agc cag      1536
Gly Ser Ala Ala Thr Ile Tyr Val Thr Pro Asp Val Ser Tyr Ser Gln
            500                 505                 510 aag tac cgc gcc cgc atc cac tac gcc agc acc agc cag atc acc ttc      1584
Lys Tyr Arg Ala Arg Ile His Tyr Ala Ser Thr Ser Gln Ile Thr Phe
        515                 520                 525 acc ctg agc ctg gac ggg gcc ccc gct gca ccg ttc tac ttc gac aag      1632
Thr Leu Ser Leu Asp Gly Ala Pro Ala Ala Pro Phe Tyr Phe Asp Lys
    530                 535                 540 acc atc aac aag ggc gac acc ctg acc tac aac agc ttc aac ctg gcc      1680
Thr Ile Asn Lys Gly Asp Thr Leu Thr Tyr Asn Ser Phe Asn Leu Ala
545                 550                 555                 560 agc ttc agc acc cct ttc gag ctg agc ggc aac aac ctc cag atc ggc      1728
Ser Phe Ser Thr Pro Phe Glu Leu Ser Gly Asn Asn Leu Gln Ile Gly
                565                 570                 575 gtg acc ggc ctg agc gcc ggc gac aag gtg tac atc gac aag atc gag      1776
Val Thr Gly Leu Ser Ala Gly Asp Lys Val Tyr Ile Asp Lys Ile Glu
            580                 585                 590 ttc atc ccc gtg aac tag                                              1794
Phe Ile Pro Val Asn
        595
```

<210> SEQ ID NO 13
<211> LENGTH: 597
<212> TYPE: PRT
<213> ORGANISM: Artificial Sequence
<220> FEATURE:
<221> NAME/KEY: misc_feature
<222> LOCATION: (537)..(540)
<223> OTHER INFORMATION: Cathepsin G recognition sequence

<400> SEQUENCE: 13

```
Met Thr Ala Asp Asn Thr Glu Ala Leu Asp Ser Ser Thr Thr Lys
1               5                   10                  15

Asp Val Ile Gln Lys Gly Ile Ser Val Val Gly Asp Leu Leu Gly Val
                20                  25                  30

Val Gly Phe Pro Phe Gly Gly Ala Leu Val Ser Phe Tyr Thr Asn Phe
            35                  40                  45

Leu Asn Thr Ile Trp Pro Ser Glu Asp Pro Trp Lys Ala Phe Met Glu
        50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Val Ser Ser Arg Asn
            100                 105                 110

Pro His Ser Gln Gly Arg Ile Arg Glu Leu Phe Ser Gln Ala Glu Ser
        115                 120                 125

His Phe Arg Asn Ser Met Pro Ser Phe Ala Ile Ser Gly Tyr Glu Val
    130                 135                 140

Leu Phe Leu Thr Thr Tyr Ala Gln Ala Ala Asn Thr His Leu Phe Leu
145                 150                 155                 160
```

-continued

```
Leu Lys Asp Ala Gln Ile Tyr Gly Glu Glu Trp Gly Tyr Glu Lys Glu
            165                 170                 175

Asp Ile Ala Glu Phe Tyr Lys Arg Gln Leu Lys Leu Thr Gln Glu Tyr
            180                 185                 190

Thr Asp His Cys Val Lys Trp Tyr Asn Val Gly Leu Asp Lys Leu Arg
            195                 200                 205

Gly Ser Ser Tyr Glu Ser Trp Val Asn Phe Asn Arg Tyr Arg Arg Glu
210                 215                 220

Met Thr Leu Thr Val Leu Asp Leu Ile Ala Leu Phe Pro Leu Tyr Asp
225                 230                 235                 240

Val Arg Leu Tyr Pro Lys Glu Val Lys Thr Glu Leu Thr Arg Asp Val
                245                 250                 255

Leu Thr Asp Pro Ile Val Gly Val Asn Asn Leu Arg Gly Tyr Gly Thr
                260                 265                 270

Thr Phe Ser Asn Ile Glu Asn Tyr Ile Arg Lys Pro His Leu Phe Asp
            275                 280                 285

Tyr Leu His Arg Ile Gln Phe His Thr Arg Phe Gln Pro Gly Tyr Tyr
            290                 295                 300

Gly Asn Asp Ser Phe Asn Tyr Trp Ser Gly Asn Tyr Val Ser Thr Arg
305                 310                 315                 320

Pro Ser Ile Gly Ser Asn Asp Ile Ile Thr Ser Pro Phe Tyr Gly Asn
                325                 330                 335

Lys Ser Ser Glu Pro Val Gln Asn Leu Glu Phe Asn Gly Glu Lys Val
                340                 345                 350

Tyr Arg Ala Val Ala Asn Thr Asn Leu Ala Val Trp Pro Ser Ala Val
            355                 360                 365

Tyr Ser Gly Val Thr Lys Val Glu Phe Ser Gln Tyr Asn Asp Gln Thr
            370                 375                 380

Asp Glu Ala Ser Thr Gln Thr Tyr Asp Ser Lys Arg Asn Val Gly Ala
385                 390                 395                 400

Val Ser Trp Asp Ser Ile Asp Gln Leu Pro Pro Glu Thr Thr Asp Glu
                405                 410                 415

Pro Leu Glu Lys Gly Tyr Ser His Gln Leu Asn Tyr Val Met Cys Phe
                420                 425                 430

Leu Met Gln Gly Ser Arg Gly Thr Ile Pro Val Leu Thr Trp Thr His
            435                 440                 445

Lys Ser Val Asp Phe Phe Asn Met Ile Asp Ser Lys Lys Ile Thr Gln
            450                 455                 460

Leu Pro Leu Val Lys Ala Tyr Lys Leu Gln Ser Gly Ala Ser Val Val
465                 470                 475                 480

Ala Gly Pro Arg Phe Thr Gly Gly Asp Ile Ile Gln Cys Thr Glu Asn
                485                 490                 495

Gly Ser Ala Ala Thr Ile Tyr Val Thr Pro Asp Val Ser Tyr Ser Gln
                500                 505                 510

Lys Tyr Arg Ala Arg Ile His Tyr Ala Ser Thr Ser Gln Ile Thr Phe
            515                 520                 525

Thr Leu Ser Leu Asp Gly Ala Pro Ala Pro Phe Tyr Phe Asp Lys
            530                 535                 540

Thr Ile Asn Lys Gly Asp Thr Leu Thr Tyr Asn Ser Phe Asn Leu Ala
545                 550                 555                 560

Ser Phe Ser Thr Pro Phe Glu Leu Ser Gly Asn Asn Leu Gln Ile Gly
                565                 570                 575

Val Thr Gly Leu Ser Ala Gly Asp Lys Val Tyr Ile Asp Lys Ile Glu
```

-continued

```
                 580                 585                 590

Phe Ile Pro Val Asn
        595

<210> SEQ ID NO 14
<211> LENGTH: 1816
<212> TYPE: DNA
<213> ORGANISM: Artificial Sequence
<220> FEATURE:
<221> NAME/KEY: CDS
<222> LOCATION: (1)..(1812)
<223> OTHER INFORMATION: Maize optimized  modified cry3A058 coding
      sequence.
<220> FEATURE:
<221> NAME/KEY: misc_feature
<222> LOCATION: (1621)..(1632)
<223> OTHER INFORMATION: Cathepsin G recognition site coding sequence

<400> SEQUENCE: 14 atg acg gcc gac aac aac acc gag gcc ctg gac agc agc acc acc aag        48
Met Thr Ala Asp Asn Asn Thr Glu Ala Leu Asp Ser Ser Thr Thr Lys
1               5                   10                  15 gac gtg atc cag aag ggc atc agc gtg gtg ggc gac ctg ctg ggc gtg        96
Asp Val Ile Gln Lys Gly Ile Ser Val Val Gly Asp Leu Leu Gly Val
            20                  25                  30 gtg ggc ttc ccc ttc ggc ggc gcc ctg gtg agc ttc tac acc aac ttc       144
Val Gly Phe Pro Phe Gly Gly Ala Leu Val Ser Phe Tyr Thr Asn Phe
        35                  40                  45 ctg aac acc atc tgg ccc agc gag gac ccc tgg aag gcc ttc atg gag       192
Leu Asn Thr Ile Trp Pro Ser Glu Asp Pro Trp Lys Ala Phe Met Glu
    50                  55                  60 cag gtg gag gcc ctg atg gac cag aag atc gcc gac tac gcc aag aac       240
Gln Val Glu Ala Leu Met Asp Gln Lys Ile Ala Asp Tyr Ala Lys Asn
65                  70                  75                  80 aag gca ctg gcc gag cta cag ggc ctc cag aac aac gtg gag gac tat       288
Lys Ala Leu Ala Glu Leu Gln Gly Leu Gln Asn Asn Val Glu Asp Tyr
                85                  90                  95 gtg agc gcc ctg agc agc tgg cag aag aac ccc gtc tcg agc cgc aac       336
Val Ser Ala Leu Ser Ser Trp Gln Lys Asn Pro Val Ser Ser Arg Asn
            100                 105                 110 ccc cac agc cag ggc cgc atc cgc gag ctg ttc agc cag gcc gag agc       384
Pro His Ser Gln Gly Arg Ile Arg Glu Leu Phe Ser Gln Ala Glu Ser
        115                 120                 125 cac ttc cgc aac agc atg ccc agc ttc gcc atc agc ggc tac gag gtg       432
His Phe Arg Asn Ser Met Pro Ser Phe Ala Ile Ser Gly Tyr Glu Val
    130                 135                 140 ctg ttc ctg acc acc tac gcc cag gcc gcc aac acc cac ctg ttc ctg       480
Leu Phe Leu Thr Thr Tyr Ala Gln Ala Ala Asn Thr His Leu Phe Leu
145                 150                 155                 160 ctg aag gac gcc caa atc tac gga gag gag tgg ggc tac gag aag gag       528
Leu Lys Asp Ala Gln Ile Tyr Gly Glu Glu Trp Gly Tyr Glu Lys Glu
                165                 170                 175 gac atc gcc gag ttc tac aag cgc cag ctg aag ctg acc cag gag tac       576
Asp Ile Ala Glu Phe Tyr Lys Arg Gln Leu Lys Leu Thr Gln Glu Tyr
            180                 185                 190 acc gac cac tgc gtg aag tgg tac aac gtg ggt cta gac aag ctc cgc       624
Thr Asp His Cys Val Lys Trp Tyr Asn Val Gly Leu Asp Lys Leu Arg
        195                 200                 205 ggc agc agc tac gag agc tgg gtg aac ttc aac cgc tac cgc cgc gag       672
Gly Ser Ser Tyr Glu Ser Trp Val Asn Phe Asn Arg Tyr Arg Arg Glu
    210                 215                 220 atg acc ctg acc gtg ctg gac ctg atc gcc ctg ttc ccc ctg tac gac       720
```

```
Met Thr Leu Thr Val Leu Asp Leu Ile Ala Leu Phe Pro Leu Tyr Asp
225                 230                 235                 240 gtg cgc ctg tac ccc aag gag gtg aag acc gag ctg acc cgc gac gtg          768
Val Arg Leu Tyr Pro Lys Glu Val Lys Thr Glu Leu Thr Arg Asp Val
                245                 250                 255 ctg acc gac ccc atc gtg ggc gtg aac aac ctg cgc ggc tac ggc acc          816
Leu Thr Asp Pro Ile Val Gly Val Asn Asn Leu Arg Gly Tyr Gly Thr
                260                 265                 270 acc ttc agc aac atc gag aac tac atc cgc aag ccc cac ctg ttc gac          864
Thr Phe Ser Asn Ile Glu Asn Tyr Ile Arg Lys Pro His Leu Phe Asp
            275                 280                 285 tac ctg cac cgc atc cag ttc cac acg cgt ttc cag ccc ggc tac tac          912
Tyr Leu His Arg Ile Gln Phe His Thr Arg Phe Gln Pro Gly Tyr Tyr
        290                 295                 300 ggc aac gac agc ttc aac tac tgg agc ggc aac tac gtg agc acc cgc          960
Gly Asn Asp Ser Phe Asn Tyr Trp Ser Gly Asn Tyr Val Ser Thr Arg
305                 310                 315                 320 ccc agc atc ggc agc aac gac atc atc acc agc ccc ttc tac ggc aac         1008
Pro Ser Ile Gly Ser Asn Asp Ile Ile Thr Ser Pro Phe Tyr Gly Asn
                325                 330                 335 aag agc agc gag ccc gtg cag aac ctt gag ttc aac ggc gag aag gtg         1056
Lys Ser Ser Glu Pro Val Gln Asn Leu Glu Phe Asn Gly Glu Lys Val
                340                 345                 350 tac cgc gcc gtg gct aac acc aac ctg gcc gtg tgg ccc tct gca gtg         1104
Tyr Arg Ala Val Ala Asn Thr Asn Leu Ala Val Trp Pro Ser Ala Val
            355                 360                 365 tac agc ggc gtg acc aag gtg gag ttc agc cag tac aac gac cag acc         1152
Tyr Ser Gly Val Thr Lys Val Glu Phe Ser Gln Tyr Asn Asp Gln Thr
370                 375                 380 gac gag gcc agc acc cag acc tac gac agc aag cgc aac gtg ggc gcc         1200
Asp Glu Ala Ser Thr Gln Thr Tyr Asp Ser Lys Arg Asn Val Gly Ala
385                 390                 395                 400 gtg agc tgg gac agc atc gac cag ctg ccc ccc gag acc acc gac gag         1248
Val Ser Trp Asp Ser Ile Asp Gln Leu Pro Pro Glu Thr Thr Asp Glu
                405                 410                 415 ccc ctg gag aag ggc tac agc cac cag ctg aac tac gtg atg tgc ttc         1296
Pro Leu Glu Lys Gly Tyr Ser His Gln Leu Asn Tyr Val Met Cys Phe
            420                 425                 430 ctg atg cag ggc agc cgc ggc acc atc ccc gtg ctg acc tgg acc cac         1344
Leu Met Gln Gly Ser Arg Gly Thr Ile Pro Val Leu Thr Trp Thr His
        435                 440                 445 aag agc gtc gac ttc ttc aac atg atc gac agc aag aag atc acc cag         1392
Lys Ser Val Asp Phe Phe Asn Met Ile Asp Ser Lys Lys Ile Thr Gln
450                 455                 460 ctg ccc ctg gtg aag gcc tac aag ctc cag agc ggc gcc agc gtg gtg         1440
Leu Pro Leu Val Lys Ala Tyr Lys Leu Gln Ser Gly Ala Ser Val Val
465                 470                 475                 480 gca ggc ccc cgc ttc acc ggc ggc gac atc atc cag tgc acc gag aac         1488
Ala Gly Pro Arg Phe Thr Gly Gly Asp Ile Ile Gln Cys Thr Glu Asn
                485                 490                 495 ggc agc gcc gcc acc atc tac gtg acc ccc gac gtg agc tac agc cag         1536
Gly Ser Ala Ala Thr Ile Tyr Val Thr Pro Asp Val Ser Tyr Ser Gln
            500                 505                 510 aag tac cgc gcc cgc atc cac tac gcc agc acc agc cag atc acc ttc         1584
Lys Tyr Arg Ala Arg Ile His Tyr Ala Ser Thr Ser Gln Ile Thr Phe
        515                 520                 525 acc ctg agc ctg gac ggg gcc ccc ttc aac caa tac gct gca ccg ttc         1632
Thr Leu Ser Leu Asp Gly Ala Pro Phe Asn Gln Tyr Ala Ala Pro Phe
530                 535                 540
```

```
tac ttc gac aag acc atc aac aag ggc gac acc ctg acc tac aac agc    1680
Tyr Phe Asp Lys Thr Ile Asn Lys Gly Asp Thr Leu Thr Tyr Asn Ser
545                 550                 555                 560 ttc aac ctg gcc agc ttc agc acc cct ttc gag ctg agc ggc aac aac    1728
Phe Asn Leu Ala Ser Phe Ser Thr Pro Phe Glu Leu Ser Gly Asn Asn
            565                 570                 575 ctc cag atc ggc gtg acc ggc ctg agc gcc ggc gac aag gtg tac atc    1776
Leu Gln Ile Gly Val Thr Gly Leu Ser Ala Gly Asp Lys Val Tyr Ile
        580                 585                 590 gac aag atc gag ttc atc ccc gtg aac tag atc tga gctc               1816
Asp Lys Ile Glu Phe Ile Pro Val Asn         Ile
    595                 600

<210> SEQ ID NO 15
<211> LENGTH: 601
<212> TYPE: PRT
<213> ORGANISM: Artificial Sequence
<220> FEATURE:
<221> NAME/KEY: misc_feature
<222> LOCATION: (541)..(544)
<223> OTHER INFORMATION: Cathepsin G recognition sequence

<400> SEQUENCE: 15

Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Val Ser Ser Arg Asn
            100                 105                 110

Pro His Ser Gln Gly Arg Ile Arg Glu Leu Phe Ser Gln Ala Glu Ser
        115                 120                 125

His Phe Arg Asn Ser Met Pro Ser Phe Ala Ile Ser Gly Tyr Glu Val
    130                 135                 140

Leu Phe Leu Thr Thr Tyr Ala Gln Ala Ala Asn Thr His Leu Phe Leu
145                 150                 155                 160

Leu Lys Asp Ala Gln Ile Tyr Gly Glu Glu Trp Gly Tyr Glu Lys Glu
                165                 170                 175

Asp Ile Ala Glu Phe Tyr Lys Arg Gln Leu Lys Leu Thr Gln Glu Tyr
            180                 185                 190

Thr Asp His Cys Val Lys Trp Tyr Asn Val Gly Leu Asp Lys Leu Arg
        195                 200                 205

Gly Ser Ser Tyr Glu Ser Trp Val Asn Phe Asn Arg Tyr Arg Arg Glu
    210                 215                 220

Met Thr Leu Thr Val Leu Asp Leu Ile Ala Leu Phe Pro Leu Tyr Asp
225                 230                 235                 240

Val Arg Leu Tyr Pro Lys Glu Val Lys Thr Glu Leu Thr Arg Asp Val
                245                 250                 255

Leu Thr Asp Pro Ile Val Gly Val Asn Asn Leu Arg Gly Tyr Gly Thr
            260                 265                 270
```

```
Thr Phe Ser Asn Ile Glu Asn Tyr Ile Arg Lys Pro His Leu Phe Asp
        275                 280                 285

Tyr Leu His Arg Ile Gln Phe His Thr Arg Phe Gln Pro Gly Tyr Tyr
    290                 295                 300

Gly Asn Asp Ser Phe Asn Tyr Trp Ser Gly Asn Tyr Val Ser Thr Arg
305                 310                 315                 320

Pro Ser Ile Gly Ser Asn Asp Ile Ile Thr Ser Pro Phe Tyr Gly Asn
                325                 330                 335

Lys Ser Ser Glu Pro Val Gln Asn Leu Glu Phe Asn Gly Glu Lys Val
                340                 345                 350

Tyr Arg Ala Val Ala Asn Thr Asn Leu Ala Val Trp Pro Ser Ala Val
            355                 360                 365

Tyr Ser Gly Val Thr Lys Val Glu Phe Ser Gln Tyr Asn Asp Gln Thr
        370                 375                 380

Asp Glu Ala Ser Thr Gln Thr Tyr Asp Ser Lys Arg Asn Val Gly Ala
385                 390                 395                 400

Val Ser Trp Asp Ser Ile Asp Gln Leu Pro Pro Glu Thr Thr Asp Glu
                405                 410                 415

Pro Leu Glu Lys Gly Tyr Ser His Gln Leu Asn Tyr Val Met Cys Phe
                420                 425                 430

Leu Met Gln Gly Ser Arg Gly Thr Ile Pro Val Leu Thr Trp Thr His
            435                 440                 445

Lys Ser Val Asp Phe Phe Asn Met Ile Asp Ser Lys Lys Ile Thr Gln
        450                 455                 460

Leu Pro Leu Val Lys Ala Tyr Lys Leu Gln Ser Gly Ala Ser Val Val
465                 470                 475                 480

Ala Gly Pro Arg Phe Thr Gly Gly Asp Ile Ile Gln Cys Thr Glu Asn
                485                 490                 495

Gly Ser Ala Ala Thr Ile Tyr Val Thr Pro Asp Val Ser Tyr Ser Gln
                500                 505                 510

Lys Tyr Arg Ala Arg Ile His Tyr Ala Ser Thr Ser Gln Ile Thr Phe
            515                 520                 525

Thr Leu Ser Leu Asp Gly Ala Pro Phe Asn Gln Tyr Ala Ala Pro Phe
        530                 535                 540

Tyr Phe Asp Lys Thr Ile Asn Lys Gly Asp Thr Leu Thr Tyr Asn Ser
545                 550                 555                 560

Phe Asn Leu Ala Ser Phe Ser Thr Pro Phe Glu Leu Ser Gly Asn Asn
                565                 570                 575

Leu Gln Ile Gly Val Thr Gly Leu Ser Ala Gly Asp Lys Val Tyr Ile
                580                 585                 590

Asp Lys Ile Glu Phe Ile Pro Val Asn
            595                 600

<210> SEQ ID NO 16
<211> LENGTH: 1813
<212> TYPE: DNA
<213> ORGANISM: Artificial Sequence
<220> FEATURE:
<221> NAME/KEY: CDS
<222> LOCATION: (1)..(1812)
<223> OTHER INFORMATION: Maize optimized  modified cry3A057 coding
      sequence.
<220> FEATURE:
<221> NAME/KEY: misc_feature
<222> LOCATION: (322)..(333)
<223> OTHER INFORMATION: Cathepsin G recognition site coding sequence
<220> FEATURE:
<221> NAME/KEY: misc_feature
```

-continued

<222> LOCATION: (1618)..(1629)
<223> OTHER INFORMATION: Cathepsin G recognition site coding sequence

<400> SEQUENCE: 16

| | | |
|---|---|---|
| atg acg gcc gac aac aac acc gag gcc ctg gac agc agc acc acc aag<br>Met Thr Ala Asp Asn Asn Thr Glu Ala Leu Asp Ser Ser Thr Thr Lys<br>1                 5                    10                 15 | 48 |
| gac gtg atc cag aag ggc atc agc gtg gtg ggc gac ctg ctg ggc gtg<br>Asp Val Ile Gln Lys Gly Ile Ser Val Val Gly Asp Leu Leu Gly Val<br>                 20                   25                    30 | 96 |
| gtg ggc ttc ccc ttc ggc ggc gcc ctg gtg agc ttc tac acc aac ttc<br>Val Gly Phe Pro Phe Gly Gly Ala Leu Val Ser Phe Tyr Thr Asn Phe<br>          35                   40                    45 | 144 |
| ctg aac acc atc tgg ccc agc gag gac ccc tgg aag gcc ttc atg gag<br>Leu Asn Thr Ile Trp Pro Ser Glu Asp Pro Trp Lys Ala Phe Met Glu<br>50                     55                    60 | 192 |
| cag gtg gag gcc ctg atg gac cag aag atc gcc gac tac gcc aag aac<br>Gln Val Glu Ala Leu Met Asp Gln Lys Ile Ala Asp Tyr Ala Lys Asn<br>65                   70                   75                  80 | 240 |
| aag gca ctg gcc gag cta cag ggc ctc cag aac aac gtg gag gac tat<br>Lys Ala Leu Ala Glu Leu Gln Gly Leu Gln Asn Asn Val Glu Asp Tyr<br>                      85                    90                  95 | 288 |
| gtg agc gcc ctg agc agc tgg cag aag aac ccc gct gca ccg ttc ccc<br>Val Ser Ala Leu Ser Ser Trp Gln Lys Asn Pro Ala Ala Pro Phe Pro<br>               100                    105                 110 | 336 |
| cac agc cag ggc cgc atc cgc gag ctg ttc agc cag gcc gag agc cac<br>His Ser Gln Gly Arg Ile Arg Glu Leu Phe Ser Gln Ala Glu Ser His<br>               115                    120                 125 | 384 |
| ttc cgc aac agc atg ccc agc ttc gcc atc agc ggc tac gag gtg ctg<br>Phe Arg Asn Ser Met Pro Ser Phe Ala Ile Ser Gly Tyr Glu Val Leu<br>130                   135                  140 | 432 |
| ttc ctg acc acc tac gcc cag gcc gcc aac acc cac ctg ttc ctg ctg<br>Phe Leu Thr Thr Tyr Ala Gln Ala Ala Asn Thr His Leu Phe Leu Leu<br>145                   150                  155                 160 | 480 |
| aag gac gcc caa atc tac gga gag gag tgg ggc tac gag aag gag gac<br>Lys Asp Ala Gln Ile Tyr Gly Glu Glu Trp Gly Tyr Glu Lys Glu Asp<br>                   165                   170                 175 | 528 |
| atc gcc gag ttc tac aag cgc cag ctg aag ctg acc cag gag tac acc<br>Ile Ala Glu Phe Tyr Lys Arg Gln Leu Lys Leu Thr Gln Glu Tyr Thr<br>               180                    185                 190 | 576 |
| gac cac tgc gtg aag tgg tac aac gtg ggt cta gac aag ctc cgc ggc<br>Asp His Cys Val Lys Trp Tyr Asn Val Gly Leu Asp Lys Leu Arg Gly<br>               195                    200                 205 | 624 |
| agc agc tac gag agc tgg gtg aac ttc aac cgc tac cgc cgc gag atg<br>Ser Ser Tyr Glu Ser Trp Val Asn Phe Asn Arg Tyr Arg Arg Glu Met<br>210                   215                  220 | 672 |
| acc ctg acc gtg ctg gac ctg atc gcc ctg ttc ccc ctg tac gac gtg<br>Thr Leu Thr Val Leu Asp Leu Ile Ala Leu Phe Pro Leu Tyr Asp Val<br>225                   230                  235                 240 | 720 |
| cgc ctg tac ccc aag gag gtg aag acc gag ctg acc cgc gac gtg ctg<br>Arg Leu Tyr Pro Lys Glu Val Lys Thr Glu Leu Thr Arg Asp Val Leu<br>                   245                   250                 255 | 768 |
| acc gac ccc atc gtg ggc gtg aac aac ctg cgc ggc tac ggc acc acc<br>Thr Asp Pro Ile Val Gly Val Asn Asn Leu Arg Gly Tyr Gly Thr Thr<br>               260                    265                 270 | 816 |
| ttc agc aac atc gag aac tac atc cgc aag ccc cac ctg ttc gac tac<br>Phe Ser Asn Ile Glu Asn Tyr Ile Arg Lys Pro His Leu Phe Asp Tyr<br>               275                   280                 285 | 864 |
| ctg cac cgc atc cag ttc cac acg cgt ttc cag ccc ggc tac tac ggc<br>Leu His Arg Ile Gln Phe His Thr Arg Phe Gln Pro Gly Tyr Tyr Gly | 912 |

```
                290                 295                 300
aac gac agc ttc aac tac tgg agc ggc aac tac gtg agc acc cgc ccc      960
Asn Asp Ser Phe Asn Tyr Trp Ser Gly Asn Tyr Val Ser Thr Arg Pro
305                 310                 315                 320 agc atc ggc agc aac gac atc atc acc agc ccc ttc tac ggc aac aag     1008
Ser Ile Gly Ser Asn Asp Ile Ile Thr Ser Pro Phe Tyr Gly Asn Lys
                325                 330                 335 agc agc gag ccc gtg cag aac ctt gag ttc aac ggc gag aag gtg tac     1056
Ser Ser Glu Pro Val Gln Asn Leu Glu Phe Asn Gly Glu Lys Val Tyr
            340                 345                 350 cgc gcc gtg gct aac acc aac ctg gcc gtg tgg ccc tct gca gtg tac     1104
Arg Ala Val Ala Asn Thr Asn Leu Ala Val Trp Pro Ser Ala Val Tyr
        355                 360                 365 agc ggc gtg acc aag gtg gag ttc agc cag tac aac gac cag acc gac     1152
Ser Gly Val Thr Lys Val Glu Phe Ser Gln Tyr Asn Asp Gln Thr Asp
    370                 375                 380 gag gcc agc acc cag acc tac gac agc aag cgc aac gtg ggc gcc gtg     1200
Glu Ala Ser Thr Gln Thr Tyr Asp Ser Lys Arg Asn Val Gly Ala Val
385                 390                 395                 400 agc tgg gac agc atc gac cag ctg ccc ccc gag acc acc gac gag ccc     1248
Ser Trp Asp Ser Ile Asp Gln Leu Pro Pro Glu Thr Thr Asp Glu Pro
                405                 410                 415 ctg gag aag ggc tac agc cac cag ctg aac tac gtg atg tgc ttc ctg     1296
Leu Glu Lys Gly Tyr Ser His Gln Leu Asn Tyr Val Met Cys Phe Leu
            420                 425                 430 atg cag ggc agc cgc ggc acc atc ccc gtg ctg acc tgg acc cac aag     1344
Met Gln Gly Ser Arg Gly Thr Ile Pro Val Leu Thr Trp Thr His Lys
        435                 440                 445 agc gtc gac ttc ttc aac atg atc gac agc aag aag atc acc cag ctg     1392
Ser Val Asp Phe Phe Asn Met Ile Asp Ser Lys Lys Ile Thr Gln Leu
    450                 455                 460 ccc ctg gtg aag gcc tac aag ctc cag agc ggc gcc agc gtg gtg gca     1440
Pro Leu Val Lys Ala Tyr Lys Leu Gln Ser Gly Ala Ser Val Val Ala
465                 470                 475                 480 ggc ccc cgc ttc acc ggc ggc gac atc atc cag tgc acc gag aac ggc     1488
Gly Pro Arg Phe Thr Gly Gly Asp Ile Ile Gln Cys Thr Glu Asn Gly
                485                 490                 495 agc gcc gcc acc atc tac gtg acc ccc gac gtg agc tac agc cag aag     1536
Ser Ala Ala Thr Ile Tyr Val Thr Pro Asp Val Ser Tyr Ser Gln Lys
            500                 505                 510 tac cgc gcc cgc atc cac tac gcc agc acc agc cag atc acc ttc acc     1584
Tyr Arg Ala Arg Ile His Tyr Ala Ser Thr Ser Gln Ile Thr Phe Thr
        515                 520                 525 ctg agc ctg gac ggg gcc ccc ttc aac caa tac gct gca ccg ttc tac     1632
Leu Ser Leu Asp Gly Ala Pro Phe Asn Gln Tyr Ala Ala Pro Phe Tyr
    530                 535                 540 ttc gac aag acc atc aac aag ggc gac acc ctg acc tac aac agc ttc     1680
Phe Asp Lys Thr Ile Asn Lys Gly Asp Thr Leu Thr Tyr Asn Ser Phe
545                 550                 555                 560 aac ctg gcc agc ttc agc acc cct ttc gag ctg agc ggc aac aac ctc     1728
Asn Leu Ala Ser Phe Ser Thr Pro Phe Glu Leu Ser Gly Asn Asn Leu
                565                 570                 575 cag atc ggc gtg acc ggc ctg agc gcc ggc gac aag gtg tac atc gac     1776
Gln Ile Gly Val Thr Gly Leu Ser Ala Gly Asp Lys Val Tyr Ile Asp
            580                 585                 590 aag atc gag ttc atc ccc gtg aac tag atc tga gct c                   1813
Lys Ile Glu Phe Ile Pro Val Asn     Ile     Ala
        595                 600
```

-continued

```
<210> SEQ ID NO 17
<211> LENGTH: 600
<212> TYPE: PRT
<213> ORGANISM: Artificial Sequence
<220> FEATURE:
<221> NAME/KEY: misc_feature
<222> LOCATION: (108)..(111)
<223> OTHER INFORMATION: Cathepsin G recognition sequence
<220> FEATURE:
<221> NAME/KEY: misc_feature
<222> LOCATION: (540)..(543)
<223> OTHER INFORMATION: Cathepsin G recognition sequence

<400> SEQUENCE: 17
```

Met Thr Ala Asp Asn Asn Thr Glu Ala Leu Asp Ser Thr Thr Lys
1               5                   10                  15

Asp Val Ile Gln Lys Gly Ile Ser Val Val Gly Asp Leu Leu Gly
                20                  25                  30

Val Gly Phe Pro Phe Gly Gly Ala Leu Val Ser Phe Tyr Thr Asn Phe
            35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Ala Ala Pro Phe Pro
            100                 105                 110

His Ser Gln Gly Arg Ile Arg Glu Leu Phe Ser Gln Ala Glu Ser His
        115                 120                 125

Phe Arg Asn Ser Met Pro Ser Phe Ala Ile Ser Gly Tyr Glu Val Leu
    130                 135                 140

Phe Leu Thr Thr Tyr Ala Gln Ala Ala Asn Thr His Leu Phe Leu Leu
145                 150                 155                 160

Lys Asp Ala Gln Ile Tyr Gly Glu Glu Trp Gly Tyr Glu Lys Glu Asp
                165                 170                 175

Ile Ala Glu Phe Tyr Lys Arg Gln Leu Lys Leu Thr Gln Glu Tyr Thr
            180                 185                 190

Asp His Cys Val Lys Trp Tyr Asn Val Gly Leu Asp Lys Leu Arg Gly
        195                 200                 205

Ser Ser Tyr Glu Ser Trp Val Asn Phe Asn Arg Tyr Arg Arg Glu Met
    210                 215                 220

Thr Leu Thr Val Leu Asp Leu Ile Ala Leu Phe Pro Leu Tyr Asp Val
225                 230                 235                 240

Arg Leu Tyr Pro Lys Glu Val Lys Thr Glu Leu Thr Arg Asp Val Leu
                245                 250                 255

Thr Asp Pro Ile Val Gly Val Asn Asn Leu Arg Gly Tyr Gly Thr Thr
            260                 265                 270

Phe Ser Asn Ile Glu Asn Tyr Ile Arg Lys Pro His Leu Phe Asp Tyr
        275                 280                 285

Leu His Arg Ile Gln Phe His Thr Arg Phe Gln Pro Gly Tyr Tyr Gly
    290                 295                 300

Asn Asp Ser Phe Asn Tyr Trp Ser Gly Asn Tyr Val Ser Thr Arg Pro
305                 310                 315                 320

Ser Ile Gly Ser Asn Asp Ile Ile Thr Ser Pro Phe Tyr Gly Asn Lys
                325                 330                 335

Ser Ser Glu Pro Val Gln Asn Leu Glu Phe Asn Gly Glu Lys Val Tyr

```
                340             345             350
Arg Ala Val Ala Asn Thr Asn Leu Ala Val Trp Pro Ser Ala Val Tyr
            355             360             365

Ser Gly Val Thr Lys Val Glu Phe Ser Gln Tyr Asn Asp Gln Thr Asp
    370             375             380

Glu Ala Ser Thr Gln Thr Tyr Asp Ser Lys Arg Asn Val Gly Ala Val
385             390             395             400

Ser Trp Asp Ser Ile Asp Gln Leu Pro Pro Glu Thr Thr Asp Glu Pro
                405             410             415

Leu Glu Lys Gly Tyr Ser His Gln Leu Asn Tyr Val Met Cys Phe Leu
            420             425             430

Met Gln Gly Ser Arg Gly Thr Ile Pro Val Leu Thr Trp Thr His Lys
        435             440             445

Ser Val Asp Phe Phe Asn Met Ile Asp Ser Lys Lys Ile Thr Gln Leu
    450             455             460

Pro Leu Val Lys Ala Tyr Lys Leu Gln Ser Gly Ala Ser Val Val Ala
465             470             475             480

Gly Pro Arg Phe Thr Gly Gly Asp Ile Ile Gln Cys Thr Glu Asn Gly
                485             490             495

Ser Ala Ala Thr Ile Tyr Val Thr Pro Asp Val Ser Tyr Ser Gln Lys
            500             505             510

Tyr Arg Ala Arg Ile His Tyr Ala Ser Thr Ser Gln Ile Thr Phe Thr
        515             520             525

Leu Ser Leu Asp Gly Ala Pro Phe Asn Gln Tyr Ala Ala Pro Phe Tyr
    530             535             540

Phe Asp Lys Thr Ile Asn Lys Gly Asp Thr Leu Thr Tyr Asn Ser Phe
545             550             555             560

Asn Leu Ala Ser Phe Ser Thr Pro Phe Glu Leu Ser Gly Asn Asn Leu
                565             570             575

Gln Ile Gly Val Thr Gly Leu Ser Ala Gly Asp Lys Val Tyr Ile Asp
            580             585             590

Lys Ile Glu Phe Ile Pro Val Asn
        595             600

<210> SEQ ID NO 18
<211> LENGTH: 1819
<212> TYPE: DNA
<213> ORGANISM: Artificial Sequence
<220> FEATURE:
<221> NAME/KEY: CDS
<222> LOCATION: (1)..(1818)
<223> OTHER INFORMATION: Maize optimized  modified cry3A056 coding
      sequence.
<220> FEATURE:
<221> NAME/KEY: misc_feature
<222> LOCATION: (322)..(333)
<223> OTHER INFORMATION: Catthepsin G recognition site coding sequence.
<220> FEATURE:
<221> NAME/KEY: misc_feature
<222> LOCATION: (1624)..(1635)
<223> OTHER INFORMATION: Catthepsin G recognition site coding sequence.

<400> SEQUENCE: 18 atg acg gcc gac aac aac acc gag gcc ctg gac agc agc acc acc aag     48
Met Thr Ala Asp Asn Asn Thr Glu Ala Leu Asp Ser Ser Thr Thr Lys
1               5                   10                  15 gac gtg atc cag aag ggc atc agc gtg gtg ggc gac ctg ctg ggc gtg     96
Asp Val Ile Gln Lys Gly Ile Ser Val Val Gly Asp Leu Leu Gly Val
            20                  25                  30
```

```
gtg ggc ttc ccc ttc ggc ggc gcc ctg gtg agc ttc tac acc aac ttc     144
Val Gly Phe Pro Phe Gly Gly Ala Leu Val Ser Phe Tyr Thr Asn Phe
             35                  40                  45 ctg aac acc atc tgg ccc agc gag gac ccc tgg aag gcc ttc atg gag     192
Leu Asn Thr Ile Trp Pro Ser Glu Asp Pro Trp Lys Ala Phe Met Glu
 50                  55                  60 cag gtg gag gcc ctg atg gac cag aag atc gcc gac tac gcc aag aac     240
Gln Val Glu Ala Leu Met Asp Gln Lys Ile Ala Asp Tyr Ala Lys Asn
 65                  70                  75                  80 aag gca ctg gcc gag cta cag ggc ctc cag aac aac gtg gag gac tat     288
Lys Ala Leu Ala Glu Leu Gln Gly Leu Gln Asn Asn Val Glu Asp Tyr
                 85                  90                  95 gtg agc gcc ctg agc agc tgg cag aag aac ccc gct gca ccg ttc cgc     336
Val Ser Ala Leu Ser Ser Trp Gln Lys Asn Pro Ala Ala Pro Phe Arg
            100                 105                 110 aac ccc cac agc cag ggc cgc atc cgc gag ctg ttc agc cag gcc gag     384
Asn Pro His Ser Gln Gly Arg Ile Arg Glu Leu Phe Ser Gln Ala Glu
            115                 120                 125 agc cac ttc cgc aac agc atg ccc agc ttc gcc atc agc ggc tac gag     432
Ser His Phe Arg Asn Ser Met Pro Ser Phe Ala Ile Ser Gly Tyr Glu
        130                 135                 140 gtg ctg ttc ctg acc acc tac gcc cag gcc gcc aac acc cac ctg ttc     480
Val Leu Phe Leu Thr Thr Tyr Ala Gln Ala Ala Asn Thr His Leu Phe
145                 150                 155                 160 ctg ctg aag gac gcc caa atc tac gga gag gag tgg ggc tac gag aag     528
Leu Leu Lys Asp Ala Gln Ile Tyr Gly Glu Glu Trp Gly Tyr Glu Lys
                165                 170                 175 gag gac atc gcc gag ttc tac aag cgc cag ctg aag ctg acc cag gag     576
Glu Asp Ile Ala Glu Phe Tyr Lys Arg Gln Leu Lys Leu Thr Gln Glu
            180                 185                 190 tac acc gac cac tgc gtg aag tgg tac aac gtg ggt cta gac aag ctc     624
Tyr Thr Asp His Cys Val Lys Trp Tyr Asn Val Gly Leu Asp Lys Leu
            195                 200                 205 cgc ggc agc agc tac gag agc tgg gtg aac ttc aac cgc tac cgc cgc     672
Arg Gly Ser Ser Tyr Glu Ser Trp Val Asn Phe Asn Arg Tyr Arg Arg
        210                 215                 220 gag atg acc ctg acc gtg ctg gac ctg atc gcc ctg ttc ccc ctg tac     720
Glu Met Thr Leu Thr Val Leu Asp Leu Ile Ala Leu Phe Pro Leu Tyr
225                 230                 235                 240 gac gtg cgc ctg tac ccc aag gag gtg aag acc gag ctg acc cgc gac     768
Asp Val Arg Leu Tyr Pro Lys Glu Val Lys Thr Glu Leu Thr Arg Asp
                245                 250                 255 gtg ctg acc gac ccc atc gtg ggc gtg aac aac ctg cgc ggc tac ggc     816
Val Leu Thr Asp Pro Ile Val Gly Val Asn Asn Leu Arg Gly Tyr Gly
            260                 265                 270 acc acc ttc agc aac atc gag aac tac atc cgc aag ccc cac ctg ttc     864
Thr Thr Phe Ser Asn Ile Glu Asn Tyr Ile Arg Lys Pro His Leu Phe
        275                 280                 285 gac tac ctg cac cgc atc cag ttc cac acg cgt ttc cag ccc ggc tac     912
Asp Tyr Leu His Arg Ile Gln Phe His Thr Arg Phe Gln Pro Gly Tyr
    290                 295                 300 tac ggc aac gac agc ttc aac tac tgg agc ggc aac tac gtg agc acc     960
Tyr Gly Asn Asp Ser Phe Asn Tyr Trp Ser Gly Asn Tyr Val Ser Thr
305                 310                 315                 320 cgc ccc agc atc ggc agc aac gac atc atc acc agc ccc ttc tac ggc    1008
Arg Pro Ser Ile Gly Ser Asn Asp Ile Ile Thr Ser Pro Phe Tyr Gly
                325                 330                 335 aac aag agc agc gag ccc gtg cag aac ctt gag ttc aac ggc gag aag    1056
Asn Lys Ser Ser Glu Pro Val Gln Asn Leu Glu Phe Asn Gly Glu Lys
            340                 345                 350
```

```
gtg tac cgc gcc gtg gct aac acc aac ctg gcc gtg tgg ccc tct gca      1104
Val Tyr Arg Ala Val Ala Asn Thr Asn Leu Ala Val Trp Pro Ser Ala
        355                 360                 365 gtg tac agc ggc gtg acc aag gtg gag ttc agc cag tac aac gac cag      1152
Val Tyr Ser Gly Val Thr Lys Val Glu Phe Ser Gln Tyr Asn Asp Gln
370                 375                 380 acc gac gag gcc agc acc cag acc tac gac agc aag cgc aac gtg ggc      1200
Thr Asp Glu Ala Ser Thr Gln Thr Tyr Asp Ser Lys Arg Asn Val Gly
385                 390                 395                 400 gcc gtg agc tgg gac agc atc gac cag ctg ccc ccc gag acc acc gac      1248
Ala Val Ser Trp Asp Ser Ile Asp Gln Leu Pro Pro Glu Thr Thr Asp
                405                 410                 415 gag ccc ctg gag aag ggc tac agc cac cag ctg aac tac gtg atg tgc      1296
Glu Pro Leu Glu Lys Gly Tyr Ser His Gln Leu Asn Tyr Val Met Cys
            420                 425                 430 ttc ctg atg cag ggc agc cgc ggc acc atc ccc gtg ctg acc tgg acc      1344
Phe Leu Met Gln Gly Ser Arg Gly Thr Ile Pro Val Leu Thr Trp Thr
        435                 440                 445 cac aag agc gtc gac ttc ttc aac atg atc gac agc aag aag atc acc      1392
His Lys Ser Val Asp Phe Phe Asn Met Ile Asp Ser Lys Lys Ile Thr
450                 455                 460 cag ctg ccc ctg gtg aag gcc tac aag ctc cag agc ggc gcc agc gtg      1440
Gln Leu Pro Leu Val Lys Ala Tyr Lys Leu Gln Ser Gly Ala Ser Val
465                 470                 475                 480 gtg gca ggc ccc cgc ttc acc ggc ggc gac atc atc cag tgc acc gag      1488
Val Ala Gly Pro Arg Phe Thr Gly Gly Asp Ile Ile Gln Cys Thr Glu
                485                 490                 495 aac ggc agc gcc gcc acc atc tac gtg acc ccc gac gtg agc tac agc      1536
Asn Gly Ser Ala Ala Thr Ile Tyr Val Thr Pro Asp Val Ser Tyr Ser
            500                 505                 510 cag aag tac cgc gcc cgc atc cac tac gcc agc acc agc cag atc acc      1584
Gln Lys Tyr Arg Ala Arg Ile His Tyr Ala Ser Thr Ser Gln Ile Thr
        515                 520                 525 ttc acc ctg agc ctg gac ggg gcc ccc ttc aac caa tac gct gca ccg      1632
Phe Thr Leu Ser Leu Asp Gly Ala Pro Phe Asn Gln Tyr Ala Ala Pro
530                 535                 540 ttc tac ttc gac aag acc atc aac aag ggc gac acc ctg acc tac aac      1680
Phe Tyr Phe Asp Lys Thr Ile Asn Lys Gly Asp Thr Leu Thr Tyr Asn
545                 550                 555                 560 agc ttc aac ctg gcc agc ttc agc acc cct ttc gag ctg agc ggc aac      1728
Ser Phe Asn Leu Ala Ser Phe Ser Thr Pro Phe Glu Leu Ser Gly Asn
                565                 570                 575 aac ctc cag atc ggc gtg acc ggc ctg agc gcc ggc gac aag gtg tac      1776
Asn Leu Gln Ile Gly Val Thr Gly Leu Ser Ala Gly Asp Lys Val Tyr
            580                 585                 590 atc gac aag atc gag ttc atc ccc gtg aac tag atc tga gct c            1819
Ile Asp Lys Ile Glu Phe Ile Pro Val Asn     Ile     Ala
        595                 600

<210> SEQ ID NO 19
<211> LENGTH: 602
<212> TYPE: PRT
<213> ORGANISM: Artificial Sequence
<220> FEATURE:
<221> NAME/KEY: misc_feature
<222> LOCATION: (108)..(111)
<223> OTHER INFORMATION: Catthepsin G recognition sequence.
<220> FEATURE:
<221> NAME/KEY: misc_feature
<222> LOCATION: (542)..(545)
<223> OTHER INFORMATION: Catthepsin G recognition sequence.
```

-continued

<400> SEQUENCE: 19

```
Met Thr Ala Asp Asn Asn Thr Glu Ala Leu Asp Ser Ser Thr Thr Lys
1               5                   10                  15
Asp Val Ile Gln Lys Gly Ile Ser Val Val Gly Asp Leu Leu Gly Val
            20                  25                  30
Val Gly Phe Pro Phe Gly Gly Ala Leu Val Ser Phe Tyr Thr Asn Phe
        35                  40                  45
Leu Asn Thr Ile Trp Pro Ser Glu Asp Pro Trp Lys Ala Phe Met Glu
    50                  55                  60
Gln Val Glu Ala Leu Met Asp Gln Lys Ile Ala Asp Tyr Ala Lys Asn
65                  70                  75                  80
Lys Ala Leu Ala Glu Leu Gln Gly Leu Gln Asn Asn Val Glu Asp Tyr
                85                  90                  95
Val Ser Ala Leu Ser Ser Trp Gln Lys Asn Pro Ala Ala Pro Phe Arg
            100                 105                 110
Asn Pro His Ser Gln Gly Arg Ile Arg Glu Leu Phe Ser Gln Ala Glu
        115                 120                 125
Ser His Phe Arg Asn Ser Met Pro Ser Phe Ala Ile Ser Gly Tyr Glu
    130                 135                 140
Val Leu Phe Leu Thr Thr Tyr Ala Gln Ala Ala Asn Thr His Leu Phe
145                 150                 155                 160
Leu Leu Lys Asp Ala Gln Ile Tyr Gly Glu Glu Trp Gly Tyr Glu Lys
                165                 170                 175
Glu Asp Ile Ala Glu Phe Tyr Lys Arg Gln Leu Lys Leu Thr Gln Glu
            180                 185                 190
Tyr Thr Asp His Cys Val Lys Trp Tyr Asn Val Gly Leu Asp Lys Leu
        195                 200                 205
Arg Gly Ser Ser Tyr Glu Ser Trp Val Asn Phe Asn Arg Tyr Arg Arg
    210                 215                 220
Glu Met Thr Leu Thr Val Leu Asp Leu Ile Ala Leu Phe Pro Leu Tyr
225                 230                 235                 240
Asp Val Arg Leu Tyr Pro Lys Glu Val Lys Thr Glu Leu Thr Arg Asp
                245                 250                 255
Val Leu Thr Asp Pro Ile Val Gly Val Asn Asn Leu Arg Gly Tyr Gly
            260                 265                 270
Thr Thr Phe Ser Asn Ile Glu Asn Tyr Ile Arg Lys Pro His Leu Phe
        275                 280                 285
Asp Tyr Leu His Arg Ile Gln Phe His Thr Arg Phe Gln Pro Gly Tyr
    290                 295                 300
Tyr Gly Asn Asp Ser Phe Asn Tyr Trp Ser Gly Asn Tyr Val Ser Thr
305                 310                 315                 320
Arg Pro Ser Ile Gly Ser Asn Asp Ile Ile Thr Ser Pro Phe Tyr Gly
                325                 330                 335
Asn Lys Ser Ser Glu Pro Val Gln Asn Leu Glu Phe Asn Gly Glu Lys
            340                 345                 350
Val Tyr Arg Ala Val Ala Asn Thr Asn Leu Ala Val Trp Pro Ser Ala
        355                 360                 365
Val Tyr Ser Gly Val Thr Lys Val Glu Phe Ser Gln Tyr Asn Asp Gln
    370                 375                 380
Thr Asp Glu Ala Ser Thr Gln Thr Tyr Asp Ser Lys Arg Asn Val Gly
385                 390                 395                 400
Ala Val Ser Trp Asp Ser Ile Asp Gln Leu Pro Pro Glu Thr Thr Asp
                405                 410                 415
```

```
Glu Pro Leu Glu Lys Gly Tyr Ser His Gln Leu Asn Tyr Val Met Cys
            420                 425                 430

Phe Leu Met Gln Gly Ser Arg Gly Thr Ile Pro Val Leu Thr Trp Thr
            435                 440                 445

His Lys Ser Val Asp Phe Phe Asn Met Ile Asp Ser Lys Lys Ile Thr
            450                 455                 460

Gln Leu Pro Leu Val Lys Ala Tyr Lys Leu Gln Ser Gly Ala Ser Val
465                 470                 475                 480

Val Ala Gly Pro Arg Phe Thr Gly Gly Asp Ile Ile Gln Cys Thr Glu
                485                 490                 495

Asn Gly Ser Ala Ala Thr Ile Tyr Val Thr Pro Asp Val Ser Tyr Ser
            500                 505                 510

Gln Lys Tyr Arg Ala Arg Ile His Tyr Ala Ser Thr Ser Gln Ile Thr
            515                 520                 525

Phe Thr Leu Ser Leu Asp Gly Ala Pro Phe Asn Gln Tyr Ala Ala Pro
            530                 535                 540

Phe Tyr Phe Asp Lys Thr Ile Asn Lys Gly Asp Thr Leu Thr Tyr Asn
545                 550                 555                 560

Ser Phe Asn Leu Ala Ser Phe Ser Thr Pro Phe Glu Leu Ser Gly Asn
                565                 570                 575

Asn Leu Gln Ile Gly Val Thr Gly Leu Ser Ala Gly Asp Lys Val Tyr
            580                 585                 590

Ile Asp Lys Ile Glu Phe Ile Pro Val Asn
            595                 600

<210> SEQ ID NO 20
<211> LENGTH: 1797
<212> TYPE: DNA
<213> ORGANISM: Artificial Sequence
<220> FEATURE:
<221> NAME/KEY: CDS
<222> LOCATION: (1)..(1791)
<223> OTHER INFORMATION: Maize optimized modified cry3A083 coding
      sequence.
<220> FEATURE:
<221> NAME/KEY: misc_feature
<222> LOCATION: (322)..(333)
<223> OTHER INFORMATION: Cathepsin G recognition site coding sequence.
<220> FEATURE:
<221> NAME/KEY: misc_feature
<222> LOCATION: (1612)..(1623)
<223> OTHER INFORMATION: cathepsin G recognition site coding sequence

<400> SEQUENCE: 20 atg acg gcc gac aac aac acc gag gcc ctg gac agc agc acc acc aag    48
Met Thr Ala Asp Asn Asn Thr Glu Ala Leu Asp Ser Ser Thr Thr Lys
1               5                   10                  15 gac gtg atc cag aag ggc atc agc gtg gtg ggc gac ctg ctg ggc gtg    96
Asp Val Ile Gln Lys Gly Ile Ser Val Val Gly Asp Leu Leu Gly Val
            20                  25                  30 gtg ggc ttc ccc ttc ggc ggc gcc ctg gtg agc ttc tac acc aac ttc   144
Val Gly Phe Pro Phe Gly Gly Ala Leu Val Ser Phe Tyr Thr Asn Phe
        35                  40                  45 ctg aac acc atc tgg ccc agc gag gac ccc tgg aag gcc ttc atg gag   192
Leu Asn Thr Ile Trp Pro Ser Glu Asp Pro Trp Lys Ala Phe Met Glu
    50                  55                  60 cag gtg gag gcc ctg atg gac cag aag atc gcc gac tac gcc aag aac   240
Gln Val Glu Ala Leu Met Asp Gln Lys Ile Ala Asp Tyr Ala Lys Asn
65                  70                  75                  80 aag gca ctg gcc gag cta cag ggc ctc cag aac aac gtg gag gac tat   288
```

```
                Lys Ala Leu Ala Glu Leu Gln Gly Leu Gln Asn Asn Val Glu Asp Tyr
                             85                  90                  95 gtg agc gcc ctg agc agc tgg cag aag aac ccc gct gca ccg ttc cgc          336
Val Ser Ala Leu Ser Ser Trp Gln Lys Asn Pro Ala Ala Pro Phe Arg
            100                 105                 110 aac ccc cac agc cag ggc cgc atc cgc gag ctg ttc agc cag gcc gag          384
Asn Pro His Ser Gln Gly Arg Ile Arg Glu Leu Phe Ser Gln Ala Glu
            115                 120                 125 agc cac ttc cgc aac agc atg ccc agc ttc gcc atc agc ggc tac gag          432
Ser His Phe Arg Asn Ser Met Pro Ser Phe Ala Ile Ser Gly Tyr Glu
        130                 135                 140 gtg ctg ttc ctg acc acc tac gcc cag gcc gcc aac acc cac ctg ttc          480
Val Leu Phe Leu Thr Thr Tyr Ala Gln Ala Ala Asn Thr His Leu Phe
145                 150                 155                 160 ctg ctg aag gac gcc caa atc tac gga gag gag tgg ggc tac gag aag          528
Leu Leu Lys Asp Ala Gln Ile Tyr Gly Glu Glu Trp Gly Tyr Glu Lys
                165                 170                 175 gag gac atc gcc gag ttc tac aag cgc cag ctg aag ctg acc cag gag          576
Glu Asp Ile Ala Glu Phe Tyr Lys Arg Gln Leu Lys Leu Thr Gln Glu
                180                 185                 190 tac acc gac cac tgc gtg aag tgg tac aac gtg ggt cta gac aag ctc          624
Tyr Thr Asp His Cys Val Lys Trp Tyr Asn Val Gly Leu Asp Lys Leu
            195                 200                 205 cgc ggc agc agc tac gag agc tgg gtg aac ttc aac cgc tac cgc cgc          672
Arg Gly Ser Ser Tyr Glu Ser Trp Val Asn Phe Asn Arg Tyr Arg Arg
        210                 215                 220 gag atg acc ctg acc gtg ctg gac ctg atc gcc ctg ttc ccc ctg tac          720
Glu Met Thr Leu Thr Val Leu Asp Leu Ile Ala Leu Phe Pro Leu Tyr
225                 230                 235                 240 gac gtg cgc ctg tac ccc aag gag gtg aag acc gag ctg acc cgc gac          768
Asp Val Arg Leu Tyr Pro Lys Glu Val Lys Thr Glu Leu Thr Arg Asp
                245                 250                 255 gtg ctg acc gac ccc atc gtg ggc gtg aac aac ctg cgc ggc tac ggc          816
Val Leu Thr Asp Pro Ile Val Gly Val Asn Asn Leu Arg Gly Tyr Gly
                260                 265                 270 acc acc ttc agc aac atc gag aac tac atc cgc aag ccc cac ctg ttc          864
Thr Thr Phe Ser Asn Ile Glu Asn Tyr Ile Arg Lys Pro His Leu Phe
            275                 280                 285 gac tac ctg cac cgc atc cag ttc cac acg cgt ttc cag ccc ggc tac          912
Asp Tyr Leu His Arg Ile Gln Phe His Thr Arg Phe Gln Pro Gly Tyr
        290                 295                 300 tac ggc aac gac agc ttc aac tac tgg agc ggc aac tac gtg agc acc          960
Tyr Gly Asn Asp Ser Phe Asn Tyr Trp Ser Gly Asn Tyr Val Ser Thr
305                 310                 315                 320 cgc ccc agc atc ggc agc aac gac atc atc acc agc ccc ttc tac ggc         1008
Arg Pro Ser Ile Gly Ser Asn Asp Ile Ile Thr Ser Pro Phe Tyr Gly
                325                 330                 335 aac aag agc agc gag ccc gtg cag aac ctt gag ttc aac ggc gag aag         1056
Asn Lys Ser Ser Glu Pro Val Gln Asn Leu Glu Phe Asn Gly Glu Lys
                340                 345                 350 gtg tac cgc gcc gtg gct aac acc aac ctg gcc gtg tgg ccc tct gca         1104
Val Tyr Arg Ala Val Ala Asn Thr Asn Leu Ala Val Trp Pro Ser Ala
            355                 360                 365 gtg tac agc ggc gtg acc aag gtg gag ttc agc cag tac aac gac cag         1152
Val Tyr Ser Gly Val Thr Lys Val Glu Phe Ser Gln Tyr Asn Asp Gln
        370                 375                 380 acc gac gag gcc agc acc cag acc tac gac agc aag cgc aac gtg ggc         1200
Thr Asp Glu Ala Ser Thr Gln Thr Tyr Asp Ser Lys Arg Asn Val Gly
385                 390                 395                 400
```

-continued

```
gcc gtg agc tgg gac agc atc gac cag ctg ccc ccc gag acc acc gac    1248
Ala Val Ser Trp Asp Ser Ile Asp Gln Leu Pro Pro Glu Thr Thr Asp
            405                 410                 415 gag ccc ctg gag aag ggc tac agc cac cag ctg aac tac gtg atg tgc    1296
Glu Pro Leu Glu Lys Gly Tyr Ser His Gln Leu Asn Tyr Val Met Cys
        420                 425                 430 ttc ctg atg cag ggc agc cgc ggc acc atc ccc gtg ctg acc tgg acc    1344
Phe Leu Met Gln Gly Ser Arg Gly Thr Ile Pro Val Leu Thr Trp Thr
    435                 440                 445 cac aag agc gtc gac ttc ttc aac atg atc gac agc aag aag atc acc    1392
His Lys Ser Val Asp Phe Phe Asn Met Ile Asp Ser Lys Lys Ile Thr
450                 455                 460 cag ctg ccc ctg gtg aag gcc tac aag ctc cag agc ggc gcc agc gtg    1440
Gln Leu Pro Leu Val Lys Ala Tyr Lys Leu Gln Ser Gly Ala Ser Val
465                 470                 475                 480 gtg gca ggc ccc cgc ttc acc ggc ggc gac atc atc cag tgc acc gag    1488
Val Ala Gly Pro Arg Phe Thr Gly Gly Asp Ile Ile Gln Cys Thr Glu
                485                 490                 495 aac ggc agc gcc gcc acc atc tac gtg acc ccc gac gtg agc tac agc    1536
Asn Gly Ser Ala Ala Thr Ile Tyr Val Thr Pro Asp Val Ser Tyr Ser
            500                 505                 510 cag aag tac cgc gcc cgc atc cac tac gcc agc acc agc cag atc acc    1584
Gln Lys Tyr Arg Ala Arg Ile His Tyr Ala Ser Thr Ser Gln Ile Thr
        515                 520                 525 ttc acc ctg agc ctg gac ggg gcc ccc gct gca ccg ttc tac ttc gac    1632
Phe Thr Leu Ser Leu Asp Gly Ala Pro Ala Ala Pro Phe Tyr Phe Asp
    530                 535                 540 aag acc atc aac aag ggc gac acc ctg acc tac aac agc ttc aac ctg    1680
Lys Thr Ile Asn Lys Gly Asp Thr Leu Thr Tyr Asn Ser Phe Asn Leu
545                 550                 555                 560 gcc agc ttc agc acc cct ttc gag ctg agc ggc aac aac ctc cag atc    1728
Ala Ser Phe Ser Thr Pro Phe Glu Leu Ser Gly Asn Asn Leu Gln Ile
                565                 570                 575 ggc gtg acc ggc ctg agc gcc ggc gac aag gtg tac atc gac aag atc    1776
Gly Val Thr Gly Leu Ser Ala Gly Asp Lys Val Tyr Ile Asp Lys Ile
            580                 585                 590 gag ttc atc ccc gtg aactag                                         1797
Glu Phe Ile Pro Val
        595
```

```
<210> SEQ ID NO 21
<211> LENGTH: 597
<212> TYPE: PRT
<213> ORGANISM: Artificial Sequence
<220> FEATURE:
<221> NAME/KEY: misc_feature
<222> LOCATION: (108)..(111)
<223> OTHER INFORMATION: Cathepsin G recognition sequence.
<220> FEATURE:
<221> NAME/KEY: misc_feature
<222> LOCATION: (538)..(541)
<223> OTHER INFORMATION: cathepsin G recognition sequence

<400> SEQUENCE: 21
```

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60
```

```
Gln Val Glu Ala Leu Met Asp Gln Lys Ile Ala Asp Tyr Ala Lys Asn
 65                  70                  75                  80

Lys Ala Leu Ala Glu Leu Gln Gly Leu Gln Asn Asn Val Glu Asp Tyr
                 85                  90                  95

Val Ser Ala Leu Ser Ser Trp Gln Lys Asn Pro Ala Ala Pro Phe Arg
                100                 105                 110

Asn Pro His Ser Gln Gly Arg Ile Arg Glu Leu Phe Ser Gln Ala Glu
            115                 120                 125

Ser His Phe Arg Asn Ser Met Pro Ser Phe Ala Ile Ser Gly Tyr Glu
            130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                165                 170                 175

Glu Asp Ile Ala Glu Phe Tyr Lys Arg Gln Leu Lys Leu Thr Gln Glu
            180                 185                 190

Tyr Thr Asp His Cys Val Lys Trp Tyr Asn Val Gly Leu Asp Lys Leu
            195                 200                 205

Arg Gly Ser Ser Tyr Glu Ser Trp Val Asn Phe Asn Arg Tyr Arg Arg
            210                 215                 220

Glu Met Thr Leu Thr Val Leu Asp Leu Ile Ala Leu Phe Pro Leu Tyr
225                 230                 235                 240

Asp Val Arg Leu Tyr Pro Lys Glu Val Lys Thr Glu Leu Thr Arg Asp
                245                 250                 255

Val Leu Thr Asp Pro Ile Val Gly Val Asn Asn Leu Arg Gly Tyr Gly
            260                 265                 270

Thr Thr Phe Ser Asn Ile Glu Asn Tyr Ile Arg Lys Pro His Leu Phe
            275                 280                 285

Asp Tyr Leu His Arg Ile Gln Phe His Thr Arg Phe Gln Pro Gly Tyr
290                 295                 300

Tyr Gly Asn Asp Ser Phe Asn Tyr Trp Ser Gly Asn Tyr Val Ser Thr
305                 310                 315                 320

Arg Pro Ser Ile Gly Ser Asn Asp Ile Ile Thr Ser Pro Phe Tyr Gly
                325                 330                 335

Asn Lys Ser Ser Glu Pro Val Gln Asn Leu Glu Phe Asn Gly Glu Lys
            340                 345                 350

Val Tyr Arg Ala Val Ala Asn Thr Asn Leu Ala Val Trp Pro Ser Ala
            355                 360                 365

Val Tyr Ser Gly Val Thr Lys Val Glu Phe Ser Gln Tyr Asn Asp Gln
370                 375                 380

Thr Asp Glu Ala Ser Thr Gln Thr Tyr Asp Ser Lys Arg Asn Val Gly
385                 390                 395                 400

Ala Val Ser Trp Asp Ser Ile Asp Gln Leu Pro Pro Glu Thr Thr Asp
                405                 410                 415

Glu Pro Leu Glu Lys Gly Tyr Ser His Gln Leu Asn Tyr Val Met Cys
            420                 425                 430

Phe Leu Met Gln Gly Ser Arg Gly Thr Ile Pro Val Leu Thr Trp Thr
            435                 440                 445

His Lys Ser Val Asp Phe Phe Asn Met Ile Asp Ser Lys Lys Ile Thr
            450                 455                 460

Gln Leu Pro Leu Val Lys Ala Tyr Lys Leu Gln Ser Gly Ala Ser Val
465                 470                 475                 480
```

```
Val Ala Gly Pro Arg Phe Thr Gly Gly Asp Ile Ile Gln Cys Thr Glu
                485                 490                 495

Asn Gly Ser Ala Ala Thr Ile Tyr Val Thr Pro Asp Val Ser Tyr Ser
            500                 505                 510

Gln Lys Tyr Arg Ala Arg Ile His Tyr Ala Ser Thr Ser Gln Ile Thr
        515                 520                 525

Phe Thr Leu Ser Leu Asp Gly Ala Pro Ala Ala Pro Phe Tyr Phe Asp
    530                 535                 540

Lys Thr Ile Asn Lys Gly Asp Thr Leu Thr Tyr Asn Ser Phe Asn Leu
545                 550                 555                 560

Ala Ser Phe Ser Thr Pro Phe Glu Leu Ser Gly Asn Asn Leu Gln Ile
                565                 570                 575

Gly Val Thr Gly Leu Ser Ala Gly Asp Lys Val Tyr Ile Asp Lys Ile
                580                 585                 590

Glu Phe Ile Pro Val
        595
```

<210> SEQ ID NO 22
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: BamExt1 Primer

<400> SEQUENCE: 22
ggatccacca tgacggccga c                                              21

<210> SEQ ID NO 23
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: AAPFtail3 Primer

<400> SEQUENCE: 23
gaacggtgca gcggggttct tctgccagc                                      29

<210> SEQ ID NO 24
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: AAPFtail4 Primer

<400> SEQUENCE: 24
gctgcaccgt tcccccacag ccagggccg                                      29

<210> SEQ ID NO 25
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: XbaIExt2 Primer

<400> SEQUENCE: 25
tctagaccca cgttgtacca c                                              21

<210> SEQ ID NO 26
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: Tail5mod Primer

<400> SEQUENCE: 26
gctgcaccgt tccgcaaccc ccacagcca                                29

<210> SEQ ID NO 27
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: SalExt Primer

<400> SEQUENCE: 27
gagcgtcgac ttcttcaac                                           19

<210> SEQ ID NO 28
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: AAPF-Y2 Primer

<400> SEQUENCE: 28
gaacggtgca gcgtattggt tgaaggggc                                30

<210> SEQ ID NO 29
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: AAPF-Y1 Primer

<400> SEQUENCE: 29
gctgcaccgt tctacttcga caagaccatc                               30

<210> SEQ ID NO 30
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: SacExt Primer

<400> SEQUENCE: 30
gagctcagat ctagttcacg g                                        21

<210> SEQ ID NO 31
<211> LENGTH: 32
<212> TYPE: DNA
<213> ORGANISM: Artificial Sequence
<220> FEATURE:
<221> NAME/KEY: misc_feature
<222> LOCATION: (1)..(32)

```
<223> OTHER INFORMATION: BBmod1 Primer

<400> SEQUENCE: 31
cggggccccc gctgcaccgt tctacttcga ca                    32

<210> SEQ ID NO 32
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: BBmod2 Primer

<400> SEQUENCE: 32
tgtcgaagta gaacggtgca gcggggggccc cg                   32

<210> SEQ ID NO 33
<211> LENGTH: 48
<212> TYPE: DNA
<213> ORGANISM: Artificial Sequence
<220> FEATURE:
<221> NAME/KEY: misc_feature
<222> LOCATION: (1)..(48)
<223> OTHER INFORMATION: mo3Aext Primer

<400> SEQUENCE: 33
ggatccacca tgaactacaa ggagttcctc cgcatgaccg ccgacaac   48

<210> SEQ ID NO 34
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: CMS16 Primer

<400> SEQUENCE: 34
cctccacctg ctccatgaag                                  20

<210> SEQ ID NO 35
<211> LENGTH: 4
<212> TYPE: PRT
<213> ORGANISM: Artificial Sequence
<220> FEATURE:
<221> NAME/KEY: PEPTIDE
<222> LOCATION: (1)..(4)
<223> OTHER INFORMATION: Protease recognition sequence

<400> SEQUENCE: 35

Ala Ala Pro Phe
1

<210> SEQ ID NO 36
<211> LENGTH: 4
<212> TYPE: PRT
<213> ORGANISM: Artificial Sequence
<220> FEATURE:
<221> NAME/KEY: Peptide
<222> LOCATION: (1)..(4)
<223> OTHER INFORMATION: Protease recognition sequence

<400> SEQUENCE: 36

Ala Ala Pro Met
1
```

```
<210> SEQ ID NO 37
<211> LENGTH: 4
<212> TYPE: PRT
<213> ORGANISM: Artificial Sequence
<220> FEATURE:
<221> NAME/KEY: Peptide
<222> LOCATION: (1)..(4)
<223> OTHER INFORMATION: Protease recognition sequence

<400> SEQUENCE: 37

Ala Val Pro Phe
1

<210> SEQ ID NO 38
<211> LENGTH: 4
<212> TYPE: PRT
<213> ORGANISM: Artificial Sequence
<220> FEATURE:
<221> NAME/KEY: Peptide
<222> LOCATION: (1)..(4)
<223> OTHER INFORMATION: Protease recognition sequence

<400> SEQUENCE: 38

Pro Phe Leu Phe
1
```